United States Patent [19]

Ohashi et al.

[11] Patent Number: 5,919,928
[45] Date of Patent: Jul. 6, 1999

[54] PHENANTHRIDINE DERIVATIVES AND METAL COMPLEXES THEREOF USED FOR TRANSPARENT RECORDING MEDIUM OR OPTICAL RECORDING MEDIUM

[75] Inventors: Reiji Ohashi; Yukiko Ryu; Tomoaki Nagai; Hidetoshi Yoshioka, all of Tokyo, Japan

[73] Assignee: Nippon Paper Industries, Co., Ltd., Tokyo, Japan

[21] Appl. No.: 08/933,604

[22] Filed: Sep. 18, 1997

Related U.S. Application Data

[62] Division of application No. 08/631,947, Apr. 15, 1996, Pat. No. 5,792,863.

[30] Foreign Application Priority Data

Apr. 14, 1995 [JP] Japan ..................... 7-113580

[51] Int. Cl.$^6$ .................. C07D 413/12; C07D 221/12
[52] U.S. Cl. ............... 544/64; 544/126; 544/225; 544/226; 544/327; 544/328; 544/329; 546/6; 546/10; 546/108
[58] Field of Search .............. 546/108, 6, 10; 544/64, 126, 225, 226, 327, 328, 329

[56] References Cited

FOREIGN PATENT DOCUMENTS

| | | |
|---|---|---|
| 55-9703 | 7/1980 | Japan . |
| 57-46245 | 3/1982 | Japan . |
| 58-83344 | 5/1983 | Japan . |
| 58-94494 | 6/1983 | Japan . |
| 58-209594 | 12/1983 | Japan . |
| 58-224793 | 12/1983 | Japan . |
| 59-2880 | 1/1984 | Japan . |
| 59-42994 | 3/1984 | Japan . |
| 60-241059 | 11/1985 | Japan . |
| 63-45087 | 2/1988 | Japan . |
| 63-227569 | 9/1988 | Japan . |
| 1-254772 | 10/1989 | Japan . |
| 1-294088 | 11/1989 | Japan . |
| 2-568 | 1/1990 | Japan . |
| 2-667 | 1/1990 | Japan . |
| 2-73865 | 3/1990 | Japan . |
| 2-76884 | 3/1990 | Japan . |
| 5-177950 | 7/1993 | Japan . |
| 6-273959 | 9/1994 | Japan . |

OTHER PUBLICATIONS

Joseph A. Castellano, et al., Liquid Crystals. II.$^1$Effects of Terminal Group Substitution on the Mesomorphic Behavior of Some Benzylideneanilines, Journal of Organic Chemistry vol. 33, No. 9, pp. 3501–3504, Sep. 1968.

S.V.Kessar, et al., New Routes to Condensed Polynuclear Compounds–VIII, Tetrahedron, vol. 29 pp. 177–184, 1973.

C.F.H Allen, et al., Acridone, Organic Synthesis, II, pp. 15–17, 1943.

Magidson et al., Berichte, 66, 866–872, 1933.

Adrien Albert, et al., Acridine Syntheses and Reactions. Part V. A New Dehalogenation of 5–Chloroacridine and its Derivatives, Journal of the Chemical Society, pp. 1148–1151, 1949.

H.T. Clarke, et al., Organic Synthesis, I, pp. 150–153, 1941.

*Primary Examiner*—Mukund J. Shah
*Assistant Examiner*—Deepak R. Rao
*Attorney, Agent, or Firm*—Knobbe, Martens, Olson & Bear, LLP

[57] ABSTRACT

A phenanthridine derivative metal complex of formula 1 having a large absorption in the near-infrared range and a reduced absorption in the visible range, which phenanthridine derivative metal complex is used in a transparent recording medium:

$$\left[ M^{k+}\cdots O = \begin{array}{c} (R^4)_m \\ \text{phenanthridine structure} \\ (R^6)_n \end{array} = N - \begin{array}{c} (R^3)_l \\ \text{aryl} \end{array} - N\begin{array}{c}R^1\\R^2\end{array} \right]_j (X)_l \quad (1)$$

where M is a metal atom, and X is a negative ion.

18 Claims, 12 Drawing Sheets

PHENANTHRIDINE DERIVATIVES AND METAL COMPLEXES THEREOF USED FOR TRANSPARENT RECORDING MEDIUM OR OPTICAL RECORDING MEDIUM

BACKGROUND

This application is a divisional of U.S. patent application Ser. No. 08/631,947, filed Apr. 15, 1996 now U.S. Pat. No. 5,792,863.

FIELD OF THE INVENTION

The present invention relates to an acridine derivative or phenanthridine derivative (hereinafter referred to as an indoaniline derivative) and metal complexes thereof useful in a transparent recording medium from which a record having a visible ray absorption can be obtained directly by using near infrared rays, and to a transparent recording medium and optical recording medium, such as optical disks useful in masking material for platemaking to be employed in the printing step, and containing a new indoaniline metal complex.

BACKGROUND OF THE ART

Thus far, the following recording mediums are known for obtaining recording with visible-range absorption directly by heat. A heat-sensitive recording medium used with a facsimile machine or the like is made by applying a painting solution to an opaque support member such as paper which is obtained by dispersing and mixing a colorless or light-colored electron donor substance (leuco dye) and an electron acceptor substance (developer) in an aqueous solution of a water-soluble binder and atomizing the mixed particles. Other transparent recording media employing a nitrogen- or sulfur-containing onium compound as both a developer and thermal activator are prepared by dissolving a dye and developer in an organic solvent and applying the obtained solution to a transparent support member, which are disclosed in Japanese Patent Laid-Open (ko-kai) Nos. 294088/1989 and 45087/1988. These are materials for recording an image by a direct heating method in which a recording medium is directly heated with a thermal head kept in contact with it.

On the other hand, members and methods for recording an image by irradiating near-infrared rays rather than by direct heating, are disclosed in Japanese Patent Laid-Open (ko-kai) Nos. 94494/1983, 2880/1984 and 42994/1984. Japanese Patent Laid-Open (ko-kai) No. 94494/1983 discloses an optical recording medium prepared by applying a coating liquid comprising not only a dye and a developer but also a near-infrared absorbing agent dispersed in a water-soluble binder to a support member. Japanese Patent Laid-Open (ko-kai) Nos. 2880/1984, 42994/1983 disclose optical recording media prepared by individually laminating a dye, a developer, and a near-infrared absorbing agent on a substrate by vacuum evaporation. Also, Japanese Patent Laid-Open (ko-kai) No. 209594/1983 discloses a transparent recording medium wherein so-called "background fogging" is prevented by the provision of an isolating layer prepared by coating a solution of a near-infrared absorbing agent in the interface between the coating layer prepared by applying a solution of a leuco dye dissolved in an organic solvent to a substrate and that of a developer solution provided thereabove.

Japanese Patent Laid-Open (ko-kai) No. 177950/1993 discloses a transparent recording medium wherein the relevant "background fogging" is completely prevented. In Japanese Patent Laid-Open (ko-kai) No. 177950/1993, a complete prevention of "background fogging" is implemented by the provision of a transparent recording layer formed by coating a solution, comprising a developer expressed in the general formula (5) mentioned above for protecting at least one of functionally developable phenol-type hydroxide and a metal salt of organic acid or a leuco dye to develop a color in reaction with said developer dissolved in an organic solvent, onto a transparent substrate. In Japanese Patent Laid-Open (ko-kai) No. 177950/1993, the transparent recording medium is employed as an OHP (overhead projector) film, slide, copying draft, or a photo mask for preparing the circuit pattern of a resin circuit board or an integrated circuit board. Near-infrared absorbing materials include immonium compounds such as IRG002 (trade name) and IRG022 (trade name) available from Nippon Kayaku K.K., dithiol nickel complexes, cyanine dyes such as 1,1,5,5-tetraxis (p-dimethylaminophenyl)-3-methoxy-1, 4-pentadiene toluene, squalerium dyes, naphthoquinone dyes, phthalocyanine compounds, and naphthalocyanine compounds.

Furthermore, as an application of this transparent recording medium, a masking material for print platemaking can be mentioned. With computerization of the printing process, various image forming methods interchangeable with conventional silver salt photography method are examined in the platemaking step and also as proofs for color proof-correction. In contrast to the silver salt photography method dealing chiefly with analog images, the laser recording method, the electronic photography method, the thermal transcription method, and the like can also form an image by using a digital signal and can provide a high quality printing block material and color correction proof at high speed. As a digital recording device, semiconductor lasers are most often employed from the standpoint of small size, durability, direct convertibility, low price and the like. As near-infrared sensitizers responsive to near-infrared rays irradiated from a semiconductor laser, employed are near-infrared absorbing materials such as phthalocyanine coloring substances described in Japanese Patent Publication (ko-koku) No. 64064/1991, heptamethine cyanine coloring substances described in Japanese Patent Publication (ko-koku) No. 28143/1990, naphthoindolenine-type cyanine coloring substances described in Japanese Patent Laid-Open (ko-kai) No. 273959/1994) and the like. Also, with respect of image quality, silver salt photography still occupies the highest position as the image forming method, but needs treating liquids for a developer, bleaching/fixing solution and the like. Since the maintenance and control of treating liquid quality is troublesome, the treatment time is long, the disposal of development treating liquids is serious and so on, materials replacing silver salt photograph are being called for.

Generally, near-infrared absorbing materials are often employed for optical recording media such as optical disks. Optical disks give high-density recordings by irradiating near-infrared laser rays to a recording layer provided on a circular support member. A near-infrared absorbing material contained in the recording layer efficiently converts near-infrared laser rays into heat and effects a thermodynamic deformation such as decomposition, vaporization and dissolution. Playback of the recorded information is carried out by reading the difference in reflectance between the generated portion of deformation by laser irradiation and the not-generated portion of deformation. Here, the performance required for near-infrared absorbing material is to have the maximum wavelength of absorption near the wavelength of laser rays to be used for recording, exhibit a high extinction coefficient at this wave length, and have a high efficiency in converting light into heat. As examples of near-infrared absorbing materials employed for transparent recording mediums, there can be mentioned phthalocyanine-type coloring substances described in Japanese Patent Laid-Open (ko-kai) No. 97033/1980, phenalen-type coloring substances described in Japanese Patent Laid-Open (ko-kai) No. 83344/1983, naphthoquinone-type coloring substance described in Japanese Patent Laid-Open (ko-kai) No. 224793/1983, and indoaniline metal complexes described in Japanese Patent Laid-Open (ko-kai) Nos. 227569/1988, 254772/1989, 568/1990, 667/1990. Furthermore, attempts were made to efficiently absorb laser rays by modifying the structure of these indoaniline metal complexes in metal-contained compounds described in Japanese Patent Laid-Open (ko-kai) No. 73865/1990 and metal-contained pyridophenothiazone-type compounds described in Japanese Patent Laid-Open (ko-kai) No. 76884/1990, but neither a high recording density nor a high contrast between the recorded portion and the unrecorded portion was obtained, so that no basic solution has been achieved.

In forming an image on a transparent recording medium by using near-infrared laser rays as a light source, it is required that a near-infrared absorbing material contained in the transparent recording medium efficiently absorb and convert into thermal energy the energy of near-infrared laser rays having a predetermined wavelength used for an image recording into thermal energy. Using a transparent recording medium as the masking material for print platemaking to be employed in the printing step requires both a high recording density and a high contrast between the portion recorded by laser rays and the unrecorded portion. Japanese Patent Laid-Open (ko-kai) No. 227569/1988 discloses a single layer of indocyanine-type coloring substance provided on a substrate, but this indocyanine-type coloring substance has an absorption in the visible range and presents a problem in that a film of the single layer made by using this coloring substance develops a green color to form a recording medium lacking in contrast. Furthermore, cyanine-type coloring substances are generally subject to discoloration and fading by sunlight and have problems in light resistance and the like.

In addition, in applications to optical recording media, a single layer of phthalocyanine-type coloring substance provided on a substrate, described in Japanese Patent Laid-Open (ko-kai) No. 97033/1980, has problems of low sensitivity, a high decomposition point and difficult vapor deposition, and further, problems of low solubility in organic solvents and unavailability to coating by application. With the phenalene-type coloring substance described in Japanese Patent Laid-Open (ko-kai) No. 83344/1983 and the naphthoquinone-type coloring substance described in Japanese Patent Laid-Open (ko-kai) No. 224793/1983, because the efficiency of converting light into heat is low despite the easiness of vapor deposition, the thermal deformation in the portion irradiated by laser rays is insufficient and a contrast in reflectance between the recorded portion and the unrecorded portion decreases in the playback of information and the playback of information becomes difficult. Because of being generally inferior in stability for laser rays employed during playback, organic coloring substances have another problem that the conversion efficiency declines when additional-recording by laser rays, thereby disabling information to be recorded.

With due consideration for the present circumstances, it is one object of the present invention to provide a transparent recording medium, high in recording density, good in contrast and excellent in longevity such as light resistance, by using new indoaniline metal complexes and their compounds, high in near-infrared absorption, highly efficient in converting light into heat, low in visible absorption, and further, highly soluble in an organic solvent, capable of coating by application, and excellent in longevity such as light resistance.

SUMMARY OF THE INVENTION

As a result of intensive studies for solving the problems mentioned above, the present authors find how the problems mentioned above of a conventional transparent recording medium can be solved at once by using new indoaniline metal complexes according to the present invention as near-infrared absorbing materials in a transparent recording medium made by applying a solution, comprising (a) a developer and (b) metal salts of organic acids to develop a color in reaction with said developer, or a leuco dye, dissolved in an organic solvent, to a transparent support member, thereby leading to the perfection of the present invention.

As compared with the metal-containing indoaniline-type complex compounds described in Japanese Patent Laid-Open (ko-kai) No. 227569/1988, new indoaniline metal complexes according to the present invention, with an extended maximum wavelength of absorption, has a high absorption in the near-infrared range. And as compared with said publicly known metal-containing indoaniline-type complex compounds, the molar extinction coefficient also increases extremely and the efficiency of converting near-infrared laser rays into heat greatly rises. Even by using a small-output semiconductor near-infrared laser ray, an image having a sufficiently high recording density can be obtained on a transparent receding medium.

In a new indoaniline metal complex according to the present invention, since the conjugate system spreads out as compared with said publicly known metal-containing indoaniline-type complex compounds, the absorption spectrum is greatly shifted from the visible range to the near-infrared range. Because the absorption in the visible range decreases because of this red-shifting, the new indoaniline metal complex is slightly colored and the transparent recording medium made by using this as a near-infrared absorbing material for optical recording also has a low absorption in the visible range and slightly develops a color. The extinction coefficient greatly increases and the efficiency of converting near-infrared laser rays into heat greatly rises as well. Consequently, the recording density in recording by near-infrared laser rays is very high and the contrast in the obtained image is excellent. A new indoaniline metal complex exhibits a high solubility in organic solvents and is capable of coating by application. Generally, coloring substances having a metal complex structure are stable under ultraviolet light contained in sunlight or the like and include colorig substances functioning as a singlet oxygen quencher. Because of no discoloration and no change in the molar extinction coefficient or in the efficiency of converting near-infrared laser rays into heat even on a long exposure under sunlight, a new indoaniline metal complex according to the present invention is a coloring substance which is excellent in light resistance and the transparent recording medium made by using this complex is also excellent in light resistance.

That is, the present invention refers to a new indoaniline metal complex, suitable for a near-infrared absorbing material for optical recording applicable to transparent recording media on which a record with an absorption in the visible range can be obtained directly by near-infrared laser rays, represented by the following general formula (1):

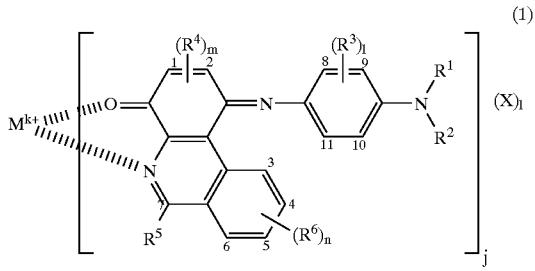

(in the formula, M denotes a metal atom, $R^1$ and $R^2$ denote a hydrogen atom, alkyl group, or aryl group, $R^3$ denotes a hydrogen atom or electron donating groups, and $R^4$, $R^5$ and $R^6$ denote a hydrogen atom or electron withdrawing groups, whereas i, j and k denote an integer of 1, 2 or 3, l and n denote an integer of 1–4, m denotes 1 or 2, and X denotes a negative ion) and by the following general formula (2):

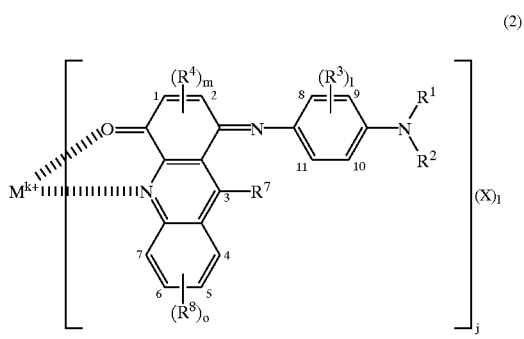

(in the formula, M denotes a metal atom, $R^1$ and $R^2$ denote a hydrogen atom, alkyl group, or aryl group, $R^3$ denotes a hydrogen atom or electron donating groups, and $R^4$, $R^7$ and $R^8$ denote a hydrogen atom or electron withdrawing groups, whereas i, j and k denote an integer of 1, 2 or 3, l and o denote an integer of 1–4, m denotes 1 or 2, and X denotes a negative ion).

DETAILED DESCRIPTION OF THE PREFERRED EMBODIMENT

Figure 1:
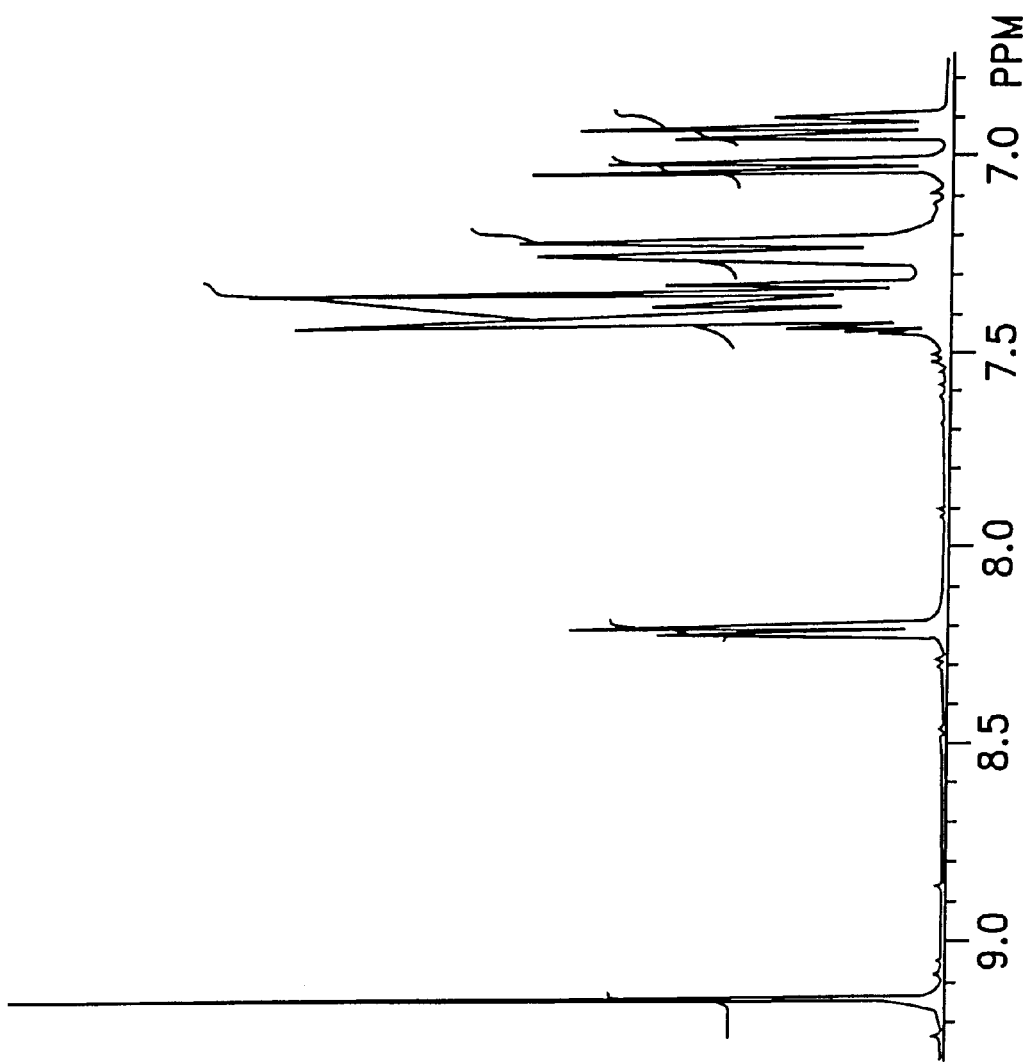
FIG. 1 is a spectral chart of $^1$H-NMR for N-(2-chlorobenzylidene)-2'-hydroxyaniline (12) obtained in Prepared Example 1-1-1.

Hereinafter, the present invention will be described in detail by referring to specific examples. As a metal atom denoted by M in the above-mentioned general formulae (1) or (2), Ni, Cu, Co, Zn, Fe, Pd, Pt or the like is mentioned. Among them, Ni, Cu, Co, Fe or the like is preferable metal atom.

Examples can be given of alkyl groups denoted by $R^1$ and $R^2$ as follows: methyl, ethyl, n-propyl, iso-propyl, n-butyl, iso-butyl, sec-butyl, tert-butyl, n-pentyl, n-hexyl, n-octyl, 2-ethylhexyl, lauryl, myristyl, palmityl, stearyl, 2-propenyl, 2-methyl-2-propenyl, 2-chloro-2-propenyl, 2-hydroxyethyl, 2-cyanoethyl, 2-aminoethyl, 2-chloroethyl, 2-bromoethyl, 2-iodoethyl, 2-fluoroethyl, trifluoromethyl, 2,2,2-trifluoroethyl, 2-methoxyethyl, 2-ethoxyethyl, methoxyethoxyethyl, 2-allyloxyethyl, benzyl, phenethyl, benzyloxymethyl, 2-benzyloxyethyl, methylcarbonyloxyethyl, benzylcarbonyloxymethyl, 2-phenoxyethyl, 2-acetoxyethyl, 2-carboxyethyl, ethoxycarbonylmethyl, methoxycarbonylethyl, 3-mesylpropyl, 2-furylmethyl, 2-oxolanylmethyl, cyclopentyl, cyclohexyl and 2-methylcyclohexyl, whereas examples of aryl groups are given as follows: phenyl, o-tolyl, m-tolyl, p-tolyl, o-chlorophenyl, m-chlorophenyl, p-chlorophenyl, o-bromophenyl, m-bromophenyl, p-bromophenyl, o-methoxyphenyl, m-methoxyphenyl, p-methoxyphenyl, p-ethoxyphenyl and p-n-butoxyphenyl. In addition, $R^1$s and $R^2$s may directly form rings, whose examples are ring structures such as pyrolidine, imidazolidine, piperidine, piperazine, morpholine and indoline. Examples can be given of electron donating groups denoted by $R^3$ as follows: alkyl groups, aralkyl groups, alkoxy groups, aryloxy groups, alkylthio groups, arylthio groups, alkyl-substituted amino groups, acylamino groups, sulfonylamino groups, and ureido groups. To be specific, alkyl groups include methyl, ethyl, n-propyl, iso-propyl, n-butyl, iso-butyl, sec-butyl, tert-butyl, n-pentyl, n-hexyl, n-octyl, 2-ethylhexyl, lauryl, myristyl, parmityl, stearyl, 2-hydroxyethyl, 2-cyanoethyl, 2-aminoethyl, 2-chloroethyl, 2-bromoethyl, 2-iodoethyl, 2-fluoroethyl, 2,2,2-trifluoroethyl, 2-methoxyethyl, methoxyethoxyethyl, 2-allyloxyethyl, benzyl, phenetyl, benzyloxymethyl, 2-benzyloxyethyl, methylcarbonyloxyethyl, benzylcarbonyloxymethyl, 2-phenoxyethyl, 2-acetoxyethyl, 2-carboxyethyl, ethoxycarbonylmethyl, methoxycarbonylethyl, 3-mesylpropyl, 2-furylmethyl, 2-oxolanylmethyl, cyclopentyl, cyclohexyl and 2-methylcyclohexyl; aralkyl groups include benzyl, phenethyl, benzhydrol and trityl; alkoxy groups include methoxy, ethoxy, n-propoxy, iso-propoxy, n-butoxy, iso-butoxy, sec-butoxy, and tert-butoxy; aryloxy groups include phenoxy, o-tolyloxy, m-tolyloxy, p-tolyloxy, o-chlorophenoxy, m-chlorophenoxy, p-chlorophenoxy, o-bromophenoxy, m-bromophenoxy, p-bromophenoxy, o-methoxyphenoxy, m-methoxyphenoxy, p-methoxyphenoxy, p-ethoxyphenoxy and p-butoxyphenoxy; alkylthio groups include methylthio, ethylthio, n-propylthio, iso-propylthio, n-butylthio, iso-butylthio, sec-butylthio, tert-butylthio and benzylthio; arylthio groups include phenylthio, o-tolylthio, m-tolylthio, p-tolylthio, o-chlorophenylthio, m-chlorophenylthio, p-chlorophenylthio, o-bromophenylthio, m-bromophenylthio, p-bromophenylthio, o-methoxyphenylthio, m-methoxyphenylthio, p-methoxyphenylthio, p-ethoxyphenylthio and p-butoxyphenylthio; and alkyl-substituted amino groups include dimethylamino, diethylamino, di-n-propylamino, di-iso-propylamino, di-n-butylamino, di-iso-butylamino, di-sec-butylamino, di-tert-butylamino, N-methyl-N-ethylamino, N-ethyl-N-iso-propylamino and N-ethyl-N-n-butylamino; acylamino groups include formylamino, acetylamino, propionylamino, butyrylamino, iso-butyrylamino, valerylamino, iso-valerylamino, pivaloylamino, lauroylamino, myristoylamino, palmitoylamino, stearoylamino, benzoylamino, 1-naphthoylamino and 2-naphthoylamino; sulfonylamino groups include mesylamino, ethanesulfonylamino and tosylamino; ureido groups include ureido, N-methylureido, N-n-propylureido, N-N-diethylureido, N-acetyl-N-phenylureodo, thioureido, N-methylthioureido, N-N-diethylthioureido and N-acetyl-N-phenylthioureodo.

Examples can be given of electron withdrawing groups denoted by $R^4$, $R^5$, $R^6$, $R^7$ and $R^8$ as follows: halogen atoms, trifluoromethyl, aryl groups, carbonyl groups, alkoxycarbonyl groups, aryloxycarbonyl groups, carbamoyl groups, sulfonyl groups, sulfamoyl groups, nitro, and cyano. To be specific, halogen atoms include chlorine, bromine, iodine and fluorine; aryl groups include phenyl, o-tolyl, m-tolyl, p-tolyl, o-chlorophenyl, m-chlorophenyl, p-chlorophenyl, o-bromophenyl, m-bromophenyl, p-bromophenyl, o-hydroxyphenyl, o-methoxyphenyl, m-methoxyphenyl, p-methoxyphenyl, p-ethoxyphenyl and p-butoxyphenyl; carbonyl groups include formyl, acetyl, propionyl, butyryl, iso-butyryl, valeryl, iso-valeryl, pivaloyl, lauroyl, myristoyl, palmitoyl, stearoyl, benzoyl, 1-naphthoyl and 2-naphthoyl; alkoxycarbonyl groups include methoxycarbonyl, ethoxycarbonyl, n-propoxycarbonyl, iso-propoxycarbonyl, n-butoxycarbonyl, iso-butoxycarbonyl, sec-butoxycarbonyl, tert-butoxycarbonyl, lauryloxycarbonyl, myristyloxycarbonyl, palmityloxycarbonyl and stearyloxycarbonyl; aryloxycarbonyl groups include phenoxycarbonyl, o-tolyloxycarbonyl, m-tolyloxycarbonyl, p-tolyloxycarbonyl, o-chlorophenoxycarbonyl, m-chorophenoxycarbonyl, p-chlorophenoxycarbonyl, o-bromophenoxycarbonyl, m-bromophenoxycarbonyl, p-bromophenoxycarbonyl, o-methoxyphenoxycarbonyl, m-methoxyphenoxycarbonyl, p-methoxyphenoxycarbonyl, p-ethoxyphenoxycarbonyl, p-butoxyphenoxycarbonyl, hydroxyiminomethylcarbonyl, bromoacetyl, hydroxycarbonyl, methoxycarbonyl, n-hexylcarbonyl, aminothiocarbonyl, and hydroxycarbonylmethyl; carbamoyl groups include N-phenylcarbamoyl, N-4-bromophenylcarbamoyl, N-methylcarbamoyl, N-ethylcarbamoyl, N-2-hydroxyethylcarbamoyl, N-2-methoxyethylcarbamoyl, N-ethoxymethylcarbamoyl, N-oxolanyl-methyl-carbamoyl, N-allylcarbamoyl, N-2-thienylcarbamoyl, N-3-(2-methoxycarbonyl)thienylcarbamoyl, N-2-(4-nitro)thienylcarbamoyl, N-2-thiazolylcarbamoyl, N-(4-methylsulfonyl)phenylcarbamoyl, N-(4-cyano) phenylcarbamoyl, N-2-benzoimidazolylcarbamoyl, N-2-benzoxazolylcarbamoyl, N-2-benzothiazolylcarbamoyl, N-2-pyridylcarbamoyl, N-4-pyridylcarbamoyl, N-4-pyrimidylcarbamoyl, N-2-quinolylcarbamoyl, N-4-quinolylcarbamoyl and N-3H-indo-2-lylcarbamoyl; sulfonyl groups include mesyl, ethanesulfonyl and tosyl; and sulfamoyl groups include N-phenylsulfamoyl, N-4-bromophenylsulfamoyl, N-methylsulfamoyl, N-ethylsulfamoyl, N-2-hydroxyethylsulfamoyl, N-2-methoxyethylsulfamoyl, N-ethoxymethylsulfamoyl, N-oxolanylmetylsulfamoyl, N-allylsulfamoyl, N-2-thienylsulfamoyl, N-2-(4-nitro)thienylsulfamoyl, N-2-thiazolylsulfamoyl, N-(4-methylsulfonyl)phenylsulfamoyl, N-(4-cyano)phenylsulfamoyl, N-phenyl(4-cyano)sulfamoyl, N-2-benzoimidazolylsulfamoyl, N-2-benzoxazolylsulfamoyl, N-2-benzothiazolylsulfamoyl, N-2-pyridylsulfamoyl, N-4-pyridylsulfamoyl, N-4-pyrimidylsulfamoyl, N-2-quinolylsulfamoyl, N-4-quinolylsulfamoyl and N-3H-indo-2-lylsulfamoyl.

Negative ions denoted by X include $F^-$, $Cl^-$, $Br^-$, $I^-$, $ClO_4^-$, $SCN^-$, $BF_4^-$, $PF_6^-$, $SbF_6^-$, $TiF_6^{2-}$, $ZrF_6^{2-}$, $SiF_6^{2-}$, $OH^-$, $TsO^-$, $HCOO^-$, $CH_3COO^-$, $NO_3^-$, $H_2PO_4^-$, $BPh_4^-$ and $CN^-$, but preferably are $Cl^-$, $Br^-$, $I^-$, $ClO_4^-$, $BF_4^-$, $PF_6^-$ and $SbF_6^-$.

Hereinafter, specific examples of new indoaniline metal complexes represented by the following general formulae (1) and (2) will be mentioned, but the present invention is not limited to these examples. In the tables that follow, l, m, n, and o are indicated as 0 (zero) where the appropriate R group is a hydrogen atom, i.e., l, m, n, and o are technically 1 (one).

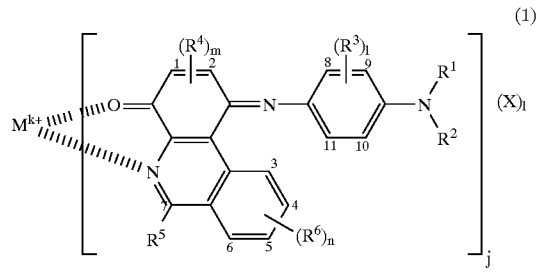

(1)

TABLE 1

| No. | $R^1$ | $R^2$ | $R^3$ | $R^4$ | $R^5$ | $R^6$ | M | X | i | j | k | l | m | n |
|---|---|---|---|---|---|---|---|---|---|---|---|---|---|---|
| 1-1 | ethyl | ethyl | 8-methyl | H | H | H | Cu | $ClO_4$ | 2 | 2 | 2 | 1 | 0 | 0 |
| 1-2 | ethyl | ethyl | H | H | H | H | Cu | $ClO_4$ | 2 | 2 | 2 | 0 | 0 | 0 |

TABLE 1-continued

| No. | R¹ | R² | R³ | R⁴ | R⁵ | R⁶ | M | X | i | j | k | l | m | n |
|---|---|---|---|---|---|---|---|---|---|---|---|---|---|---|
| 1-3 | methyl | methyl | H | R | H | H | Cu | ClO₄ | 2 | 2 | 2 | 0 | 0 | 0 |
| 1-4 | n-propyl | n-propyl | H | H | H | H | Cu | ClO₄ | 2 | 2 | 2 | 0 | 0 | 0 |
| 1-5 | i-propyl | i-propyl | H | H | H | H | Cu | ClO₄ | 2 | 2 | 2 | 0 | 0 | 0 |
| 1-6 | n-butyl | n-butyl | H | H | H | H | Cu | ClO₄ | 2 | 2 | 2 | 0 | 0 | 0 |
| 1-7 | s-butyl | H | H | H | H | H | Cu | ClO₄ | 2 | 2 | 2 | 0 | 0 | 0 |
| 1-8 | n-pentyl | n-pentyl | H | H | H | H | Cu | ClO₄ | 2 | 2 | 2 | 0 | 0 | 0 |
| 1-9 | n-hexyl | n-hexyl | H | H | H | H | Cu | ClO₄ | 2 | 2 | 2 | 0 | 0 | 0 |
| 1-10 | 2-ethylhexyl | 2-ethylhexyl | H | H | H | H | Cu | ClO₄ | 2 | 2 | 2 | 0 | 0 | 0 |
| 1-11 | cetyl | cetyl | H | H | H | H | Cu | ClO₄ | 2 | 2 | 2 | 0 | 0 | 0 |
| 1-12 | ethyl | 2-cyanoethyl | H | H | H | H | Cu | ClO₄ | 2 | 2 | 2 | 0 | 0 | 0 |
| 1-13 | ethyl | 2-chloroethyl | H | H | H | H | Cu | ClO₄ | 2 | 2 | 2 | 0 | 0 | 0 |
| 1-14 | 2-ethoexyethyl | 2-ethoxyethyl | H | H | H | H | Cu | ClO₄ | 2 | 2 | 2 | 0 | 0 | 0 |
| 1-15 | methoxyethoxyethyl | methoxyethoxyethyl | H | H | H | H | Cu | ClO₄ | 2 | 2 | 2 | 0 | 0 | 0 |
| 1-16 | benzyl | benzyl | H | H | Ph | H | Cu | ClO₄ | 2 | 2 | 2 | 0 | 0 | 0 |
| 1-17 | ethyl | benzyloxyethyl | H | H | Ph | H | Cu | ClO₄ | 2 | 2 | 2 | 0 | 0 | 0 |
| 1-18 | ethyl | methylcarbonyloxyethyl | H | H | Ph | H | Cu | ClO₄ | 2 | 2 | 2 | 0 | 0 | 0 |
| 1-19 | ethyl | 2-phenoxyethyl | H | H | Ph | H | Cu | ClO₄ | 2 | 2 | 2 | 0 | 0 | 0 |
| 1-20 | ethyl | 2-acetoxyethyl | H | H | Ph | H | Cu | ClO₄ | 2 | 2 | 2 | 0 | 0 | 0 |
| 1-21 | 2-carboxyethyl | 2-carboxyethyl | H | H | H | H | Cu | ClO₄ | 2 | 2 | 2 | 0 | 0 | 0 |

TABLE 2

| No. | R¹ | R² | R³ | R⁴ | R⁵ | R⁶ | M | X | i | j | k | l | m | n |
|---|---|---|---|---|---|---|---|---|---|---|---|---|---|---|
| 1-22 | ethoxycarbonylmethyl | ethoxycarbonylmethyl | H | H | H | H | Cu | ClO₄ | 2 | 2 | 2 | 0 | 0 | 0 |
| 1-23 | 3-mesylpropyl | 3-mesylpropyl | H | H | H | H | Cu | ClO₄ | 2 | 2 | 2 | 0 | 0 | 0 |
| 1-24 | ethyl | 2-oxolanylmethyl | H | H | H | H | Cu | ClO₄ | 2 | 2 | 2 | 0 | 0 | 0 |
| 1-25 | H | phenyl | H | H | H | H | Cu | ClO₄ | 2 | 2 | 2 | 0 | 0 | 0 |
| 1-26 | H | p-tolyl | H | H | H | H | Cu | ClO₄ | 2 | 2 | 2 | 0 | 0 | 0 |
| 1-27 | H | p-chlorophenyl | H | H | H | H | Cu | ClO₄ | 2 | 2 | 2 | 0 | 0 | 0 |
| 1-28 | H | p-methoxyphenyl | H | H | H | H | Cu | ClO₄ | 2 | 2 | 2 | 0 | 0 | 0 |
| 1-29 | H | p-n-butoxyphenyl | H | H | H | H | Cu | ClO₄ | 2 | 2 | 2 | 0 | 0 | 0 |
| 1-30 | 2-propenyl | 2-propenyl | H | H | H | H | Cu | ClO₄ | 2 | 2 | 2 | 0 | 0 | 0 |
| 1-31 | ethyl | 2-methyl-2-propenyl | H | H | H | H | Cu | ClO₄ | 2 | 2 | 2 | 0 | 0 | 0 |
| 1-32 | ethyl | 2-chloro-2-propenyl | H | H | H | H | Cu | ClO₄ | 2 | 2 | 2 | 0 | 0 | 0 |
| 1-33 | ethyl | cyclohexyl | H | H | H | H | Cu | ClO₄ | 2 | 2 | 2 | 0 | 0 | 0 |
| 1-34 | piperidinyl | | H | H | H | H | cu | ClO₄ | 2 | 2 | 2 | 0 | 0 | 0 |
| 1-35 | morpholinyl | | H | H | H | H | Cu | ClO₄ | 2 | 2 | 2 | 0 | 0 | 0 |
| 1-38 | ethyl | ethyl | 8-ethyl | H | H | H | Cu | ClO₄ | 2 | 2 | 2 | 1 | 0 | 0 |
| 1-39 | ethyl | ethyl | 8-cyclohexyl | H | H | H | Cu | ClO₄ | 2 | 2 | 2 | 1 | 0 | 0 |
| 1-40 | ethyl | ethyl | 8-phenyl | H | H | H | Cu | ClO₄ | 2 | 2 | 2 | 1 | 0 | 0 |
| 1-41 | ethyl | ethyl | 8-(2-propenyl) | H | H | H | Cu | ClO₄ | 2 | 2 | 2 | 1 | 0 | 0 |
| 1-42 | ethyl | ethyl | 8-benzyl | H | H | H | Cu | ClO₄ | 2 | 2 | 2 | 1 | 0 | 0 |

TABLE 3

| No. | R¹ | R² | R³ | R⁴ | R⁵ | R⁶ | M | X | i | j | k | l | m | n |
|---|---|---|---|---|---|---|---|---|---|---|---|---|---|---|
| 1-43 | ethyl | ethyl | 8-methoxy | H | H | H | Cu | ClO₄ | 2 | 2 | 2 | 1 | 0 | 0 |
| 1-44 | 2-phenoxyethyl | 2-phenoxyethyl | 8,10-diethoxy | H | H | H | Cu | ClO₄ | 2 | 2 | 2 | 2 | 0 | 0 |
| 1-45 | 2-ethoyxethyl | 2-ethoxyethylhyl | 8-methoxy-10-methyl | H | H | H | Cu | ClO₄ | 2 | 2 | 2 | 2 | 0 | 0 |
| 1-49 | n-butyl | n-butyl | 8-diethylamino | H | H | H | Cu | ClO₄ | 2 | 2 | 2 | 1 | 0 | 0 |
| 1-50 | n-butyl | n-butyl | 8-diisopropylamino | H | H | H | Ni | ClO₄ | 2 | 2 | 2 | 1 | 0 | 0 |
| 1-51 | n-butyl | n-butyl | 8-tosylamino | H | H | H | Ni | ClO₄ | 2 | 2 | 2 | 1 | 0 | 0 |
| 1-52 | ethyl | ethyl | 8-mesylamino | H | H | H | Cu | ClO₄ | 2 | 2 | 2 | 1 | 0 | 0 |
| 1-53 | n-butyl | n-butyl | 8-laurolyamino | H | H | H | Cu | ClO₄ | 2 | 2 | 2 | 1 | 0 | 0 |
| 1-54 | ethyl | ethyl | 8-palmitoylamino | H | H | H | Ni | ClO₄ | 2 | 2 | 2 | 1 | 0 | 0 |
| 1-55 | ethyl | ethyl | 8-stearoylamino | H | H | H | Ni | ClO₄ | 2 | 2 | 2 | 1 | 0 | 0 |
| 1-56 | ethyl | ethyl | 8-(1-naphthoylamino) | H | H | H | Ni | ClO₄ | 2 | 2 | 2 | 1 | 0 | 0 |
| 1-57 | 2-ethylhexyl | 2-ethylhexyl | H | H | H | H | Ni | ClO₄ | 2 | 2 | 2 | 1 | 0 | 0 |
| 1-58 | 2-ethylhexyl | 2-ethylhexyl | H | H | H | H | Fe | ClO₄ | 3 | 2 | 3 | 1 | 0 | 0 |
| 1-59 | ethyl | ethyl | 8-n-butylthio | H | H | H | Cu | ClO₄ | 2 | 2 | 2 | 1 | 0 | 0 |
| 1-60 | n-butyl | n-butyl | 8-phenylethio | H | H | H | Cu | Cl | 2 | 2 | 2 | 1 | 0 | 0 |
| 1-61 | ethyl | ethyl | 8-p-chlorophenylthio | H | H | H | Cu | Br | 2 | 2 | 2 | 1 | 0 | 0 |
| 1-62 | n-butyl | n-butyl | 8-benzylthio | H | H | H | Cu | I | 2 | 2 | 2 | 1 | 0 | 0 |
| 1-63 | ethyl | ethyl | 8-ureido | H | H | H | Cu | BF₄ | 2 | 2 | 2 | 1 | 0 | 0 |

TABLE 4

| No. | R¹ | R² | R³ | R⁴ | R⁵ | R⁶ | M | X | i | j | k | l | m | n |
|---|---|---|---|---|---|---|---|---|---|---|---|---|---|---|
| 1-64 | n-butyl | n-butyl | 8-N-n-propylureido | H | H | H | Cu | $PF_6$ | 2 | 2 | 2 | 1 | 0 | 0 |
| 1-65 | ethyl | ethyl | 8-N,N-diethylureido | H | H | H | Cu | $ClO_4$ | 2 | 2 | 2 | 1 | 0 | 0 |
| 1-66 | ethyl | ethyl | 8-thioureido | H | H | H | Cu | $ClO_4$ | 2 | 2 | 2 | 1 | 0 | 0 |
| 1-67 | ethyl | ethyl | 8-N-acetyl-N-phenylthioureido | H | H | H | Cu | $SbF_6$ | 2 | 2 | 2 | 1 | 1 | 0 |
| 1-68 | ethyl | ethyl | 8-methyl | 1-acetyl | H | H | Cu | $ClO_4$ | 2 | 3 | 2 | 1 | 1 | 0 |
| 1-69 | ethyl | ethyl | 8-methyl | 1-isovaleryl | H | H | Cu | $ClO_4$ | 2 | 3 | 2 | 1 | 1 | 0 |
| 1-70 | ethyl | ethyl | 8-methyl | 1-stearoyl | H | H | Cu | $ClO_4$ | 2 | 3 | 2 | 1 | 1 | 0 |
| 1-71 | ethyl | ethyl | 8-methyl | 1-benzoyl | H | H | Cu | $ClO_4$ | 2 | 3 | 2 | 1 | 1 | 0 |
| 1-72 | ethyl | ethyl | 8-methyl | 1-(1-naphthoyl) | H | H | Cu | $ClO_4$ | 2 | 3 | 2 | 1 | 1 | 0 |
| 1-73 | ethyl | ethyl | 8-methyl | 1-carboxy | H | H | Cu | $ClO_4$ | 2 | 2 | 2 | 1 | 1 | 0 |
| 1-74 | ethyl | ethyl | 8-methyl | 1-N-phenylcarbamoyl | H | H | Cu | $ClO_4$ | 2 | 2 | 2 | 1 | 1 | 0 |
| 1-75 | ethyl | ethyl | 8-methyl | 1-N-methylcarbamoyl | H | H | Cu | $ClO_4$ | 2 | 2 | 2 | 1 | 1 | 0 |
| 1-76 | ethyl | ethyl | 8-methyl | 1-N-ethoxymnethylcarbamoyl | H | H | Cu | $ClO_4$ | 2 | 2 | 2 | 1 | 1 | 0 |
| 1-77 | ethyl | ethyl | 8-methyl | 1-(N-2-oxolanylmethylcarbamoyl) | H | H | Cu | ClO4 | 2 | 2 | 2 | 1 | 1 | 0 |
| 1-78 | ethyl | ethyl | 8-methyl | 1-N-allylcarbamoyl | H | H | Cu | $ClO_4$ | 2 | 2 | 2 | 1 | 1 | 0 |
| 1-79 | ethyl | ethyl | 8-methyl | 1-(N-3-(2-methoxycarbonyl)thienylcarbamoyl) | H | H | Cu | $ClO_4$ | 2 | 2 | 2 | 1 | 1 | 0 |
| 1-80 | ethyl | ethyl | 8-methyl | 1-N-2-thiazaolylacarbamoyl | H | H | Cu | $ClO_4$ | 2 | 2 | 2 | 1 | 1 | 0 |
| 1-81 | ethyl | ethyl | 8-methyl | 1-(N-2-benzoimidazolylcarbamoyl) | H | H | Cu | $ClO_4$ | 2 | 2 | 2 | 1 | 1 | 0 |
| 1-82 | ethyl | ethyl | 8-methyl | 1-(N-2-benzoxazolylcarbamoyl) | H | H | Cu | $ClO_4$ | 2 | 2 | 2 | 1 | 1 | 0 |
| 1-83 | ethyl | ethyl | 8-methyl | 1-(N-2-benzothiazolylcarbamoyl) | H | H | Cu | $ClO_4$ | 2 | 2 | 2 | 1 | 1 | 0 |
| 1-84 | ethyl | ethyl | 8-methyl | 1-(N-2-pyridylcarbamoyl) | H | H | Cu | $ClO_4$ | 2 | 2 | 2 | 1 | 1 | 0 |

TABLE 5

| No. | R¹ | R² | R³ | R⁴ | R⁵ | R⁶ | M | X | i | j | k | l | m | n |
|---|---|---|---|---|---|---|---|---|---|---|---|---|---|---|
| 1-85 | ethyl | ethyl | 8-methyl | 1-(N-2-pyrimidylcarbamoyl) | H | H | Cu | $ClO_4$ | 2 | 2 | 2 | 1 | 1 | 0 |
| 1-86 | ethyl | ethyl | 8-methyl | 1-(N-2-quinolylcarbamoyl) | H | H | Cu | $ClO_4$ | 2 | 2 | 2 | 1 | 1 | 0 |
| 1-87 | ethyl | ethyl | 8-methyl | 1-(N-3H-indo-2-lylcarbamoyl) | H | H | Cu | $ClO_4$ | 2 | 2 | 2 | 1 | 1 | 0 |
| 1-88 | ethyl | ethyl | 8-methyl | 1-sulfo | H | H | Cu | $ClO_4$ | 2 | 2 | 2 | 1 | 1 | 0 |
| 1-89 | ethyl | ethyl | 8-methyl | 1-N-phenylsulfamoyl | H | H | Cu | $ClO_4$ | 2 | 2 | 2 | 1 | 1 | 0 |
| 1-90 | ethyl | ethyl | 8-methyl | 1-N-methylsulfamoyl | H | H | Cu | $ClO_4$ | 2 | 2 | 2 | 1 | 1 | 0 |
| 1-91 | ethyl | ethyl | 8-methyl | 1-N-ethoxymethylsulfamoyl | H | H | Cu | $ClO_4$ | 2 | 2 | 2 | 1 | 1 | 0 |
| 1-92 | ethyl | ethyl | 8-methyl | 1-(N-2-oxolanylmethylsulfamoyl) | H | H | Cu | $ClO_4$ | 2 | 2 | 2 | 1 | 1 | 0 |
| 1-93 | ethyl | ethyl | 8-methyl | 1-N-allylsulfamoyl | H | H | Cu | $ClO_4$ | 2 | 2 | 2 | 1 | 1 | 0 |
| 1-94 | ethyl | ethyl | 8-methyl | 1-(N-2-thienylsulfamoyl) | H | H | Cu | $ClO_4$ | 2 | 2 | 2 | 1 | 1 | 0 |
| 1-95 | ethyl | ethyl | 8-methyl | 1-(N-2-thiazolylsulfamoyl) | H | H | Cu | $ClO_4$ | 2 | 2 | 2 | 1 | 1 | 0 |
| 1-96 | ethyl | ethyl | 8-methyl | 1-(N-2-benzoimidazolylsulfamoyl) | H | H | Cu | $ClO_4$ | 2 | 2 | 2 | 1 | 1 | 0 |
| 1-97 | ethyl | ethyl | 8-methyl | 1-(N-2-benzoxazolylsulfamoyl) | H | H | Cu | $ClO_4$ | 2 | 2 | 2 | 1 | 1 | 0 |
| 1-98 | ethyl | ethyl | 8-methyl | 1-(N-2-benzothiazolylsulfamoyl) | H | H | Cu | $ClO_4$ | 2 | 2 | 2 | 1 | 1 | 0 |
| 1-99 | ethyl | ethyl | 8-methyl | 1-(N-2-pyridylsulfamoyl) | H | H | Cu | $ClO_4$ | 2 | 2 | 2 | 1 | 1 | 0 |
| 1-100 | ethyl | ethyl | 8-methyl | 1-(N-2-pyrimidylsulfamoyl) | H | H | Cu | $ClO_4$ | 2 | 2 | 2 | 1 | 1 | 0 |
| 1-101 | ethyl | ethyl | 8-methyl | 1-(N-2-quinolylsulfamoyl) | H | H | Cu | $ClO_4$ | 2 | 2 | 2 | 1 | 1 | 0 |
| 1-102 | ethyl | ethyl | 8-methyl | 1-(N-3H-indo-2-lylsulfamoyl) | H | H | Cu | $ClO_4$ | 2 | 2 | 2 | 1 | 1 | 0 |
| 1-103 | ethyl | ethyl | 8-methyl | 1-methoxycarbonyl | H | H | Cu | $ClO_4$ | 2 | 2 | 2 | 1 | 1 | 0 |
| 1-104 | ethyl | ethyl | 8-methyl | 1-ethoxycarbonyl | H | H | Cu | $ClO_4$ | 2 | 2 | 2 | 1 | 1 | 0 |
| 1-105 | ethyl | ethyl | 8-methyl | 1-n-butoxycarbonyl | H | H | Cu | $ClO_4$ | 2 | 2 | 2 | 1 | 1 | 0 |

TABLE 6

| No | R¹ | R² | R³ | R⁴ | R⁵ | R⁶ | M | X | i | j | k | l | m | n |
|---|---|---|---|---|---|---|---|---|---|---|---|---|---|---|
| 1-106 | ethyl | ethyl | 8-methyl | 1-lauryloxycarbonyl | H | H | Cu | $ClO_4$ | 2 | 2 | 2 | 1 | 1 | 0 |
| 1-107 | ethyl | ethyl | 8-methyl | 1-stearyloxycarbonyl | H | H | Cu | $ClO_4$ | 2 | 2 | 2 | 1 | 1 | 0 |
| 1-108 | ethyl | ethyl | 8-methyl | 1-phenoxycarbonyl | H | H | Cu | $ClO_4$ | 2 | 2 | 2 | 1 | 1 | 0 |
| 1-109 | ethyl | ethyl | 8-methyl | 1-p-tolyloxycarbonyl | H | H | Cu | $ClO_4$ | 2 | 2 | 2 | 1 | 1 | 0 |
| 1-110 | ethyl | ethyl | 8-methyl | 1-p-chlorophenoxycarbonyl | H | H | Cu | $ClO_4$ | 2 | 2 | 2 | 1 | 1 | 0 |
| 1-111 | ethyl | ethyl | 8-methyl | 1-p-methoxyphenocarbonyl | H | H | Cu | $ClO_4$ | 2 | 2 | 2 | 1 | 1 | 0 |
| 1-112 | ethyl | ethyl | 8-methyl | 1-nitro | H | H | Cu | $ClO_4$ | 2 | 2 | 2 | 1 | 1 | 0 |
| 1-113 | ethyl | ethyl | 8-methyl | 2-nitro | H | H | Cu | $ClO_4$ | 2 | 2 | 2 | 1 | 1 | 0 |
| 1-117 | ethyl | ethyl | 8-methyl | 1-chloro | H | H | Cu | $ClO_4$ | 2 | 2 | 2 | 1 | 1 | 0 |
| 1-118 | ethyl | ethyl | 8-methyl | 2-chloro | H | H | Cu | $ClO_4$ | 2 | 2 | 2 | 1 | 1 | 0 |
| 1-119 | ethyl | ethyl | 8-methyl | 2-bromo | H | H | Cu | $ClO_4$ | 2 | 2 | 2 | 1 | 1 | 0 |
| 1-120 | ethyl | ethyl | 8-methyl | 2-fluro | H | H | Cu | $ClO_4$ | 2 | 2 | 2 | 1 | 1 | 0 |
| 1-121 | ethyl | ethyl | 8-methyl | H | Ph | H | Cu | $ClO_4$ | 2 | 2 | 2 | 1 | 0 | 0 |

TABLE 7

| No. | R¹ | R² | R³ | R⁴ | R⁵ | R⁶ | M | X | i | j | k | l | m | n |
|---|---|---|---|---|---|---|---|---|---|---|---|---|---|---|
| 1-127 | ethyl | ethyl | 8-methyl | H | H | 3-chloro | Cu | ClO₄ | 2 | 2 | 2 | 1 | 0 | 1 |
| 1-128 | ethyl | ethyl | 8-methyl | H | H | 4-chloro | Cu | ClO₄ | 2 | 2 | 2 | 1 | 0 | 1 |
| 1-129 | ethyl | ethyl | 8-methyl | H | H | 5-chloro | Cu | ClO₄ | 2 | 2 | 2 | 1 | 0 | 1 |
| 1-130 | ethyl | ethyl | 8-methyl | H | H | 6-chloro | Cu | ClO₄ | 2 | 2 | 2 | 1 | 0 | 1 |
| 1-131 | ethyl | ethyl | 8-methyl | H | H | 4-fluro | Cu | ClO₄ | 2 | 2 | 2 | 1 | 0 | 1 |
| 1-133 | ethyl | ethyl | 8-methyl | H | H | 4-phenyl | Cu | ClO₄ | 2 | 2 | 2 | 1 | 0 | 1 |
| 1-139 | ethyl | ethyl | 8-methyl | H | H | 4-methoxyethoxy | Cu | ClO₄ | 2 | 2 | 2 | 1 | 0 | 2 |
| 1-140 | ethyl | ethyl | 8-methyl | H | H | 4-methoxycarbonyl | Cu | ClO₄ | 2 | 2 | 2 | 1 | 0 | 1 |
| 1-141 | ethyl | ethyl | 8-methyl | H | H | 5-ethoxycarbonyl | Cu | ClO₄ | 2 | 2 | 2 | 1 | 0 | 1 |
| 1-142 | ethyl | ethyl | 8-methyl | H | H | 6-cyano | Cu | ClO₄ | 2 | 2 | 2 | 1 | 0 | 1 |
| 1-143 | ethyl | ethyl | 8-methyl | H | H | 4-trifluoremethyl | Cu | ClO₄ | 2 | 2 | 2 | 1 | 0 | 1 |
| 1-144 | ethyl | ethyl | 8-methyl | H | H | 5-trifluoremethyl | Cu | ClO₄ | 2 | 2 | 2 | 1 | 0 | 1 |
| 1-146 | ethyl | ethyl | 8-methyl | H | H | 3-nitro | Cu | ClO₄ | 2 | 2 | 2 | 1 | 0 | 1 |
| 1-147 | ethyl | ethyl | 8-methyl | H | H | 5-nitro | Cu | ClO₄ | 2 | 2 | 2 | 1 | 0 | 1 |

TABLE 8

| No. | R¹ | R² | R³ | R⁴ | R⁵ | R⁶ | M | X | i | j | k | l | m | n |
|---|---|---|---|---|---|---|---|---|---|---|---|---|---|---|
| 1-148 | ethyl | ethyl | 8-methyl | H | H | 4-carboxyl | Cu | ClO₄ | 2 | 2 | 2 | 1 | 0 | 1 |
| 1-149 | ethyl | ethyl | 8-methyl | H | H | 6-carboxyl | Cu | ClO₄ | 2 | 2 | 2 | 1 | 0 | 1 |
| 1-150 | ethyl | ethyl | 8-methyl | H | H | 6-phenoxycarbonyl | Cu | ClO₄ | 2 | 2 | 2 | 1 | 0 | 1 |
| 1-151 | ethyl | ethyl | 8-methyl | H | H | 4-p-tolyloxycarbonyl | Cu | ClO₄ | 2 | 2 | 2 | 1 | 0 | 1 |
| 1-152 | ethyl | ethyl | 8-methyl | H | H | 6-o-bromophenoxycarbonyl | Cu | ClO₄ | 2 | 2 | 2 | 1 | 0 | 1 |
| 1-153 | ethyl | ethyl | 8-methyl | H | H | 4-acety | Cu | ClO₄ | 2 | 2 | 2 | 1 | 0 | 1 |
| 1-154 | ethyl | ethyl | 8-methyl | H | H | 4-propionyl | Cu | ClO₄ | 2 | 2 | 2 | 1 | 0 | 1 |
| 1-155 | ethyl | ethyl | 8-methyl | H | H | 4-isovaleryl | Cu | ClO₄ | 2 | 2 | 2 | 1 | 0 | 1 |
| 1-156 | ethyl | ethyl | 8-methyl | H | H | 4-stearoyl | Cu | ClO₄ | 2 | 2 | 2 | 1 | 0 | 1 |
| 1-157 | ethyl | ethyl | 8-methyl | H | H | 4-benzoyl | Cu | ClO₄ | 2 | 2 | 2 | 1 | 0 | 1 |
| 1-158 | ethyl | ethyl | 8-methyl | H | H | 4-N-phenylcarbamoyl | Cu | ClO₄ | 2 | 2 | 2 | 1 | 0 | 1 |
| 1-159 | ethyl | ethyl | 8-methyl | H | H | 6-N-methylcarbamoyl | Cu | ClO₄ | 2 | 2 | 2 | 1 | 0 | 1 |
| 1-160 | ethyl | ethyl | 8-methyl | H | H | 5-N-allylcarbamoyl | Cu | ClO₄ | 2 | 2 | 2 | 1 | 0 | 1 |
| 1-161 | ethyl | ethyl | 8-methyl | H | H | 4-(N-2-thienylcarbamoyl) | Cu | ClO₄ | 2 | 2 | 2 | 1 | 0 | 1 |
| 1-162 | ethyl | ethyl | 8-methyl | H | H | 4-N-benzothizolycarbamoyl | Cu | ClO₄ | 2 | 2 | 2 | 1 | 0 | 1 |
| 1-163 | ethyl | ethyl | 8-methyl | H | H | 4-(N-2-pyridylcarbamoyl) | Cu | ClO₄ | 2 | 2 | 2 | 1 | 0 | 1 |
| 1-164 | ethyl | ethyl | 8-methyl | H | H | 4-(N-3H-indo-2-lylcarbamoyl) | Cu | ClO₄ | 2 | 2 | 2 | 1 | 0 | 1 |
| 1-165 | ethyl | ethyl | 8-methyl | H | H | 4-N-phenylsulfamoyl | Cu | ClO₄ | 2 | 2 | 2 | 1 | 0 | 1 |
| 1-166 | ethyl | ethyl | 8-methyl | H | Me | 4-N-methylsulfamoyl | Cu | ClO₄ | 2 | 2 | 2 | 1 | 0 | 1 |
| 1-167 | ethyl | ethyl | 8-methyl | H | H | 6-(N-2-oxolanylmethysulfamoyl) | Cu | ClO₄ | 2 | 2 | 2 | 1 | 0 | 1 |
| 1-168 | ethyl | ethyl | 8-methyl | H | H | 4-(N-2-thiazolylsulfamoyl) | Cu | ClO₄ | 2 | 2 | 2 | 1 | 0 | 1 |

TABLE 9

| No. | R¹ | R² | R³ | R⁴ | R⁵ | R⁶ | M | X | i | j | k | l | m | n |
|---|---|---|---|---|---|---|---|---|---|---|---|---|---|---|
| 1-169 | ethyl | ethyl | 8-methyl | H | H | 4-N-benzoimidazolylsulfamoyl | Ni | ClO₄ | 2 | 2 | 2 | 1 | 0 | 1 |
| 1-170 | ethyl | ethyl | 8-methyl | H | H | 6-(N-2-pyrimidylsulfamoyl) | Fe | ClO₄ | 2 | 2 | 2 | 1 | 0 | 1 |
| 1-171 | ethyl | ethyl | 8-methyl | H | F | H | Cu | ClO₄ | 2 | 2 | 2 | 1 | 0 | 0 |
| 1-172 | ethyl | ethyl | 8-methyl | H | Cl | H | Cu | ClO₄ | 2 | 2 | 2 | 1 | 0 | 0 |
| 1-173 | ethyl | ethyl | 8-methyl | H | Br | H | Cu | ClO₄ | 2 | 2 | 2 | 1 | 0 | 0 |
| 1-176 | ethyl | ethyl | 8-methyl | H | cyano | H | Cu | ClO₄ | 2 | 2 | 2 | 1 | 0 | 0 |
| 1-179 | ethyl | ethyl | 8-methyl | H | o-hydroxyphenyl | H | Cu | ClO₄ | 2 | 2 | 2 | 1 | 0 | 0 |
| 1-180 | ethyl | ethyl | 8-methyl | H | 3-pyridinyl | H | Cu | ClO₄ | 2 | 2 | 2 | 1 | 0 | 0 |
| 1-183 | ethyl | ethyl | 8-methyl | H | ethoxy | H | Cu | ClO₄ | 2 | 2 | 2 | 1 | 0 | 0 |
| 1-188 | ethyl | ethyl | 8-methyl | H | formyl | H | Cu | ClO₄ | 2 | 2 | 2 | 1 | 0 | 0 |
| 1-189 | ethyl | ethyl | 8-methyl | H | acetyl | H | Cu | ClO₄ | 2 | 2 | 2 | 1 | 0 | 0 |

TABLE 10

| No. | R¹ | R² | R³ | R⁴ | R⁵ | R⁶ | M | X | i | j | k | l | m | n |
|---|---|---|---|---|---|---|---|---|---|---|---|---|---|---|
| 1-190 | 2-ethylhexyl | 2-ethylhexyl | H | H | hydroxyiminomethylcarbonyl | H | Cu | ClO₄ | 2 | 2 | 2 | 0 | 0 | 0 |
| 1-191 | 2-ethylhexyl | 2-ethylhexy | H | H | bromoyl | H | Cu | ClO₄ | 2 | 2 | 2 | 0 | 0 | 0 |
| 1-192 | 2-ethylhexyl | 2-ethylhexyl | H | H | hydroxycarbonyl | H | Cu | ClO₄ | 2 | 2 | 2 | 0 | 0 | 0 |
| 1-193 | 2-ethylhexyl | 2-ethylhexyl | H | H | methoxycarbonyl | H | Cu | ClO₄ | 2 | 2 | 2 | 0 | 0 | 0 |
| 1-194 | 2-ethylhexyl | 2-ethylhexyl | H | H | n-hexylcarbonyl | H | Cu | ClO₄ | 2 | 2 | 2 | 0 | 0 | 0 |
| 1-195 | 2-ethylhexyl | 2-ethylhexyl | H | H | aminothiocarbonyl | H | Cu | ClO₄ | 2 | 2 | 2 | 0 | 0 | 0 |

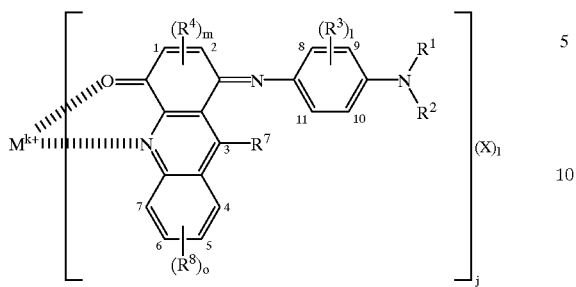
(2)

TABLE 11

| No. | R¹ | R² | R³ | R⁴ | R⁷ | R⁸ | M | X | i | j | k | l | m | o |
|---|---|---|---|---|---|---|---|---|---|---|---|---|---|---|
| 2-1 | ethyl | ethyl | 8-methyl | H | H | H | Cu | ClO₄ | 2 | 2 | 2 | 1 | 0 | 0 |
| 2-2 | ethyl | ethyl | H | H | H | H | Cu | ClO₄ | 2 | 2 | 2 | 0 | 0 | 0 |
| 2-3 | methyl | methyl | H | H | H | H | Cu | ClO₄ | 2 | 2 | 2 | 0 | 0 | 0 |
| 2-4 | n-propyl | n-propyl | H | H | H | H | Cu | ClO₄ | 2 | 2 | 2 | 0 | 0 | 0 |
| 2-5 | i-propyl | i-propyl | H | H | H | H | Cu | ClO₄ | 2 | 2 | 2 | 0 | 0 | 0 |
| 2-6 | n-butyl | n-butyl | H | H | H | H | Cu | ClO₄ | 2 | 2 | 2 | 0 | 0 | 0 |
| 2-7 | s-butyl | H | H | H | H | H | Cu | ClO₄ | 2 | 2 | 2 | 0 | 0 | 0 |
| 2-8 | n-pentyl | n-pentyl | H | H | H | H | Cu | ClO₄ | 2 | 2 | 2 | 0 | 0 | 0 |
| 2-9 | n-hexyl | n-hexyl | H | H | H | H | Cu | ClO₄ | 2 | 2 | 2 | 0 | 0 | 0 |
| 2-10 | 2-ethylhexyl | 2-ethylhexyl | H | H | H | H | Cu | ClO₄ | 2 | 2 | 2 | 0 | 0 | 0 |
| 2-11 | cetyl | cetyl | H | H | H | H | Cu | ClO₄ | 2 | 2 | 2 | 0 | 0 | 0 |
| 2-12 | ethyl | 2-cyanoethyl | H | H | H | H | Cu | ClO₄ | 2 | 2 | 2 | 0 | 0 | 0 |
| 2-13 | ethyl | 2-chloroethyl | H | H | H | H | Cu | ClO₄ | 2 | 2 | 2 | 0 | 0 | 0 |
| 2-14 | 2-ethoxyethyl | 2-ethoxyethyl | H | H | H | H | Cu | ClO₄ | 2 | 2 | 2 | 0 | 0 | 0 |
| 2-15 | methoxyethoxyethyl | methoxyethoxyethyl | H | H | H | H | Cu | ClO₄ | 2 | 2 | 2 | 0 | 0 | 0 |
| 2-16 | benzyl | benzyl | H | H | Ph | H | Cu | ClO₄ | 2 | 2 | 2 | 0 | 0 | 0 |
| 2-17 | ethyl | benzyloxyethyl | H | H | Ph | H | Cu | ClO₄ | 2 | 2 | 2 | 0 | 0 | 0 |
| 2-18 | ethyl | methylcarbonyloxyethyl | H | H | Ph | H | Cu | ClO₄ | 2 | 2 | 2 | 0 | 0 | 0 |
| 2-19 | ethyl | 2-phenoxyethyl | H | H | Ph | H | Cu | ClO₄ | 2 | 2 | 2 | 0 | 0 | 0 |
| 2-20 | ethyl | 2-acetoxyethyl | H | H | Ph | H | Cu | ClO₄ | 2 | 2 | 2 | 0 | 0 | 0 |
| 2-21 | 2-carboxyethyl | 2-carboxyethyl | H | H | H | H | Cu | ClO₄ | 2 | 2 | 2 | 0 | 0 | 0 |

TABLE 12

| No. | R¹ | R² | R³ | R⁴ | R⁷ | R⁸ | M | X | i | j | k | l | m | o |
|---|---|---|---|---|---|---|---|---|---|---|---|---|---|---|
| 2-22 | ethoxycarbonylmethyl | ethoxycarbonylmethyl | H | H | H | H | Cu | ClO₄ | 2 | 2 | 2 | 1 | 0 | 0 |
| 2-23 | 3-mesylpropyl | 3-mesylpropyl | H | H | H | H | Cu | ClO₄ | 2 | 2 | 2 | 0 | 0 | 0 |
| 2-24 | ethyl | 2-oxolanylmethyl | H | H | H | H | Cu | ClO₄ | 2 | 2 | 2 | 0 | 0 | 0 |
| 2-25 | H | phenyl | H | H | H | H | Cu | ClO₄ | 2 | 2 | 2 | 0 | 0 | 0 |
| 2-26 | H | p-tolyl | H | H | H | H | Cu | ClO₄ | 2 | 2 | 2 | 0 | 0 | 0 |
| 2-27 | H | p-chlorophenyl | H | H | H | H | Cu | ClO₄ | 2 | 2 | 2 | 0 | 0 | 0 |
| 2-28 | H | p-methoxyphenyl | H | H | H | H | Cu | ClO₄ | 2 | 2 | 2 | 0 | 0 | 0 |
| 2-29 | H | p-n-butoxyphenyl | H | H | H | H | Cu | ClO₄ | 2 | 2 | 2 | 0 | 0 | 0 |
| 2-30 | 2-propenyl | 2-propenyl | H | H | H | H | Cu | ClO₄ | 2 | 2 | 2 | 0 | 0 | 0 |
| 2-31 | ethyl | 2-methyl-2-propenyl | H | H | H | H | Cu | ClO₄ | 2 | 2 | 2 | 0 | 0 | 0 |
| 2-32 | ethyl | 2-chloro-2-propenyl | H | H | H | H | Cu | ClO₄ | 2 | 2 | 2 | 0 | 0 | 0 |
| 2-33 | ethyl | cyclohexyl | H | H | H | H | Cu | ClO₄ | 2 | 2 | 2 | 0 | 0 | 0 |
| 2-34 | piperidinyl | | H | H | H | H | Cu | ClO₄ | 2 | 2 | 2 | 0 | 0 | 0 |
| 2-35 | morpholinyl | | H | H | H | H | Cu | ClO₄ | 2 | 2 | 2 | 0 | 0 | 0 |
| 2-39 | ethyl | ethyl | 8-cyclohexyl | H | H | H | Cu | ClO₄ | 2 | 2 | 2 | 1 | 0 | 0 |
| 2-41 | ethyl | ethyl | 8-(2-propenyl) | H | H | H | Cu | ClO₄ | 2 | 2 | 2 | 1 | 0 | 0 |
| 2-42 | ethyl | ethyl | 8-benzyl | H | H | H | Cu | ClO₄ | 2 | 2 | 2 | 1 | 0 | 0 |

TABLE 13

| No. | R¹ | R² | R³ | R⁴ | R⁷ | R⁸ | M | X | i | j | k | l | m | o |
|---|---|---|---|---|---|---|---|---|---|---|---|---|---|---|
| 2-43 | ethyl | ethyl | 8-methoxy | H | H | H | Cu | ClO₄ | 2 | 2 | 2 | 1 | 0 | 0 |
| 2-44 | 2-phenoxyethyl | 2-phenoxyethyl | 8,10-diethoxy | H | H | H | Cu | ClO₄ | 2 | 2 | 2 | 2 | 0 | 0 |
| 2-45 | 2-ethoxyethyl | 2-ethoxyethyl | 8-methoxy-10-methyl | H | H | H | Cu | ClO₄ | 2 | 2 | 2 | 2 | 0 | 0 |

TABLE 13-continued

| No. | R¹ | R² | R³ | R⁴ | R⁷ | R⁸ | M | X | i | j | k | l | m | o |
|---|---|---|---|---|---|---|---|---|---|---|---|---|---|---|
| 2-49 | n-butyl | n-butyl | 8-diethylamino | H | H | H | Cu | ClO₄ | 2 | 2 | 2 | 1 | 0 | 0 |
| 2-50 | n-butyl | n-butyl | 8-diisopropylamino | H | H | H | Ni | ClO₄ | 2 | 2 | 2 | 1 | 0 | 0 |
| 2-51 | n-butyl | n-butyl | 8-tosylamino | H | H | H | Ni | ClO₄ | 2 | 2 | 2 | 1 | 0 | 0 |
| 2-52 | ethyl | ethyl | 8-mesylamino | H | H | H | Cu | ClO₄ | 2 | 2 | 2 | 1 | 0 | 0 |
| 2-53 | n-butyl | n-butyl | 8-laurolyamino | H | H | H | Cu | ClO₄ | 2 | 2 | 2 | 1 | 0 | 0 |
| 2-54 | ethyl | ethyl | 8-palmitoylamino | H | H | H | Ni | ClO₄ | 2 | 2 | 2 | 1 | 0 | 0 |
| 2-55 | ethyl | ethyl | 8-stearoylamino | H | H | H | Ni | ClO₄ | 2 | 2 | 2 | 1 | 0 | 0 |
| 2-56 | ethyl | ethyl | 8-(1-naphthoyl)amino | H | H | H | Ni | ClO₄ | 2 | 2 | 2 | 1 | 0 | 0 |
| 2-57 | 2-ethylhexyl | 2-ethylhexyl | H | H | H | H | Ni | ClO₄ | 2 | 2 | 2 | 0 | 0 | 0 |
| 2-58 | 2-ethylhexyl | 2-ethylhexyl | H | H | H | H | Fe | ClO₄ | 3 | 2 | 3 | 0 | 0 | 0 |
| 2-59 | ethyl | ethyl | 8-n-butylthio | H | H | H | Cu | ClO₄ | 2 | 2 | 2 | 1 | 0 | 0 |
| 2-60 | n-butyl | n-butyl | 8-phenylthio | H | H | H | Cu | Cl | 2 | 2 | 2 | 1 | 0 | 0 |
| 2-61 | ethyl | ethyl | 8-p-chlorophenylthio | H | H | H | Cu | Br | 2 | 2 | 2 | 1 | 0 | 0 |
| 2-62 | n-butyl | n-butyl | 8-benzylthio | H | H | H | Cu | I | 2 | 2 | 2 | 1 | 0 | 0 |
| 2-63 | ethyl | ethyl | 8-ureido | H | H | H | Cu | BF₄ | 2 | 2 | 2 | 1 | 0 | 0 |

TABLE 14

| No. | R¹ | R² | R³ | R⁴ | R⁷ | R⁸ | M | X | i | j | k | l | m | o |
|---|---|---|---|---|---|---|---|---|---|---|---|---|---|---|
| 2-64 | n-butyl | n-butyl | 8-N-n-propylureido | H | H | H | Cu | PF₆ | 2 | 2 | 2 | 1 | 0 | 0 |
| 2-65 | ethyl | ethyl | 8-N,N-diethylureido | H | H | H | Cu | ClO₄ | 2 | 2 | 2 | 1 | 0 | 0 |
| 2-66 | ethyl | ethyl | 8-thioureido | H | H | H | Cu | ClO₄ | 2 | 2 | 2 | 1 | 0 | 0 |
| 2-67 | ethyl | ethyl | 8-N-acetyl-N-phenylthioureido | H | H | H | Cu | SbF₆ | 2 | 2 | 2 | 1 | 0 | 0 |
| 2-68 | ethyl | ethyl | 8-methyl | 1-acetyl | H | H | Cu | ClO₄ | 2 | 3 | 2 | 1 | 1 | 0 |
| 2-69 | ethyl | ethyl | 8-methyl | 1-isovaleryl | H | H | Cu | ClO₄ | 2 | 3 | 2 | 1 | 1 | 0 |
| 2-70 | ethyl | ethyl | 8-methyl | 1-stearoyl | H | H | Cu | ClO₄ | 2 | 3 | 2 | 1 | 1 | 0 |
| 2-71 | ethyl | ethyl | 8-methyl | 1-benzoyl | H | H | Cu | ClO₄ | 2 | 3 | 2 | 1 | 1 | 0 |
| 2-72 | ethyl | ethyl | 8-methyl | 1-(1-naphthoyl) | H | H | Cu | ClO₄ | 2 | 3 | 2 | 1 | 1 | 0 |
| 2-73 | ethyl | ethyl | 8-methyl | 1-carboxy | H | H | Cu | ClO₄ | 2 | 2 | 2 | 1 | 1 | 0 |
| 2-74 | ethyl | ethyl | 8-methyl | 1-N-phenylcarbamoyl | H | H | Cu | ClO₄ | 2 | 2 | 2 | 1 | 1 | 0 |
| 2-75 | ethyl | ethyl | 8-methyl | 1-N-methylcarbamoyl | H | H | Cu | ClO₄ | 2 | 2 | 2 | 1 | 1 | 0 |
| 2-76 | ethyl | ethyl | 8-methyl | 1-N-ethoxy-methylcarbamoyl | H | H | Cu | ClO₄ | 2 | 2 | 2 | 1 | 1 | 0 |
| 2-77 | ethyl | ethyl | 8-methyl | 1-N-2-oxolanyl-methylcarbamoyl) | H | H | Cu | ClO₄ | 2 | 2 | 2 | 1 | 1 | 0 |
| 2-78 | ethyl | ethyl | 8-methyl | 1-N-allylcarbamoyl | H | H | Cu | ClO₄ | 2 | 2 | 2 | 1 | 1 | 0 |
| 2-79 | ethyl | ethyl | 8-methyl | 1-N-3-(2-methoxycarbonyl)thienylcarbamoyl | H | H | Cu | ClO₄ | 2 | 2 | 2 | 1 | 1 | 0 |
| 2-80 | ethyl | ethyl | 8-methyl | 1-N-2-thiazolylcarbamoyl | H | H | Cu | ClO₄ | 2 | 2 | 2 | 1 | 1 | 0 |
| 2-81 | ethyl | ethyl | 8-methyl | 1-(N-2-benzoimidazolyl-carbamoyl) | H | H | Cu | ClO₄ | 2 | 2 | 2 | 1 | 1 | 0 |
| 2-82 | ethyl | ethyl | 8-methyl | 1-(N-2-benzoxazolylcarbamoyl) | H | H | Cu | ClO₄ | 2 | 2 | 2 | 1 | 1 | 0 |
| 2-83 | ethyl | ethyl | 8-methyl | 1-(N-2-benzothioazolyl carbamoyl) | H | H | Cu | ClO₄ | 2 | 2 | 2 | 1 | 1 | 0 |
| 2-84 | ethyl | ethyl | 8-methyl | 1-(N-2-pyridylcarbamoyl) | H | H | Cu | ClO₄ | 2 | 2 | 2 | 1 | 1 | 0 |

TABLE 15

| No. | R¹ | R² | R³ | R⁴ | R⁷ | R⁸ | M | X | i | j | k | l | m | o |
|---|---|---|---|---|---|---|---|---|---|---|---|---|---|---|
| 2-85 | ethyl | ethyl | 8-methyl | 1-(N-4-pyrimidylcarbamoyl) | H | H | Cu | ClO₄ | 2 | 2 | 2 | 1 | 1 | 0 |
| 2-86 | ethyl | ethyl | 8-methyl | 1-(N-2-quinolylcarbamoyl) | H | H | Cu | ClO₄ | 2 | 2 | 2 | 1 | 1 | 0 |
| 2-87 | ethyl | ethyl | 8-methyl | 1-(N-3H-indo-2-lylcarbamoyl) | H | H | Cu | ClO₄ | 2 | 2 | 2 | 1 | 1 | 0 |
| 2-88 | ethyl | ethyl | 8-methyl | 1-sulfo | H | H | Cu | ClO₄ | 2 | 2 | 2 | 1 | 1 | 0 |
| 2-89 | ethyl | ethyl | 8-methyl | 1-N-phenylsulfamoyl | H | H | Cu | ClO₄ | 2 | 2 | 2 | 1 | 1 | 0 |
| 2-90 | ethyl | ethyl | 8-methyl | 1-N-methylsulfamoyl | H | H | Cu | ClO₄ | 2 | 2 | 2 | 1 | 1 | 0 |
| 2-91 | ethyl | ethyl | 8-methyl | 1-N-ethoxymethylsulfamoyl | H | H | Cu | ClO₄ | 2 | 2 | 2 | 1 | 1 | 0 |
| 2-92 | ethyl | ethyl | 8-methyl | 1-(N-2-oxolanylmethyl-sulfamoyl) | H | H | Cu | ClO₄ | 2 | 2 | 2 | 1 | 1 | 0 |
| 2-93 | ethyl | ethyl | 8-methyl | 1-N-allylsulfamoyl- | H | H | Cu | ClO₄ | 2 | 2 | 2 | 1 | 1 | 0 |
| 2-94 | ethyl | ethyl | 8-methyl | 1-(N-2-thienylsulfamoyl) | H | H | Cu | ClO₄ | 2 | 2 | 2 | 1 | 1 | 0 |
| 2-95 | ethyl | ethyl | 8-methyl | 1-(N-2-thiazolylsulfamoyl) | H | H | Cu | ClO₄ | 2 | 2 | 2 | 1 | 1 | 0 |
| 2-96 | ethyl | ethyl | 8-methyl | 1-(N-2-benzoimidazolyl-sulfamoyl) | H | H | Cu | ClO₄ | 2 | 2 | 2 | 1 | 1 | 0 |
| 2-97 | ethyl | ethyl | 8-methyl | 1-(N-2-benzoxazolylsulfamoyl) | H | H | Cu | ClO₄ | 2 | 2 | 2 | 1 | 1 | 0 |
| 2-98 | ethyl | ethyl | 8-methyl | 1-(N-2-benzothiazolylsulfamoyl) | H | H | Cu | ClO₄ | 2 | 2 | 2 | 1 | 1 | 0 |
| 2-99 | ethyl | ethyl | 8-methyl | 1-(N-2-pyridylsulfamoyl) | H | H | Cu | ClO₄ | 2 | 2 | 2 | 1 | 1 | 0 |
| 2-100 | ethyl | ethyl | 8-methyl | 1-(N-4-pyrimidylsulfamoyl) | H | H | Cu | ClO₄ | 2 | 2 | 2 | 1 | 1 | 0 |
| 2-101 | ethyl | ethyl | 8-methyl | 1-(N-2-quinolylsulfamoyl) | H | H | Cu | ClO₄ | 2 | 2 | 2 | 1 | 1 | 0 |

TABLE 15-continued

| No. | R¹ | R² | R³ | R⁴ | R⁷ | R⁸ | M | X | i | j | k | l | m | o |
|---|---|---|---|---|---|---|---|---|---|---|---|---|---|---|
| 2-102 | ethyl | ethyl | 8-methyl | 1-(N-3H-imido-2-lylsulfamoyl) | H | H | Cu | ClO₄ | 2 | 2 | 2 | 1 | 1 | 0 |
| 2-103 | ethyl | ethyl | 8-methyl | 1-methoxycarbonyl | H | H | Cu | ClO₄ | 2 | 2 | 2 | 1 | 1 | 0 |
| 2-104 | ethyl | ethyl | 8-methyl | 1-ethoxycarbonyl | H | H | Cu | ClO₄ | 2 | 2 | 2 | 1 | 1 | 0 |
| 2-105 | ethyl | ethyl | 8-methyl | 1-n-butoxycarbonyl | H | H | Cu | ClO₄ | 2 | 2 | 2 | 1 | 1 | 0 |

TABLE 16

| No. | R¹ | R² | R³ | R⁴ | R⁷ | R⁸ | M | X | i | j | k | l | m | o |
|---|---|---|---|---|---|---|---|---|---|---|---|---|---|---|
| 2-106 | ethyl | ethyl | 8-methyl | 1-lauryloxycarbonyl | H | H | Cu | ClO₄ | 2 | 2 | 2 | 1 | 1 | 0 |
| 2-107 | ethyl | ethyl | 8-methyl | 1-stearyloxycarbonyl | H | H | Cu | ClO₄ | 2 | 2 | 2 | 1 | 1 | 0 |
| 2-108 | ethyl | ethyl | 8-methyl | 1-phenoxycarbonyl | H | H | Cu | ClO₄ | 2 | 2 | 2 | 1 | 1 | 0 |
| 2-109 | ethyl | ethyl | 8-methyl | 1-p-tolyloxycarbonyl | H | H | Cu | ClO₄ | 2 | 2 | 2 | 1 | 1 | 0 |
| 2-110 | ethyl | ethyl | 8-methyl | 1-p-chlorophenoxycarbonyl | H | H | Cu | ClO₄ | 2 | 2 | 2 | 1 | 1 | 0 |
| 2-111 | ethyl | ethyl | 8-methyl | 1-p-methoxyphenocarbonyl | H | H | Cu | ClO₄ | 2 | 2 | 2 | 1 | 1 | 0 |
| 2-112 | ethyl | ethyl | 8-methyl | 1-nitro | H | H | Cu | ClO₄ | 2 | 2 | 2 | 1 | 1 | 0 |
| 2-113 | ethyl | ethyl | 8-methyl | 2-nitro | H | H | Cu | ClO₄ | 2 | 2 | 2 | 1 | 1 | 0 |
| 2-114 | ethyl | ethyl | 8-methyl | 2-methyl | H | H | Cu | ClO₄ | 2 | 2 | 2 | 1 | 1 | 0 |
| 2-117 | ethyl | ethyl | 8-methyl | 1-chloro | H | H | Cu | ClO₄ | 2 | 2 | 2 | 1 | 1 | 0 |
| 2-118 | ethyl | ethyl | 8-methyl | 2-chloro | H | H | Cu | ClO₄ | 2 | 2 | 2 | 1 | 1 | 0 |
| 2-119 | ethyl | ethyl | 8-methyl | 2-bromo | H | H | Cu | ClO₄ | 2 | 2 | 2 | 1 | 1 | 0 |
| 2-120 | ethyl | ethyl | 8-methyl | 2-fluoro | H | H | Cu | ClO₄ | 2 | 2 | 2 | 1 | 1 | 0 |
| 2-121 | ethyl | ethyl | 8-methyl | H | Ph | H | Cu | ClO₄ | 2 | 2 | 2 | 1 | 0 | 0 |

TABLE 17

| No | R¹ | R² | R³ | R⁴ | R⁷ | R⁸ | M | X | i | j | k | l | m | o |
|---|---|---|---|---|---|---|---|---|---|---|---|---|---|---|
| 2-128 | ethyl | ethyl | 8-methyl | H | H | 4-chloro | Cu | ClO₄ | 2 | 2 | 2 | 1 | 0 | 1 |
| 2-129 | ethyl | ethyl | 8-methyl | H | H | 5-chloro | Cu | ClO₄ | 2 | 2 | 2 | 1 | 0 | 1 |
| 2-130 | ethyl | ethyl | 8-methyl | H | H | 6-chloro | Cu | ClO₄ | 2 | 2 | 2 | 1 | 0 | 1 |
| 2-131 | ethyl | ethyl | 8-methyl | H | H | 4-fluoro | Cu | ClO₄ | 2 | 2 | 2 | 1 | 0 | 1 |
| 2-133 | ethyl | ethyl | 8-methyl | H | H | 4-phenyl | Cu | ClO₄ | 2 | 2 | 2 | 1 | 0 | 1 |
| 2-140 | ethyl | ethyl | 8-methyl | H | H | 4-methoxycarbonyl | Cu | ClO₄ | 2 | 2 | 2 | 1 | 0 | 1 |
| 2-141 | ethyl | ethyl | 8-methyl | H | H | 5-ethoxycarbonyl | Cu | ClO₄ | 2 | 2 | 2 | 1 | 0 | 1 |
| 2-142 | ethyl | ethyl | 8-methyl | H | H | 6-cyano | Cu | ClO₄ | 2 | 2 | 2 | 1 | 0 | 1 |
| 2-143 | ethyl | ethyl | 8-methyl | H | H | 4-trifluoremethyl | Cu | ClO₄ | 2 | 2 | 2 | 1 | 0 | 1 |
| 2-144 | ethyl | ethyl | 8-methyl | H | H | 5-trifluoremethyl | Cu | ClO₄ | 2 | 2 | 2 | 1 | 0 | 1 |
| 2-147 | ethyl | ethyl | 8-methyl | H | H | 5-nitro | Cu | ClO₄ | 2 | 2 | 2 | 1 | 0 | 1 |

TABLE 18

| No. | R¹ | R² | R³ | R⁴ | R⁷ | R⁸ | M | X | i | j | k | l | m | o |
|---|---|---|---|---|---|---|---|---|---|---|---|---|---|---|
| 2-148 | ethyl | ethyl | 3-methyl | H | H | 4-carboxyl | Cu | ClO₄ | 2 | 2 | 2 | 1 | 0 | 1 |
| 2-149 | ethyl | ethyl | 8-methyl | H | H | 6-carboxyl | Cu | ClO₄ | 2 | 2 | 2 | 1 | 0 | 1 |
| 2-150 | ethyl | ethyl | 8-methyl | H | H | 6-phenoxycarbonyl | Cu | ClO₄ | 2 | 2 | 2 | 1 | 0 | 1 |
| 2-151 | ethyl | ethyl | 8-methyl | H | H | 4-p-tolyloxycarbonyl | Cu | ClO₄ | 2 | 2 | 2 | 1 | 0 | 1 |
| 2-152 | ethyl | ethyl | 8-methyl | H | H | 6-o-bromophenoxycarbonyl | Cu | ClO₄ | 2 | 2 | 2 | 1 | 0 | 1 |
| 2-153 | ethyl | ethyl | 8-methyl | H | H | 6-acetly | Cu | ClO₄ | 2 | 2 | 2 | 1 | 0 | 1 |
| 2-154 | ethyl | ethyl | 8-methyl | H | H | 6-propionyl | Cu | ClO₄ | 2 | 2 | 2 | 1 | 0 | 1 |
| 2-155 | ethyl | ethyl | 8-methyl | H | H | 6-isovaleryl | Cu | ClO₄ | 2 | 2 | 2 | 1 | 0 | 1 |
| 2-156 | ethyl | ethyl | 8-methyl | H | H | 6-stearoyl | Cu | ClO₄ | 2 | 2 | 2 | 1 | 0 | 1 |
| 2-157 | ethyl | ethyl | 8-methyl | H | H | 6-benzoyl | Cu | ClO₄ | 2 | 2 | 2 | 1 | 0 | 1 |
| 2-158 | ethyl | ethyl | 8-methyl | H | H | 4-N-phenylcarbamoyl | Cu | ClO₄ | 2 | 2 | 2 | 1 | 0 | 1 |
| 2-159 | ethyl | ethyl | 8-methyl | H | H | 6-N-methylcarbamoyl | Cu | ClO₄ | 2 | 2 | 2 | 1 | 0 | 1 |
| 2-160 | ethyl | ethyl | 8-methyl | H | H | 5-N-allylcarbamoyl | Cu | ClO₄ | 2 | 2 | 2 | 1 | 0 | 1 |
| 2-161 | ethyl | ethyl | 8-methyl | H | H | 4-N-2-thienylcarbamoyl) | Cu | ClO₄ | 2 | 2 | 2 | 1 | 0 | 1 |
| 2-162 | ethyl | ethyl | 8-methyl | H | H | 4-N-benzothiazolylcarbamoyl | Cu | ClO₄ | 2 | 2 | 2 | 1 | 0 | 1 |
| 2-163 | ethyl | ethyl | 8-methyl | H | H | 4-(N-2-pyridylcarbamoyl) | Cu | ClO₄ | 2 | 2 | 2 | 1 | 0 | 1 |
| 2-164 | ethyl | ethyl | 8-methyl | H | H | 4-(N-3H-indo-2-lylcarbamoyl) | Cu | ClO₄ | 2 | 2 | 2 | 1 | 0 | 1 |
| 2-165 | ethyl | ethyl | 8-methyl | H | H | 4-N-phenylsulfamoyl | Cu | ClO₄ | 2 | 2 | 2 | 1 | 0 | 1 |
| 2-166 | ethyl | ethyl | 8-methyl | H | H | 4-N-methylsulfamoyl | Cu | ClO₄ | 2 | 2 | 2 | 1 | 0 | 1 |
| 2-167 | ethyl | ethyl | 8-methyl | H | H | 6-(N-2-oxolanylmethylsulfamoyl) | Cu | ClO₄ | 2 | 2 | 2 | 1 | 0 | 1 |
| 2-168 | ethyl | ethyl | 8-methyl | H | H | 4-(N-2-thiazolylsulfamoyl) | Cu | ClO₄ | 2 | 2 | 2 | 1 | 0 | 1 |

TABLE 19

| No. | $R^1$ | $R^2$ | $R^3$ | $R^4$ | $R^7$ | $R^8$ | M | X | i | j | k | l | m | o |
|---|---|---|---|---|---|---|---|---|---|---|---|---|---|---|
| 2-169 | ethyl | ethyl | 8-methyl | H | H | 4-N-benzoimidazolylsulfamoyl | Ni | $ClO_4$ | 2 | 2 | 2 | 1 | 0 | 1 |
| 2-170 | ethyl | ethyl | 8-methyl | H | H | 6-(N-2-pyrimidylsulfamoyl) | Fe | $ClO_4$ | 2 | 2 | 2 | 1 | 0 | 1 |
| 2-171 | ethyl | ethyl | 8-methyl | H | F | H | Cu | $ClO_4$ | 2 | 2 | 2 | 1 | 0 | 0 |
| 2-172 | ethyl | ethyl | 8-methyl | H | Cl | H | Cu | $ClO_4$ | 2 | 2 | 2 | 1 | 0 | 0 |
| 2-173 | ethyl | ethyl | 8-methyl | H | Br | H | Cu | $ClO_4$ | 2 | 2 | 2 | 1 | 0 | 0 |
| 2-176 | ethyl | ethyl | 8-methyl | H | cyano | H | Cu | $ClO_4$ | 2 | 2 | 2 | 1 | 0 | 0 |
| 2-179 | ethyl | ethyl | 8-methyl | H | o-hydroxyphenyl | H | Cu | $ClO_4$ | 2 | 2 | 2 | 1 | 0 | 0 |
| 2-180 | ethyl | ethyl | 8-methyl | H | 3-pyridinyl | H | Cu | $ClO_4$ | 2 | 2 | 2 | 1 | 0 | 0 |
| 2-188 | ethyl | ethyl | 8-methyl | H | formyl | H | Cu | $ClO_4$ | 2 | 2 | 2 | 1 | 0 | 0 |
| 2-189 | ethyl | ethyl | 8-methyl | H | acetyl | H | Cu | $ClO_4$ | 2 | 2 | 2 | 1 | 0 | 0 |

TABLE 20

| No. | $R^1$ | $R^2$ | $R^3$ | $R^4$ | $R^5$ | $R^6$ | M | X | i | j | k | l | m | n |
|---|---|---|---|---|---|---|---|---|---|---|---|---|---|---|
| 2-190 | 2-ethylhexyl | 2-ethylhexyl | H | H | hydroxyiminomethylcarbonyl | H | Cu | $ClO_4$ | 2 | 2 | 2 | 0 | 0 | 0 |
| 2-191 | 2-ethylhexyl | 2-ethylhexyl | H | H | bromolacetyl | H | Cu | $ClO_4$ | 2 | 2 | 2 | 0 | 0 | 0 |
| 2-192 | 2-ethylhexyl | 2-ethylhexyl | H | H | hydroxycarbonyl | H | Cu | $ClO_4$ | 2 | 2 | 2 | 0 | 0 | 0 |
| 2-193 | 2-ethylhexyl | 2-ethylhexyl | H | H | methoxycarbonyl | H | Cu | $ClO_4$ | 2 | 2 | 2 | 0 | 0 | 0 |
| 2-194 | 2-ethylhexyl | 2-ethylhexyl | H | H | n-hexylcarbonyl | H | Cu | $ClO_4$ | 2 | 2 | 2 | 0 | 0 | 0 |
| 2-195 | 2-ethylhexyl | 2-ethylhexyl | H | H | aminothiocarbonyl | H | Cu | $ClO_4$ | 2 | 2 | 2 | 0 | 0 | 0 |

Next, the process for producing new indoaniline metal complexes according to the present invention will be described. The new indoaniline metal complexes represented by the general formula (1) or (2) can be synthesized by modifying the method described in Japanese Laid-Open (ko-kai) No. 227569/1988. That is, for 4-hydroxyphenanthridine derivative represented by the following general formula (6)

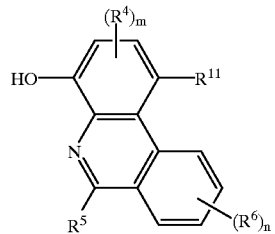

(6)

(in the formula, $R^4$, $R^5$, $R^6$, m and n are the same as those of the above definitions, whereas $R^{10}$ denotes a hydrogen atom or halogen atom) or 4-hydroxyacridine derivative represented by the following general formula (7):

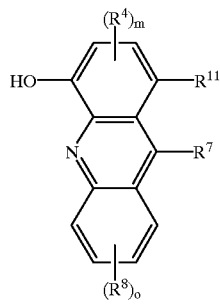

(7)

(in the formula, $R^4$, $R^7$, $R^8$, m and n are the same as those of the above definitions, whereas $R^{11}$ denotes a hydrogen atom and halogen atom), an addition reaction of a p-N,N-substituted amino aniline compound represented by the following general formula (8):

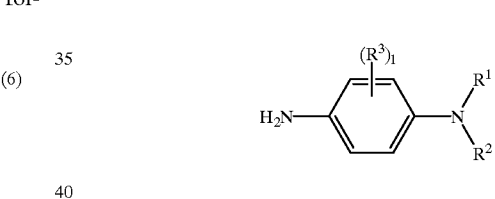

(8)

(in the formula, $R^1$, $R^2$, $R^3$ and l are the same as those of the above definitions) or its chloride, sulfate, nitrate or organic acid salt is carried out by using an oxidizing agent and a new indoaniline derivative represented by the following general formula (3):

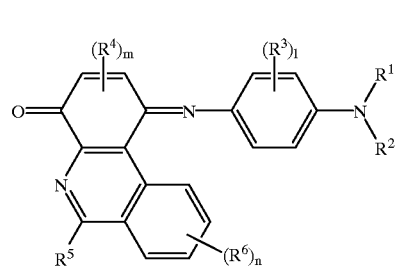

(3)

(in the formula, $R^1$, $R^2$, $R^3$, $R^4$, $R^5$, $R^6$, l, m and n are the same as those of the above definitions) and a new indoaniline derivative represented by the following general formula (4):

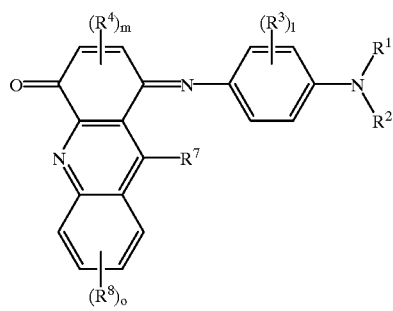

(4)

(in the formula, $R^1$, $R^2$, $R^3$, $R^4$, $R^7$, $R^8$, l, m and o are the same as those of the above definitions) can be obtained. Then, chelate reaction with the indoaniline derivative represented by the general formula (3) or (4) mentioned above is carried out by using a metal salt represented by the following general formula (9):

$$M^{r+}(X)_s \cdot t(H_2O) \qquad (9)$$

(in the formula, M and X are the same as those of the above definitions, whereas r–s denote an integer of 1–3 and t denotes an integer of 0–20), so that a new indoaniline metal complex represented by the general formula (1) or (2) can be prepared.

Specifically, a new indoaniline derivative represented by the general formulae (3) and (4) and a metal salt represented by the general formula (9) are allowed to react at temperatures of 0° C. to 100° C., preferably 0° C. to 40° C., for a period of 10 min to 24 hr in water and a solvent such as methanol, ethanol, isopropanol, acetone, methylethylketone, dioxane and tetrahydrofuran, preferably water and an alcohol solvent such as methanol and ethanol. After the completion of the reaction, the precipitated crystal is filtered out, cleaned with water and an alcohol solvent such as methanol or ethanol and air-dried and under reduced pressure, so that a new indoaniline metal complex represented by the general formula (1) or (2) can be obtained.

Hereinafter, specific examples of new indoaniline derivatives represented by the following general formula (3) or (4) will be mentioned but the present invention is not limited to these examples. In the tables that follow, l, m, n, and o are indicated as 0 (zero) where the appropriate R group is a hydrogen atom, i.e., l, m, n, and o are technically 1 (one).

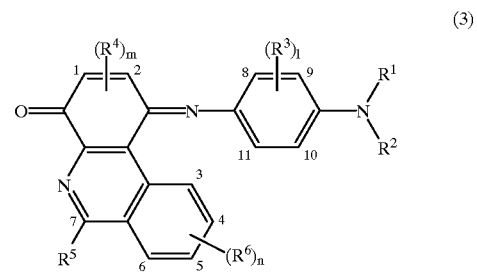

(3)

TABLE 21

| No. | $R^1$ | $R^2$ | $R^3$ | $R^4$ | $R^5$ | $R^6$ | l | m | o |
|---|---|---|---|---|---|---|---|---|---|
| 3-1 | ethyl | ethyl | 8-methyl | H | H | H | 1 | 0 | 0 |
| 3-2 | ethyl | ethyl | H | H | H | H | 0 | 0 | 0 |
| 3-3 | methyl | methyl | H | H | H | H | 0 | 0 | 0 |
| 3-4 | n-propyl | n-propyl | H | H | H | H | 0 | 0 | 0 |
| 3-5 | i-propyl | i-propyl | H | H | H | H | 0 | 0 | 0 |
| 3-6 | n-butyl | n-butyl | H | H | H | H | 0 | 0 | 0 |
| 3-7 | s-butyl | H | H | H | H | H | 0 | 0 | 0 |
| 3-8 | n-pentyl | n-pentyl | H | H | H | H | 0 | 0 | 0 |
| 3-9 | n-hexyl | n-hexyl | H | H | H | H | 0 | 0 | 0 |
| 3-10 | 2-ethylhexyl | 2-ethylhexyl | H | H | H | H | 0 | 0 | 0 |
| 3-11 | cetyl | cetyl | H | H | H | H | 0 | 0 | 0 |
| 3-12 | ethyl | 2-cyanoethyl | H | H | H | H | 0 | 0 | 0 |
| 3-13 | ethyl | 2-chloroethyl | H | H | H | H | 0 | 0 | 0 |
| 3-14 | 2-ethoxyethyl | 2-ethoxyethyl | H | H | H | H | 0 | 0 | 0 |
| 3-15 | methoxy-ethoxyethyl | methoxyethoxy ethyl | H | H | H | H | 0 | 0 | 0 |
| 3-16 | benzyl | benzyl | H | H | Ph | H | 0 | 0 | 0 |
| 3-17 | ethyl | benzyloxyethyl | H | H | Ph | H | 0 | 0 | 0 |
| 3-18 | ethyl | methylcarbonyl oxyethyl | H | H | Ph | H | 0 | 0 | 0 |
| 3-19 | ethyl | 2-phenoxyethyl | H | H | Ph | H | 0 | 0 | 0 |
| 3-20 | ethyl | 2-acetoxyethyl | H | H | Ph | H | 0 | 0 | 0 |
| 3-21 | 2-carboxyethyl | 2-carboxyethyl | H | H | H | H | 0 | 0 | 0 |

TABLE 22

| No. | $R^1$ | $R^2$ | $R^3$ | $R^4$ | $R^5$ | $R^6$ | l | m | o |
|---|---|---|---|---|---|---|---|---|---|
| 3-22 | ethoxycarbonylmethyl | ethoxycarbonylmethyl | H | H | H | H | 0 | 0 | 0 |
| 3-23 | 3-mesylpropyl | 3-mesylpropyl | H | H | H | H | 0 | 0 | 0 |
| 3-24 | ethyl | 2-oxolanylmethyl | H | H | H | H | 0 | 0 | 0 |
| 3-25 | H | phenyl | H | H | H | H | 0 | 0 | 0 |
| 3-26 | H | p-tolyl | H | H | H | H | 0 | 0 | 0 |

TABLE 22-continued

| No. | R¹ | R² | R³ | R⁴ | R⁵ | R⁶ | l | m | o |
|---|---|---|---|---|---|---|---|---|---|
| 3-27 | H | p-chlorophenyl | H | H | H | H | 0 | 0 | 0 |
| 3-28 | H | p-methoxyphenyl | H | H | H | H | 0 | 0 | 0 |
| 3-29 | H | p-n-butoxyphenyl | H | H | H | H | 0 | 0 | 0 |
| 3-30 | 2-propenyl | 2-propenyl | H | H | H | H | 0 | 0 | 0 |
| 3-31 | ethyl | 2-methyl-2-propenyl | H | H | H | H | 0 | 0 | 0 |
| 3-32 | ethyl | 2-chloro-2-propenyl | H | H | H | H | 0 | 0 | 0 |
| 3-33 | ethyl | cyclohexyl | H | H | H | H | 0 | 0 | 0 |
| 3-34 | piperidinyl | | H | H | H | H | 0 | 0 | 0 |
| 3-35 | morpbolinyl | | H | H | H | H | 0 | 0 | 0 |
| 3-38 | ethyl | ethyl | 8-ethyl | H | H | H | 1 | 0 | 0 |
| 3-39 | ethyl | ethyl | 8-cyclohexyl | H | H | H | 1 | 0 | 0 |
| 3-41 | ethyl | ethyl | 8-(2-propenyl) | H | H | H | 1 | 0 | 0 |
| 3-42 | ethyl | ethyl | 8-benzyl | H | H | H | 1 | 0 | 0 |

TABLE 23

| No. | R¹ | R² | R³ | R⁴ | R⁵ | R⁶ | l | m | o |
|---|---|---|---|---|---|---|---|---|---|
| 3-43 | ethyl | ethyl | 8-methoxy | H | H | H | 1 | 0 | 0 |
| 3-44 | 2-phenoxyethyl | 2-phenoxyethyl | 8,10-diethoxy | H | H | H | 2 | 0 | 0 |
| 3-45 | 2-ethoxyethyl | 2-ethoxyethyl | 8-methoxy-10-methyl | H | H | H | 2 | 0 | 0 |
| 3-49 | n-butyl | n-butyl | 8-diethylamino | H | H | H | 1 | 0 | 0 |
| 3-50 | n-butyl | n-butyl | 8-diisopropylamino | H | H | H | 1 | 0 | 0 |
| 3-51 | n-butyl | n-butyl | 8-tosylamino | H | H | H | 1 | 0 | 0 |
| 3-52 | ethyl | ethyl | 8-mesylamino | H | H | H | 1 | 0 | 0 |
| 3-53 | n-butyl | n-butyl | 8-laurloyamino | H | H | H | 1 | 0 | 0 |
| 3-54 | ethyl | ethyl | 8-palmitoylamino | H | H | H | 1 | 0 | 0 |
| 3-55 | ethyl | ethyl | 8-stearoylamino | H | H | H | 1 | 0 | 0 |
| 3-56 | ethyl | ethyl | 8-(1-naphtoyl)amino | H | H | H | 1 | 0 | 0 |
| 3-59 | ethyl | ethyl | 8-n-butylthio | H | H | H | 1 | 0 | 0 |
| 3-60 | n-butyl | n-butyl | 8-phenylthio | H | H | H | 1 | 0 | 0 |
| 3-61 | ethyl | ethyl | 8-p-chlorophenylthio | H | H | H | 1 | 0 | 0 |
| 3-62 | n-butyl | n-butyl | 8-benzylthio | H | H | H | 1 | 0 | 0 |
| 3-63 | ethyl | ethyl | 8-ureido | H | H | H | 1 | 0 | 0 |

TABLE 24

| No. | R¹ | R² | R³ | R⁴ | R⁵ | R⁶ | l | m | o |
|---|---|---|---|---|---|---|---|---|---|
| 3-64 | n-butyl | n-butyl | 8-N-n-propylureido | H | H | H | 1 | 0 | 0 |
| 3-65 | ethyl | ethyl | 8-N,N-diethylureido | H | H | H | 1 | 0 | 0 |
| 3-66 | ethyl | ethyl | 8-thioreido | H | H | H | 1 | 0 | 0 |
| 3-67 | ethyl | ethyl | 8-N-acetyl-N-phenylthioureido | H | H | H | 1 | 0 | 0 |

TABLE 25

| No. | R¹ | R² | R³ | R⁴ | R⁵ | R⁶ | l | m | o |
|---|---|---|---|---|---|---|---|---|---|
| 3-85 | ethyl | ethyl | 8-methyl | 1-(N-2-pyrimidylcarbamoyl) | H | H | 1 | 1 | 0 |
| 3-86 | ethyl | ethyl | 8-methyl | 1-(N-2-quinolylcarbamoyl) | H | H | 1 | 1 | 0 |
| 3-87 | ethyl | ethyl | 8-methyl | 1-(N-3H-indo-2-lylcarbamoyl) | H | H | 1 | 1 | 0 |
| 3-88 | ethyl | ethyl | 8-methyl | 1-sulfo | H | H | 1 | 1 | 0 |
| 3-89 | ethyl | ethyl | 8-methyl | 1-N-phenylsulfamoyl | H | H | 1 | 1 | 0 |
| 3-90 | ethyl | ethyl | 8-methyl | 1-N-methylsulfamoyl | H | H | 1 | 1 | 0 |
| 3-91 | ethyl | ethyl | 8-methyl | 1-N-ethoxymethylsulfamoyl | H | H | 1 | 1 | 0 |
| 3-92 | ethyl | ethyl | 8-methyl | 1-(N-2-oxolanylmethylsulfamoyl) | H | H | 1 | 1 | 0 |
| 3-93 | ethyl | ethyl | 8-methyl | 1-N-allylsulfamoyl | H | H | 1 | 1 | 0 |
| 3-94 | ethyl | ethyl | 8-methyl | 1-(N-2-thienylsulfamoyl) | H | H | 1 | 1 | 0 |
| 3-95 | ethyl | ethyl | 8-methyl | 1-(N-2-thiazolylsulfamoyl) | H | H | 1 | 1 | 0 |
| 3-96 | ethyl | ethyl | 8-methyl | 1-(N-2-benzoimidazolylsulfamoyl) | H | H | 1 | 1 | 0 |
| 3-97 | ethyl | ethyl | 8-methyl | 1-(N-2-benzoxazolylsulfamoyl) | H | H | 1 | 1 | 0 |
| 3-98 | ethyl | ethyl | 8-methyl | 1-(N-2-benzothiazolylsulfamoyl) | H | H | 1 | 1 | 0 |
| 3-99 | ethyl | ethyl | 8-methyl | 1-(N-2-pyridylsulfamoyl) | H | H | 1 | 1 | 0 |
| 3-100 | ethyl | ethyl | 8-methyl | 1-(N-2-pyrimidylsulfamoyl) | H | H | 1 | 1 | 0 |
| 3-101 | ethyl | ethyl | 8-methyl | 1-(N-2-quinolylsulfamoyl) | H | H | 1 | 1 | 0 |
| 3-102 | ethyl | ethyl | 8-methyl | 1-(N-3H-indo-2-lylsulfamoyl) | H | H | 1 | 1 | 0 |
| 3-103 | ethyl | ethyl | 8-methyl | 1-methoxycarbonyl | H | H | 1 | 1 | 0 |
| 3-104 | ethyl | ethyl | 8-methyl | 1-ethoxycarbonyl | H | H | 1 | 1 | 0 |
| 3-105 | ethyl | ethyl | 8-methyl | 1-n-butoxycarbonyl | H | H | 1 | 1 | 0 |

TABLE 26

| No. | R¹ | R² | R³ | R⁴ | R⁵ | R⁶ | l | m | o |
|---|---|---|---|---|---|---|---|---|---|
| 3-106 | ethyl | ethyl | 8-methyl | 1-lauryloxycarbonyl | H | H | 1 | 1 | 0 |
| 3-107 | ethyl | ethyl | 8-methyl | 1-stearyloxycarbonyl | H | H | 1 | 1 | 0 |
| 3-108 | ethyl | ethyl | 8-methyl | 1-phenoxycarbonyl | H | H | 1 | 1 | 0 |
| 3-109 | ethyl | ethyl | 8-methyl | 1-p-tolyloxycarbonyl | H | H | 1 | 1 | 0 |
| 3-110 | ethyl | ethyl | 8-methyl | 1-o-chlorophenoxycarbonyl | H | H | 1 | 1 | 0 |
| 3-111 | ethyl | ethyl | 8-methyl | 1-o-methoxyphenocarbonyl | H | H | 1 | 1 | 0 |
| 3-112 | ethyl | ethyl | 8-methyl | 1-nitro | H | H | 1 | 1 | 0 |
| 3-113 | ethyl | ethyl | 8-methyl | 2-nitro | H | H | 1 | 1 | 0 |
| 3-117 | ethyl | ethyl | 8-methyl | 1-chloro | H | H | 1 | 1 | 0 |
| 3-118 | ethyl | ethyl | 8-methyl | 2-chloro | H | H | 1 | 1 | 0 |
| 3-119 | ethyl | ethyl | 8-methyl | 2-bromo | H | H | 1 | 1 | 0 |
| 3-120 | ethyl | ethyl | 8-methyl | 2-fluoro | H | H | 1 | 1 | 0 |
| 3-121 | ethyl | ethyl | 8-methyl | H | Ph | H | 1 | 0 | 0 |

TABLE 27

| No. | R¹ | R² | R³ | R⁴ | R⁵ | R⁶ | l | m | o |
|---|---|---|---|---|---|---|---|---|---|
| 3-127 | ethyl | ethyl | 8-methyl | H | H | 4-chloro | 1 | 0 | 1 |
| 3-128 | ethyl | ethyl | 8-methyl | H | H | 5-chloro | 1 | 0 | 1 |
| 3-129 | ethyl | ethyl | 8-methyl | H | H | 6-chloro | 1 | 0 | 1 |
| 3-131 | ethyl | ethyl | 8-methyl | H | H | 5-fluoro | 1 | 0 | 1 |
| 3-133 | ethyl | ethyl | 8-methyl | H | H | 5-phenyl | 1 | 0 | 1 |
| 3-140 | ethyl | ethyl | 8-methyl | H | H | 5-methoxycarbonyl | 1 | 0 | 1 |
| 3-141 | ethyl | ethyl | 8-methyl | H | H | 6-ethoxycarbonyl | 1 | 0 | 1 |
| 3-143 | ethyl | ethyl | 8-methyl | H | H | 5-trifluoromethyl | 1 | 0 | 1 |
| 3-144 | ethyl | ethyl | 8-methyl | H | H | 6-trifluoromethyl | 1 | 0 | 1 |
| 3-146 | ethyl | ethyl | 8-methyl | H | H | 5-nitro | 1 | 0 | 1 |
| 3-147 | ethyl | ethyl | 8-methyl | H | H | 6-nitro | 1 | 0 | 1 |

TABLE 28

| No. | R¹ | R² | R³ | R⁴ | R⁵ | R⁶ | l | m | o |
|---|---|---|---|---|---|---|---|---|---|
| 3-148 | ethyl | ethyl | 8-methyl | H | H | 4-carboxyl | 1 | 0 | 1 |
| 3-149 | ethyl | ethyl | 8-methyl | H | H | 6-carboxyl | 1 | 0 | 1 |
| 3-150 | ethyl | ethyl | 8-methyl | H | H | 6-phenoxycarbonyl | 1 | 0 | 1 |
| 3-151 | ethyl | ethyl | 8-methyl | H | H | 4-p-tolyloxycarbonyl | 1 | 0 | 1 |
| 3-152 | ethyl | ethyl | 8-methyl | H | H | 6-o-bromophenoxycarbonyl | 1 | 0 | 1 |
| 3-153 | ethyl | ethyl | 8-methyl | H | H | 6-acetyl | 1 | 0 | 1 |
| 3-154 | ethyl | ethyl | 8-methyl | H | H | 6-propionyl | 1 | 0 | 1 |
| 3-155 | ethyl | ethyl | 8-methyl | H | H | 6-isovaleryl | 1 | 0 | 1 |
| 3-156 | ethyl | ethyl | 8-methyl | H | H | 6-stearoyl | 1 | 0 | 1 |
| 3-157 | ethyl | ethyl | 8-methyl | H | H | 6-benzoyl | 1 | 0 | 1 |
| 3-158 | ethyl | ethyl | 8-methyl | H | H | 4-N-phenylcarbamoyl | 1 | 0 | 1 |
| 3-159 | ethyl | ethyl | 8-methyl | H | H | 6-N-methylcarbamoyl | 1 | 0 | 1 |
| 3-160 | ethyl | ethyl | 8-methyl | H | H | 5-N-allylcarbamoyl | 1 | 0 | 1 |
| 3-161 | ethyl | ethyl | 8-methyl | H | H | 4-(N-2-thienylcarbamoyl) | 1 | 0 | 1 |
| 3-162 | ethyl | ethyl | 8-methyl | H | H | 4-(N-benzothiazolylcarbamoyl | 1 | 0 | 1 |
| 3-163 | ethyl | ethyl | 8-methyl | H | H | 4-(N-2-pyridylcarbamoyl) | 1 | 0 | 1 |
| 3-164 | ethyl | ethyl | 8-methyl | H | H | 4-(N-3H-indo-2-lylcarbamoyl) | 1 | 0 | 1 |
| 3-165 | ethyl | ethyl | 8-methyl | H | H | 4-N-phenylsulfamoyl | 1 | 0 | 1 |
| 3-166 | ethyl | ethyl | 8-methyl | H | H | 4-N-methylsulfamoyl | 1 | 0 | 1 |
| 3-167 | ethyl | ethyl | 8-methyl | H | H | 6-(N-2-oxolanylmethylsulfamoyl) | 1 | 0 | 1 |
| 3-168 | ethyl | ethyl | 8-methyl | H | H | 4-(N-2-thiazolylsulfamoyl) | 1 | 0 | 1 |

TABLE 29

| No. | R¹ | R² | R³ | R⁴ | R⁵ | R⁶ | l | m | o |
|---|---|---|---|---|---|---|---|---|---|
| 3-169 | ethyl | ethyl | 8-methyl | H | H | 4-N-benzoimidazolylsulfamoyl | 1 | 0 | 1 |
| 3-170 | ethyl | ethyl | 8-methyl | H | H | 6-(N-2-pyrimidylsulfamoyl) | 1 | 0 | 1 |
| 3-171 | ethyl | ethyl | 8-methyl | H | F | H | 1 | 0 | 0 |
| 3-172 | ethyl | ethyl | 8-methyl | H | Cl | H | 1 | 0 | 0 |
| 3-173 | ethyl | ethyl | 8-methyl | H | Br | H | 1 | 0 | 0 |
| 3-176 | ethyl | ethyl | 8-methyl | H | cyano | H | 1 | 0 | 0 |
| 3-179 | ethyl | ethyl | 8-methyl | H | o-hydroxyphenyl | H | 1 | 0 | 0 |

TABLE 29-continued

| No. | $R^1$ | $R^2$ | $R^3$ | $R^5$ | $R^5$ | $R^6$ | l | m | o |
|---|---|---|---|---|---|---|---|---|---|
| 3-180 | ethyl | ethyl | 8-methyl | H | 3-pyridinyl | H | 1 | 0 | 0 |
| 3-188 | ethyl | ethyl | 8-methyl | H | formyl | H | 1 | 0 | 0 |
| 3-189 | ethyl | ethyl | 8-methyl | H | acetyl | H | 1 | 0 | 0 |

TABLE 30

| No. | $R^1$ | $R^2$ | $R^3$ | $R^4$ | $R^5$ | $R^6$ | l | m | o |
|---|---|---|---|---|---|---|---|---|---|
| 3-190 | 2-ethylhexyl | 2-ethylhexyl | H | H | hydroxyiminomethylcarbonyl | H | 0 | 0 | 0 |
| 3-191 | 2-ethylhexyl | 2-ethylhexyl | H | H | bromoacetyl | H | 0 | 0 | 0 |
| 3-192 | 2-ethylhexyl | 2-ethylhexyl | H | H | hydroxycarbonyl | H | 0 | 0 | 0 |
| 3-193 | 2-ethylhexyl | 2-ethylhexyl | H | H | methoxycarbonyl | H | 0 | 0 | 0 |
| 3-194 | 2-ethylhexyl | 2-ethylhexyl | H | H | n-hexylcarbonyl | H | 0 | 0 | 0 |
| 3-195 | 2-ethylhexyl | 2-ethylhexyl | H | H | aminothioarbonyl | H | 0 | 0 | 0 |

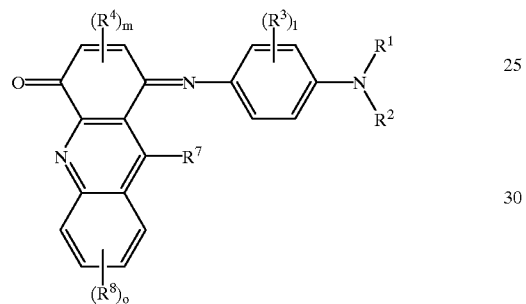

(4)

TABLE 31

| No. | $R^1$ | $R^2$ | $R^3$ | $R^4$ | $R^7$ | $R^8$ | l | m | o |
|---|---|---|---|---|---|---|---|---|---|
| 4-1 | ethyl | ethyl | 8-methyl | H | H | H | 1 | 0 | 0 |
| 4-2 | ethyl | ethyl | H | H | H | H | 0 | 0 | 0 |
| 4-3 | methyl | methyl | H | H | H | H | 0 | 0 | 0 |
| 4-4 | n-propyl | n-propyl | H | H | H | H | 0 | 0 | 0 |
| 4-5 | i-propyl | i-propyl | H | H | H | H | 0 | 0 | 0 |
| 4-6 | n-butyl | n-butyl | H | H | H | H | 0 | 0 | 0 |
| 4-7 | s-butyl | H | H | H | H | H | 0 | 0 | 0 |
| 4-8 | n-pentyl | n-pentyl | H | H | H | H | 0 | 0 | 0 |
| 4-9 | n-heyxl | n-hexyl | H | H | H | H | 0 | 0 | 0 |
| 4-10 | 2-ethylhexyl | 2-ethylhexyl | H | H | H | H | 0 | 0 | 0 |
| 4-11 | cetyl | cetyl | H | H | H | H | 0 | 0 | 0 |
| 4-12 | ethyl | 2-cyanoethyl | H | H | H | H | 0 | 0 | 0 |
| 4-13 | ethyl | 2-chloroethyl | H | H | H | H | 0 | 0 | 0 |
| 4-14 | 2-ethoxyethyl | 2-ethoxyethyl | H | H | H | H | 0 | 0 | 0 |
| 4-15 | methoxyethoxyethyl | methoxyethoxyethyl | H | H | H | H | 0 | 0 | 0 |
| 4-16 | benzyl | benzyl | H | H | Ph | H | 0 | 0 | 0 |
| 4-17 | ethyl | benzyloxyethyl | H | H | Ph | H | 0 | 0 | 0 |
| 4-18 | ethyl | methylcarbonyloxyethyl | H | H | Ph | H | 0 | 0 | 0 |
| 4-19 | ethyl | 2-phenoxyethyl | H | H | Ph | H | 0 | 0 | 0 |
| 4-20 | ethyl | 2-acetoxyethyl | H | H | Ph | H | 0 | 0 | 0 |
| 4-21 | 2-caboxyethyl | 2-caboxyethyl | H | H | H | H | 0 | 0 | 0 |

TABLE 32

| No. | $R^1$ | $R^2$ | $R^3$ | $R^4$ | $R^7$ | $R^8$ | l | m | o |
|---|---|---|---|---|---|---|---|---|---|
| 4-22 | ethoxycabonylmethyl | ethoxycabonylmethyl | H | H | H | H | 0 | 0 | 0 |
| 4-23 | 3-mesylpropyl | 3-mesylpropyl | H | H | H | H | 0 | 0 | 0 |
| 4-24 | ethyl | 2-oxolanylmethyl | H | H | H | H | 0 | 0 | 0 |
| 4-25 | H | phenyl | H | H | H | H | 0 | 0 | 0 |
| 4-26 | H | p-tolyl | H | H | H | H | 0 | 0 | 0 |

TABLE 32-continued

| No. | R¹ | R² | R³ | R⁴ | R⁷ | R⁸ | l | m | o |
|---|---|---|---|---|---|---|---|---|---|
| 4-27 | H | p-chlorophenyl | H | H | H | H | 0 | 0 | 0 |
| 4-28 | H | p-methoxyphenyl | H | H | H | H | 0 | 0 | 0 |
| 4-29 | H | p-n-butoxyphenyl | H | H | H | H | 0 | 0 | 0 |
| 4-30 | 2-propenyl | 2-propenyl | H | H | H | H | 0 | 0 | 0 |
| 4-31 | ethyl | 2-methyl-2-propenyl | H | H | H | H | 0 | 0 | 0 |
| 4-32 | ethyl | 2-chloro-2-propenyl | H | H | H | H | 0 | 0 | 0 |
| 4-33 | ethyl | cyclohexyl | H | H | H | H | 0 | 0 | 0 |
| 4-34 | | piperidinyl | H | H | H | H | 0 | 0 | 0 |
| 4-35 | | morpholinyl | H | H | H | H | 0 | 0 | 0 |
| 4-38 | ethyl | ethyl | 8-ethyl | H | H | H | 1 | 0 | 0 |
| 4-39 | ethyl | ethyl | 8-cyclohexyl | H | H | H | 1 | 0 | 0 |
| 4-41 | ethyl | ethyl | 8-(2-propenyl) | H | H | H | 1 | 0 | 0 |
| 4-42 | ethyl | ethyl | 8-benzyl | H | H | H | 1 | 0 | 0 |

TABLE 33

| No. | R¹ | R² | R³ | R⁴ | R⁷ | R⁸ | l | m | o |
|---|---|---|---|---|---|---|---|---|---|
| 4-43 | ethyl | ethyl | 8-methoxy | H | H | H | 1 | 0 | 0 |
| 4-44 | 2-phenoxyethyl | 2-phenoxyethyl | 8,10-diethoxy | H | H | H | 2 | 0 | 0 |
| 4-45 | 2-ethoxyethyl | 2-ethoxyethyl | 8-methoxy-10-methyl | H | H | H | 2 | 0 | 0 |
| 4-49 | n-butyl | n-butyl | 8-diethylamino | H | H | H | 1 | 0 | 0 |
| 4-50 | n-butyl | n-butyl | 8-diisopropylamino | H | H | H | 1 | 0 | 0 |
| 4-51 | n-butyl | n-butyl | 8-tosylamino | H | H | H | 1 | 0 | 0 |
| 4-52 | ethyl | ethyl | 8-mesylamino | H | H | H | 1 | 0 | 0 |
| 4-53 | n-butyl | n-butyl | 8-laurolyamino | H | H | H | 1 | 0 | 0 |
| 4-54 | ethyl | ethyl | 8-palmitoylamino | H | H | H | 1 | 0 | 0 |
| 4-55 | ethyl | ethyl | 8-stearoylamino | H | H | H | 1 | 0 | 0 |
| 4-56 | ethyl | ethyl | 8-(1-naphthoyl)amino | H | H | H | 1 | 0 | 0 |
| 4-57 | 2-ethylhexyl | 2-ethylhexyl | 8-methyl | H | H | H | 1 | 0 | 0 |
| 4-58 | 2-ethylhexyl | 2-ethylhexyl | 8-methylthio | H | H | H | 1 | 0 | 0 |
| 4-59 | ethyl | ethyl | 8-n-butylthio | H | H | H | 1 | 0 | 0 |
| 4-60 | n-butyl | n-butyl | 8-phenylthio | H | H | H | 1 | 0 | 0 |
| 4-61 | ethyl | ethyl | 8-p-chlorophenylthio | H | H | H | 1 | 0 | 0 |
| 4-62 | n-butyl | n-butyl | 8-benzylthio | H | H | H | 1 | 0 | 0 |
| 4-63 | ethyl | ethyl | 8-ureido | H | H | H | 1 | 0 | 0 |

TABLE 34

| No. | R¹ | R² | R³ | R⁴ | R⁷ | R⁸ | l | m | o |
|---|---|---|---|---|---|---|---|---|---|
| 4-64 | n-butyl | n-butyl | 8-N-n-propylureido | H | H | H | 1 | 0 | 0 |
| 4-65 | ethyl | ethyl | 8-N,N-diethylureido | H | H | H | 2 | 0 | 0 |
| 4-66 | ethyl | ethyl | 8-thioureido | H | H | H | 2 | 0 | 0 |
| 4-67 | ethyl | ethyl | 8-N-acetyl-N-phenylthioureido | H | H | H | 2 | 0 | 0 |
| 4-68 | ethyl | ethyl | 8-methyl | 1-acetyl | H | H | 2 | 0 | 0 |
| 4-69 | ethyl | ethyl | 8-methyl | 1-isovaleryl | H | H | 1 | 0 | 0 |
| 4-70 | ethyl | ethyl | 8-methyl | 1-stearoyl | H | H | 1 | 0 | 0 |
| 4-71 | ethyl | ethyl | 8-methyl | 1-benzoyl | H | H | 1 | 0 | 0 |
| 4-72 | ethyl | ethyl | 8-methyl | 1-(1-naphthoyl) | H | H | 1 | 0 | 0 |
| 4-73 | ethyl | ethyl | 8-methyl | 1-carboxy | H | H | 1 | 0 | 0 |
| 4-74 | ethyl | ethyl | 8-methyl | 1-N-phenylcarbamoyl | H | H | 1 | 0 | 0 |
| 4-75 | ethyl | ethyl | 8-methyl | 1-N-methylcarbamoyl | H | H | 1 | 0 | 0 |
| 4-76 | ethyl | ethyl | 8-methyl | 1-N-ethoxymethylcarbamoyl | H | H | 1 | 0 | 0 |
| 4-77 | ethyl | ethyl | 8-methyl | 1-(N-2-oxolanylmethylcarbamoyl) | H | H | 1 | 0 | 0 |
| 4-78 | ethyl | ethyl | 8-methyl | 1-N-allylcarbamoyl | H | H | 1 | 0 | 0 |
| 4-79 | ethyl | ethyl | 8-methyl | 1-(N-3-(2-methoxycarbonyl)thienylcarbamoyl) | H | H | 1 | 0 | 0 |
| 4-80 | ethyl | ethyl | 8-methyl | 1-N-2-thiazolylcarbamoyl | H | H | 1 | 0 | 0 |
| 4-81 | ethyl | ethyl | 8-methyl | 1-(N-2-benzoimidazolylcarbamoyl) | H | H | 1 | 0 | 0 |
| 4-82 | ethyl | ethyl | 8-methyl | 1-(N-2-benzoxazolylcarbamoyl) | H | H | 1 | 0 | 0 |
| 4-83 | ethyl | ethyl | 8-methyl | 1-(N-2-benzothioazolyl-carbamoyl) | H | H | 1 | 0 | 0 |
| 4-84 | ethyl | ethyl | 8-methyl | 1-(N-2-pyridylcarbamoyl) | H | H | 1 | 0 | 0 |

TABLE 35

| No. | R¹ | R² | R³ | R⁴ | R⁷ | R⁸ | l | m | o |
|---|---|---|---|---|---|---|---|---|---|
| 4-85 | ethyl | ethyl | 8-methyl | 1-(N-4-pyrimidylcarbamoyl) | H | H | 1 | 1 | 0 |
| 4-86 | ethyl | ethyl | 8-methyl | 1-(N-2-quinolylcarbamoyl) | H | H | 1 | 1 | 0 |
| 4-87 | ethyl | ethyl | 8-methyl | 1-(N-3H-indo-2-lylcarbamoyl) | H | H | 1 | 1 | 0 |
| 4-88 | ethyl | ethyl | 8-methyl | 1-sulfo | H | H | 1 | 1 | 0 |

TABLE 35-continued

| No. | R¹ | R² | R³ | R⁴ | R⁷ | R⁸ | l | m | o |
|---|---|---|---|---|---|---|---|---|---|
| 4-89 | ethyl | ethyl | 8-methyl | 1-N-phenylsulfamoyl | H | H | 1 | 1 | 0 |
| 4-90 | ethyl | ethyl | 8-methyl | 1-N-methylsulfamoyl | H | H | 1 | 1 | 0 |
| 4-91 | ethyl | ethyl | 8-methyl | 1-N-ethoxymethylsulfamoyl | H | H | 1 | 1 | 0 |
| 4-92 | ethyl | ethyl | 8-methyl | 1-(N-2-oxolanylmethylsulfamoyl) | H | H | 1 | 1 | 0 |
| 4-93 | ethyl | ethyl | 8-methyl | 1-N-allylsulfamoyl | H | H | 1 | 1 | 0 |
| 4-94 | ethyl | ethyl | 8-methyl | 1-(N-4-2-thienylsulfamoyl) | H | H | 1 | 1 | 0 |
| 4-95 | ethyl | ethyl | 8-methyl | 1-(N-2-thiazolylsulfamoyl) | H | H | 1 | 1 | 0 |
| 4-96 | ethyl | ethyl | 8-methyl | 1-(N-2-benzoimidazolylsulfamoyl) | H | H | 1 | 1 | 0 |
| 4-97 | ethyl | ethyl | 8-methyl | 1-(N-2-benzoxazolylsulfamoyl) | H | H | 1 | 1 | 0 |
| 4-98 | ethyl | ethyl | 8-methyl | 1-(N-2-benzothiazolylsulfamoyl) | H | H | 1 | 1 | 0 |
| 4-99 | ethyl | ethyl | 8-methyl | 1-(N-2-pyridylsulfamoyl) | H | H | 1 | 1 | 0 |
| 4-100 | ethyl | ethyl | 8-methyl | 1-(N-4-pyrimidylsulfamoyl) | H | H | 1 | 1 | 0 |
| 4-101 | ethyl | ethyl | 8-methyl | 1-(N-2-quinolylsulfamoyl) | H | H | 1 | 1 | 0 |
| 4-102 | ethyl | ethyl | 8-methyl | 1-(N-3H-indo-2-lylsulfamoyl) | H | H | 1 | 1 | 0 |
| 4-103 | ethyl | ethyl | 8-methyl | 1-methoxycarbonyl | H | H | 1 | 1 | 0 |
| 4-104 | ethyl | ethyl | 8-methyl | 1-ethoxycarbonyl | H | H | 1 | 1 | 0 |
| 4-105 | ethyl | ethyl | 8-methyl | 1-n-butoxycarbonyl | H | H | 1 | 1 | 0 |

TABLE 36

| No. | R¹ | R² | R³ | R⁴ | R⁷ | R⁸ | l | m | o |
|---|---|---|---|---|---|---|---|---|---|
| 4-106 | ethyl | ethyl | 8-methyl | 1-lauryloxycarbonyl | H | H | 1 | 1 | 0 |
| 4-107 | ethyl | ethyl | 8-methyl | 1-stearyloxycarbonyl | H | H | 1 | 1 | 0 |
| 4-108 | ethyl | ethyl | 8-methyl | 1-phenoxycarbonyl | H | H | 1 | 1 | 0 |
| 4-109 | ethyl | ethyl | 8-methyl | 1-tolyloxycarbonyl | H | H | 1 | 1 | 0 |
| 4-110 | ethyl | ethyl | 8-methyl | 1-p-chlorophenoxycarbonyl | H | H | 1 | 1 | 0 |
| 4-111 | ethyl | ethyl | 8-methyl | 1-p-methoxyphenocarbonyl | H | H | 1 | 1 | 0 |
| 4-112 | ethyl | ethyl | 8-methyl | 1-nitro | H | H | 1 | 1 | 0 |
| 4-113 | ethyl | ethyl | 8-methyl | 2-nitro | H | H | 1 | 1 | 0 |
| 4-117 | ethyl | ethyl | 8-methyl | 1-chloro | H | H | 1 | 1 | 0 |
| 4-118 | ethyl | ethyl | 8-methyl | 2-chloro | H | H | 1 | 1 | 0 |
| 4-119 | ethyl | ethyl | 8-methyl | 2-bromo | H | H | 1 | 1 | 0 |
| 4-120 | ethyl | ethyl | 8-methyl | 2-fluoro | H | H | 1 | 1 | 0 |
| 4-121 | ethyl | ethyl | 8-methyl | H | Ph | H | 1 | 0 | 0 |

TABLE 37

| No. | R¹ | R² | R³ | R⁴ | R⁷ | R⁸ | l | m | o |
|---|---|---|---|---|---|---|---|---|---|
| 4-127 | ethyl | ethyl | 8-methyl | H | H | 4-chloro | 1 | 0 | 1 |
| 4-128 | ethyl | ethyl | 8-methyl | H | H | 5-chloro | 1 | 0 | 1 |
| 4-129 | ethyl | ethyl | 8-methyl | H | H | 6-chloro | 1 | 0 | 1 |
| 4-130 | ethyl | ethyl | 8-methyl | H | H | 7-chloro | 1 | 0 | 1 |
| 4-131 | ethyl | ethyl | 8-methyl | H | H | 5-fluoro | 1 | 0 | 1 |
| 4-133 | ethyl | ethyl | 8-methyl | H | H | 5-phenyl | 1 | 0 | 1 |
| 4-140 | ethyl | ethyl | 8-methyl | H | H | 5-methoxy-carbonyl | 1 | 0 | 1 |
| 4-141 | ethyl | ethyl | 8-methyl | H | H | 7-ethoxy-carbonyl | 1 | 0 | 1 |
| 4-142 | ethyl | ethyl | 8-methyl | H | H | 7-cyano | 1 | 0 | 1 |
| 4-143 | ethyl | ethyl | 8-methyl | H | H | 5-trifluoromethyl | 1 | 0 | 1 |
| 4-144 | ethyl | ethyl | 8-methyl | H | H | 6-trifluoromethyl | 1 | 0 | 1 |
| 4-146 | ethyl | ethyl | 8-methyl | H | H | 5-nitro | 1 | 0 | 1 |
| 4-147 | ethyl | ethyl | 8-methyl | H | H | 6-nitro | 1 | 0 | 1 |

TABLE 38

| No | R¹ | R² | R³ | R⁴ | R⁷ | R⁸ | l | m | o |
|---|---|---|---|---|---|---|---|---|---|
| 4-148 | ethyl | ethyl | 8-methyl | H | H | 4-carboxyl | 1 | 0 | 1 |
| 4-149 | ethyl | ethyl | 8-methyl | H | H | 6-carboxyl | 1 | 0 | 1 |
| 4-150 | ethyl | ethyl | 8-methyl | H | H | 6-phenoxycarbonyl | 1 | 0 | 1 |
| 4-151 | ethyl | ethyl | 8-methyl | H | H | 4-p-tolyloxycarbonyl | 1 | 0 | 1 |
| 4-152 | ethyl | ethyl | 8-methyl | H | H | 6-o-bromophenoxycarbonyl | 1 | 0 | 1 |
| 4-153 | ethyl | ethyl | 8-methyl | H | H | 5-acetyl | 1 | 0 | 1 |
| 4-154 | ethyl | ethyl | 8-methyl | H | H | 6-propionyl | 1 | 0 | 1 |
| 4-155 | ethyl | ethyl | 8-methyl | H | H | 6-isovaleryl | 1 | 0 | 1 |

TABLE 38-continued

| No | R¹ | R² | R³ | R⁴ | R⁷ | R⁸ | l | m | o |
|---|---|---|---|---|---|---|---|---|---|
| 4-156 | ethyl | ethyl | 8-methyl | H | H | 6-stearoyl | 1 | 0 | 1 |
| 4-157 | ethyl | ethyl | 8-methyl | H | H | 6-benzoyl | 1 | 0 | 1 |
| 4-158 | ethyl | ethyl | 8-methyl | H | H | 4-N-phenylcarbamoyl | 1 | 0 | 1 |
| 4-159 | ethyl | ethyl | 8-methyl | H | H | 6-N-methylcarbamoyl | 1 | 0 | 1 |
| 4-160 | ethyl | ethyl | 8-methyl | H | H | 5-N-allylcarbamoyl | 1 | 0 | 1 |
| 4-161 | ethyl | ethyl | 8-methyl | H | H | 4-(N-2-thienylcarbamoyl) | 1 | 0 | 1 |
| 4-162 | ethyl | ethyl | 8-methyl | H | H | 4-N-benzothiazolylcarbamoyl | 1 | 0 | 1 |
| 4-163 | ethyl | ethyl | 8-methyl | H | H | 4-(N-2-pyridylcarbamoyl) | 1 | 0 | 1 |
| 4-164 | ethyl | ethyl | 8-methyl | H | H | 4-(N-3H-indo-2-lylcarbamoyl) | 1 | 0 | 1 |
| 4-165 | ethyl | ethyl | 8-methyl | H | H | 4-(N-phenylsulfamoyl | 1 | 0 | 1 |
| 4-166 | ethyl | ethyl | 8-methyl | H | H | 4-N-methylsulfamoyl | 1 | 0 | 1 |
| 4-167 | ethyl | ethyl | 8-methyl | H | H | 6-(N-2-oxolanylmethylsulfamoyl) | 1 | 0 | 1 |
| 4-168 | ethyl | ethyl | 8-methyl | H | H | 4-(N-2-thiazolylsulfamoyl) | 1 | 0 | 1 |

TABLE 39

| No. | R¹ | R² | R³ | R⁴ | R⁷ | R⁸ | l | m | o |
|---|---|---|---|---|---|---|---|---|---|
| 4-169 | ethyl | ethyl | 8-methyl | H | H | 4-N-benzoimidazolylsulfamoyl | 1 | 0 | 1 |
| 4-170 | ethyl | ethyl | 8-methyl | H | H | 6-(N-2-pyrimidylsulfamoyl) | 1 | 0 | 1 |
| 4-171 | ethyl | ethyl | 8-methyl | H | F | H | 1 | 0 | 0 |
| 4-172 | ethyl | ethyl | 8-methyl | H | Cl | H | 1 | 0 | 0 |
| 4-173 | ethyl | ethyl | 8-methyl | H | Br | H | 1 | 0 | 0 |
| 4-176 | ethyl | ethyl | 8-methyl | H | cyano | H | 1 | 0 | 0 |
| 4-179 | ethyl | ethyl | 8-methyl | H | o-hydroxyphenyl | H | 1 | 0 | 0 |
| 4-180 | ethyl | ethyl | 8-methyl | H | 3-pyridinyl | H | 1 | 0 | 0 |
| 4-188 | ethyl | ethyl | 8-methyl | H | formyl | H | 1 | 0 | 0 |
| 4-189 | ethyl | ethyl | 8-methyl | H | acetyl | H | 1 | 0 | 0 |

TABLE 40

| No. | R¹ | R² | R³ | R⁴ | R⁷ | R⁸ | l | m | o |
|---|---|---|---|---|---|---|---|---|---|
| 4-190 | 2-ethylhexyl | 2-ethylhexyl | H | H | hydroxyiminomethylcarbonyl | H | 0 | 0 | 0 |
| 4-191 | 2-ethylhexyl | 2-ethylhexyl | H | H | broinoacetyl | H | 0 | 0 | |
| 4-192 | 2-ethylhexyl | 2-ethylhexyl | H | H | hydroxycarbonyl | H | 0 | 0 | 0 |
| 4-193 | 2-ethylhexyl | 2-ethylhexyl | H | H | methoxycarbonyl | H | 0 | 0 | 0 |
| 4-194 | 2-ethylhexyl | 2-ethylhexyl | H | H | n-hexylcarbonyl | H | 0 | 0 | 0 |
| 4-195 | 2-ethylhexyl | 2-ethylhexyl | H | H | aminothiocarbonyl | H | 0 | 0 | 0 |

A process for producing new indoaniline derivatives represented by the general formula (3) and (4), that is, an oxidative addition reaction of a 4-hydroxyphenanthridine derivative represented by the general formula (6) or a 4-hydroxyacridine derivative represented by the general formula (7) with a p-N,N-substituted aminoaniline compound represented by the formula (8) or its hydrochloride, sulfate, nitrate or organic acid salt proceeds in a solvent such as water, methanol, ethanol, isopropanol, acetone, methyl ethyl ketone, dioxane or tetrahydrofuran by using an oxidizing agent such as chromic acid, lead tetraacetate, potassium nitrosodisulfonate, ammonium peroxodisulfate, 2,3-dichloro-5,6-dicyano-1,4-benzoquinone, silver nitrate, silver carbonate, silver halogenide and ferric chloride. From the viewpoint of operativity in preparation, yield or ease of purification of products, ammonium peroxodisulfate or silver nitrate is preferable as an oxidizing agent. This reaction is performed at the temperature range between 0° C. and 100° C. for a period of 10 min to 24 hr. After the completion of the reaction, such operations as extraction and condensation are performed and a new indoaniline derivative represented by the general formula (3) or (4) can be prepared by using a purifying method such as column chromatography or recrystallization if necessary.

4-hydroxyphenanthridine derivatives represented by the general formula (6) can be prepared by using the method of S. V. Kessar and others (Tetrahedron, Vol. 29, p. 177, 1973) but the present invention is not limited to this. As a typical example, a synthetic method of 4-hydroxyphenanthridine is shown below.

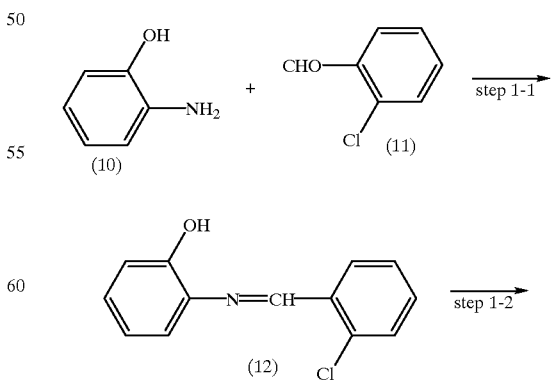

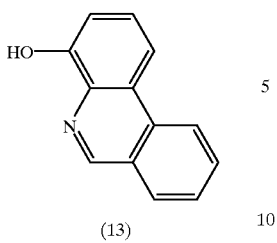

(13)

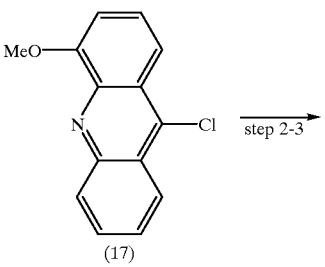

(17)

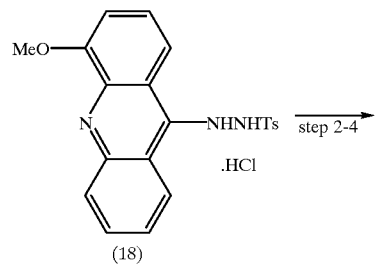

(18)

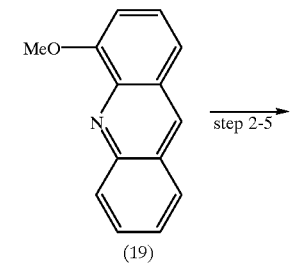

(19)

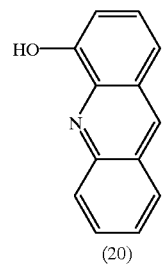

(20)

STEP-1-1 (Dehydration Condensation Reaction)

Under conditions: (A) initial reaction at 80 to 200° C. in a sealed tube; (B) subsequent reflux in an organic solvent such as methanol or ethanol; (C) removal of the water produced at reaction temperatures of 80 to 200° C. by using the Dean-Stark apparatus; and so on, o-hydroxyaniline (10) and o-chlorobenzaldehyde (11) are allowed to react, so that anil (12) can be prepared. In preparing a derivative of anil, the most suitable conditions of dehydration condensation reaction depend on materials, but the condition (B) is preferable with respect to apparatus and operativity. The reaction proceeds for a period of 10 min to 24 hr, the organic solvent is removed after the completion of the reaction and the product can be purified by column chromatography, recrystallization or the like if necessary.

STEP-1-2 (Ring Closure Reaction)

In ammonium liquor, anil (12) undergoes the ring closure reaction by using metal potassium, so that 4-hydroxyphenanthridine (13) can be prepared. The ring closure reaction proceeds within the range between −75° C. and −30° C. for a period of 10 min to 24 hr. After the completion of the reaction, ammonium is removed and the obtained residue can be purified by column chromatography, recrystallization or the like if necessary.

4-hydroxyacridine derivatives represented by the general formula (7) can be prepared by using the following method, but the present invention is not limited to this. As a typical example, a synthetic method of 4-hydroxyacridine is shown below.

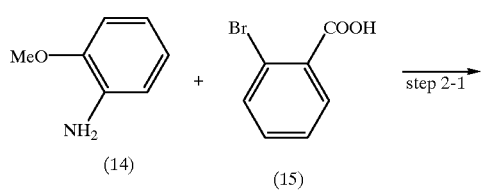

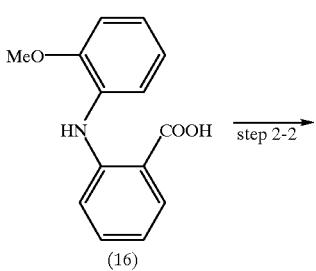

(16)

STEP-2-1 (Ullmann Reaction)

In the presence of a catalyst such as copper salt, o-anisidine (14), o-bromobenzoic acid (15) and potassium carbonate are allowed to react without solvent or in an inactive solvent having a high boiling point, so that 2-methoxydiphenylamine-2'-carboxylic acid (16) can be obtained. In place of potassium carbonate, an inorganic base such as lithium hydroxide, sodium hydroxide, potassium hydroxide, sodium carbonate, sodium bicarbonate, and potassium bicarbonate, or an organic base such as pyridine, triethylamine or dimethylaniline can be used. As the catalyst, copper powder, copper bromide, copper iodide or copper oxide can be used and iodine may be added as co-catalyst. The reaction can proceed without solvent, but an inactive solvent havign a high-boiling point such as toluene, xylene, mesitylene, chlorobenzene, dichlorobenzene, bromobenzene, nitrobenzene and DMF may be added to assist the mixing. Preferably, the reaction temperature ranges from 80° C. to 200° C. and the reaction time ranges from 10 min to 24 hr.

STEP-2-2 (Ring Closure Reaction)

By reaction of 2-methoxydiphenylamine-2'-carboxylic acid (16) with phosphorus oxychloride, 4-methoxy-9- chloroacridine (17) can be obtained. Phosphorus oxychloride acts as reaction reagent, but may be used in the range of more than one equivalent to the substrate due to also acting as a solvent. Phosphorus trichloride and phosphorus pentachloride may be added to phosphorus oxychloride as supplementary reagent. Preferably the reaction temperature ranges from 50° C. to 105° C. and the reaction time ranges from 10 min to 24 hr.

STEP-2-3 (p-toluenesulfonylhydrazide)

By reaction of 4-methoxy-9-chloroacridine (17) with p-toluenesulfonylhydrazide, $N_1$-9-acridinyl-$N_2$-p-toluenesulfonylhydrazide (18) can be obtained. In place of p-toluenesulfonylhydrazide, benzenesulfonylhydrazide can be employed.

STEP-2-4 (Decomposition Reaction)

By heating $N_1$-9-acridinyl-$N_2$-p-toluenesulfonylhydrazine (18) together with alkali in ethylene glycol, 4-methoxyacridine (19) can be obtained. The reaction solvent is only required to have a boiling point higher than 60° C. and ethanol, propanol, butanol, propylene glycol, glycerol and so on can be used in place of ethylene glycol. As alkali, an inorganic base such as lithium hydroxide, sodium hydroxide, potassium hydroxide, sodium carbonate, potassium carbonate, sodium bicarbonate or potassium bicarbonate is preferable. Preferably the reaction temperature ranges from 60° C. to 150° C. and the reaction time ranges from 10 min to 24 hr.

STEP-2-5 (Demethylation Reaction)

By subjecting 4-methoxyacridine (19) to demethylation reaction, 4-hydroxyacridine (20) can be obtained. As a demethylation reaction reagent, hydrobromic acid, hydroiodic acid, aluminum chloride, aluminum bromide, pyridine hydrochloride, boron trichloride, boron tribromide and boron triiodide can be used but the reagent is not limited to these. The reaction temperature and reaction time depend on reaction reagents, but, when using hydrobromic acid as a reagent, for example, a preferable reaction temperature is in the range of 90–120° C. and a preferable reaction time is in the range of 10 min to 24 hr. A preferable quantity of a reagent is in the range of 1–20 equivalent to the substrate. A preferable reaction solvent is inactive to the reaction reagent mentioned above. A liquid reaction reagent, if employed, will be capable of acting also as a solvent. The transparent recording medium, prepared using a new indoaniline metal complex according to the present invention, basically comprises a substrate and a recording layer, said recording layer comprising a developer represented by the general formula (5), a metal salt of an organic acid or a leuco dye which develops a color by reacting with said developer and a light-absorbing material containing a new indoaniline metal complex represented by the general formula (1) or the general formula (2) for absorbing and converting near-infrared rays into heat, and further, depending on the use of the medium, an underlayer is provided between the substrate and the recording layer or a protective layer is provided on the recording layer.

Materials of substrates employed in the present invention are general recording-medium-supporting members such as glass and plastic, but plastic is preferable with respect to various aspects. Plastic materials include acrylic resin, polyester resin, polymethacrylic resin, polyvinyl acetate resin, polyvinyl chloride resin, nitrocellulose, polyethylene resin, polypropylene resin, polystyrene resin, polycarbonate resin, polyimide resin, epoxy resin and polysulfone resin, among which those shaped in film, sheet or plate, resistant to heat and high in transparency are preferable.

Preferable developers employed in the present invention are compounds represented by the following general formula (5):

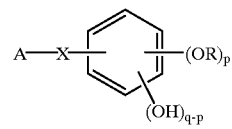

(5)

(here, X: COO, CONH and $SO_2$; A: substituted or non-substituted alkyl group, cycloalkyl group, vinyl group, allyl group, aryl group, benzyl group and naphthyl group; R: either N-substituted carbamoyl group ($CONHR^{10}$) or O-substituted oxycarbonyl ($COOR^{11}$); $R^{10}$ and $R^{11}$: substituted or non-substituted alkyl group, cycloalkyl group, vinyl group, allyl group, aryl group, benzyl group, naphthyl group, mesyl group and tosyl group; p and q: an integer of 1–3 and $p \leq q$).

Example of A can be given as follows: alkyl groups such as methyl, ethyl, n-propyl, iso-propyl, n-butyl, iso-butyl, sec-butyl, tert-butyl, n-pentyl, n-hexyl, n-octyl, 2-ethylhexyl, lauryl, myristyl, parmityl, stearyl, behenyl, 2-hydroxyethyl, 2-cyanoethyl, 2-aminoethyl, 2-chloroethyl, 2-bromoethyl, 2-iodoethyl, 2-fluoroethyl, trifluoromethyl, 2,2,2-trifluoroethyl, 2-methoxyethyl, methoxyethoxyethyl, 2-allyloxyethyl, benzyl, phenetyl, 2-benzyloxyethyl, benzylcarbonyloxymethyl, 2-phenoxyethyl, 2-acetoxyethyl, 2-carboxyethyl, ethoxycarbonylmethyl, methoxycarbonylethyl, 3-mesylpropyl, 2-furylmethyl and 2-oxolanylmethyl; cycloalkyl groups such as cyclopentyl, cyclohexyl and 2-methylcyclohexyl; allyl groups such as 2-propenyl, 2-butenyl, 2-pentenyl, 2-hexenyl, 2-chloro-2-propenyl and 2-methyl-2-pentenyl; and aryl groups such as phenyl, o-tolyl, m-tolyl, p-tolyl, o-chlorophenyl, m-chlorophenyl, p-chlorophenyl, o-bromophenyl, m-bromophenyl, p-bromophenyl, o-methoxyphenyl, m-methoxyphenyl, p-methoxyphenyl, p-ethoxyphenyl and p-butoxyphenyl.

Examples of N-substituted carbamoyl groups can be given as follows: methylcarbamoyl, ethylcarbamoyl, n-propylcarbamoyl, iso-propylcarbamoyl, n-butylcarbamoyl, tert-butylcarbamoyl, n-octadecylcarbamoyl, cyclohexylcarbamoyl, allylcarbamoyl, chloromethylcarbamoyl, 2-chloroethylcarbamoyl, phenylcarbamoyl, o-tolylcarbamoyl, m-tolylcarbamoyl, p-tolylcarbamoyl, naphthylcarbamoyl, o-chlorophenylcarbamoyl, m-chlorophenylcarbamoyl, p-chlorophenylcarbamoyl, 3,4-dichlorophenylcarbamoyl, o-methoxyphenylcarbamoyl, m-methoxyphenylcarbamoyl, p-methoxyphenylcarbamoyl, p-toluenesulfonylcarbamoyl, benzylcarbamoyl, α-dimethylbenzylcarbamoyl, α, α-dimethylbenzylcarbamoyl, m-methyl-α, α-dimethylbenzylcarbamoyl, m-ethyl-α, α-dimethylbenzylcarbamoyl, m-propyl-α, α-dimethylbenzylcarbamoyl and m-isopropyl-α, α-dimethylbenzylcarbamoyl.

On the other hand, examples of O-substituted oxycarbonyl groups can be given as follows: methoxycarbonyl, ethoxycarbonyl, n-propoxycarbonyl, n-butoxycarbonyl, iso-butoxycarbonyl, tert-butoxycarbonyl, n-hexadecyloxycarbonyl, n-octadecyloxycarbonyl, allyloxycarbonyl, vinyloxycarbonyl, 2,2,2-trichloroethoxycarbonyl, phenoxycarbonyl, naphthyloxycarbonyl and 2-(trimethylsilyl)ethoxy carbonyl.

Organic acids for organic acid metal salts employed in the present invention include aliphatic carboxylic acid derivatives, benzoic acid derivatives and phthalic acid derivatives, but benzoic acid derivatives are preferable, among which o- and m-substituted benzoic acid derivatives are especially preferable, such as o-benzoylbenzoic acid, o-(2-methyl)benzoylbenzoic acid, o-(2-ethyl)benzoylbenzoic acid, o-methylbenzoic acid, m-methylbenzoic acid, o-phenylbenzoic acid, m-phenylbenzoic acid, o-tolylbenzoic acid, m-tolylbenzoic acid, o-chlorobenzoic acid, m-chlorobenzoic acid, o-bromobenzoic acid and m-bromobenzoic acid.

Preferable metals for organic acid metal salts employed in the present invention are iron, silver, copper, vanadium and cobalt, among which iron is utmost preferable.

Any colorless electron-donating dye conventionally known in the field of heat-sensitive recording paper and pressure-sensitive recording paper can be used as a leuco dye in the present invention. The following compounds can be given as typical examples: crystal violet lactone, 3-diethylamino-6-methyl-7-anilinofluoran, 3-dibutylamino-6-methyl-7-anilinofluoran, 3-(N-ethyl-N-isoamylamino)-6-methyl-7-anilinofluoran, 3-(4-diethylamino-2-ethoxyphenyl)-3-(1-ethyl-2-methyl-indol-3-yl)-4-azaphthalide and 3-(N-ethyl-N-cyclohexylamino)-6-methyl-7-anilinofluoran.

The above developers and organic acid metal salts or leuco dyes are dissolved together with a binder in an organic solvent suitable for solvent coating, such as toluene, acetone, methyl ethyl ketone, methyl isobutyl ketone and chloroform.

Examples of binders employed in the present invention can be given as follows: polystyrene, polyvinylalcohol, polyvinylpyrrolidone, polyvinylbutyral, polyester, polycabonate, nitrocellulose, cellulose acetate, acylonitrile-butadiene-styrene resin, silicone varnish, EB-hardened resin and UV-hardened resin.

Near-infrared absorbing materials other than new indoaniline metal complexes according to the present invention, can also be employed in the present invention. Any compound capable of converting near-infrared laser rays into heat is available for a near-infrared absorbing material in the present invention. Specific examples are immonium compounds such as IRG002 and IRG022 (trade names; available from Nippon Kayaku K.K.), dithiol nickel complexes such as NKX-113, NKX-114 and NKX-1199 (trade names; available from Nippon Kankoh-Shikiso Kenkyusho Co., Ltd.), cyanine dyes such as 1,1,5,5-tetrakis (p-dimethyl-aminophenyl)-3-methoxy-1,4-pentadiene toluene and NK-2014 (trade name; available from Nippon Kankoh-Shikiso Kenkyusho Co., Ltd.), squalerium dyes, naphthoquinone dyes, phthalocyanine dyes and naphthalocyanine dyes.

For improvement in the stability and light resistance of a transparent recording medium, singlet oxygen quenchers comprising transition metal chelate compounds such as acetylacetonate chelate, bisphenyl dithiol, salicylaldoxime, bisdithio-α-diketone may be contained with near-infrared absorbing materials.

Recording onto a transparent recording medium according to the present invention can be carried out also by means of a thermal head, but more advantageously by means of laser rays with respect to printing speed, image resolution and the like. Employed as a laser source in the present invention are gas lasers such as $N_2$, He-Cd, Ar and He-Ne, solid lasers such as ruby, semiconductor lasers such as Ga-As, and dye lasers, but semiconductor lasers are preferable especially with respect to light weight, easy handling, small size and the like. A clear record having a sufficiently high recording density can be obtained on a transparent recording medium even by using a semiconductor near-infrared laser with the low output of approx. several tens of mW.

The typical composition for producing a recording layer of a transparent recording medium according to the present invention comprises 3–30 parts of a developer, 3–30 parts of an organic acid metal salt or leuco dye, 3–30 parts of a binder and 0.001–1 parts of a near-infrared absorbing material. A solution of these components dissolved in a solvent to contain 10–30% of solid portions is applied to a transparent supporting member and dried, so that a transparent recording medium can be obtained. In addition, recording layers may be provided on both sides of the supporting member if necessary. The transparent recording medium according to the present invention prepared in this manner is of use as a masking material for print platemaking, an OHP film, a slide film, duplicating draft or a photomask for manufacturing the circuit pattern of a resin wiring board or integrated circuit.

Recently, the direct platemaking method has been developed for directly making a printing plate outputting an image or character designed on a computer without use of a draft film. Simplified steps for printing have enabled the time required for printing to be greatly shortened. However, in the field of general commercial printing, especially offset printing, the platemaking step using a draft film is employed in leading methods, in which a silver salt photography film is employed as a masking material for platemaking. The silver salt photography method, though good in image quality, has problems such as disposal of developmental process liquid, and therefore alternative materials to silver salt photograph are sought for. Because of being free from the above-mentioned problems, a transparent recording medium is useful as an alternative to silver salt photography film. The present inventive method for making a plate by using a transparent recording medium in printing an image onto a presensitized aluminum plate (PS plate) for offset printing is almost the same as the conventional method for making a plate by using a silver salt photographic film. After superimposing a transparent recording medium according to the present invention on a PS plate, an image is exposed by irradiating a light source such as a tungsten lamp, halogen lamp, xenon lamp and mercury lamp from the side of the transparent recording medium, so that a plate for offset printing can be obtained.

A new indoaniline metal complex according to the present invention is useful also as a near-infrared absorbing material, especially as an element for efficiently converting near-infrared laser rays into heat used in an optical recording medium such as optical disk. With an elevating molar extinction coefficient of an indoaniline metal complex, the efficiency of converting near-infrared laser rays into heat increases, so that an image with a sufficiently high recording density can be obtained on a transparent recording medium in a small consumed amount by using even low-output near-infrared laser rays. With the new indoaniline metal complexes according to the present invention, the maximum wavelength of absorption shifts to longer wavelengths, the molar extinction coefficient also rises sharply and the efficiency of converting near-infrared laser rays into heat is greatly improved as compared with a metal-contained indoaniline-type compounds described in Japanese Patent Laid-Open (ko-kai) 227569/1988.

An optical recording medium manufactured by using a new indoaniline metal complex according to the present invention comprises materials similar to those of a transparent recording medium. A substrate, binder, singlet oxygen quencher, other series of mixible coloring substances and the like are used in common. Film forming can be executed by a general film-forming technique such as vacuum evaporation, sputtering, doctor blade, cast, spinner or soaking.

In addition to a transparent recording medium, masking material for print platemaking, optical recording medium, new indoaniline metal complexes represented by the general formula (1) or (2) serve also as green-type coloring substance, coloring substance for heat-sensitive transcription, coloring substance for ink-jet printers, heat ray shielding agents, safety filters for sensitive materials, cut filters for semiconductor elements, color filters, liquid crystals, antihalation material for sensitive materials, optical cards, photopolymerization initiators, physiological activating substances and medicaments. In addition, reaction intermediates, new indoaniline metal complexes represented by the general formula (3) or (4) serve also as blue-type coloring substance, green-type coloring substance, coloring substance for heat-sensitive transcription, coloring substance for ink-jet printer, heat rays shielding agent, safety filters for sensitive materials, cut filters for semiconductor elements, color filters, liquid crystals, antihalation material for sensitive materials, optical cards, photopolymerization initiators, physiological activating substances and medicaments. In addition, reaction intermediates, 4-hydroxyphenanthoridine compounds represented by the general formula (6) and 4-hydroxyacridine derivatives represented by the general formula (7) are not only used as raw materials of dyes or pigments but also are utilized as physiological activating substances and medicaments.

EXAMPLES

Hereinafter, the present invention will be described in detail by referring to prepared examples and examples of compounds according to the present invention but is not restricted by these prepared examples and examples.

Example 1: Preparation of Indoaniline Metal Complexes with the Phenanthridine Skeleton Prepared Example 1-1: Preparation of the Indoaniline Metal Complex Described in the Exemplified Compound 1-1

Synthesis was carried out in accordance with the following reaction scheme.

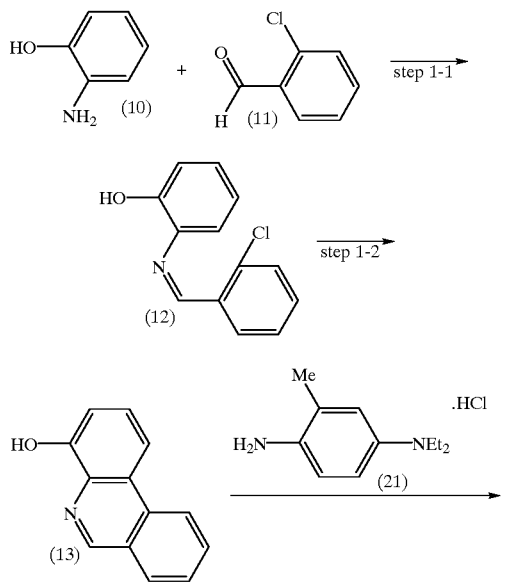

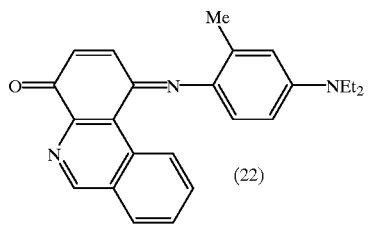

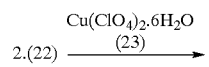

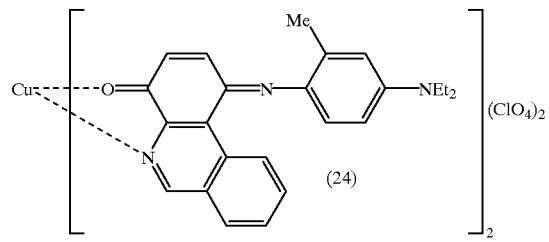

[1-1-1] Synthesis of N-(2-chlorobenzylidene)-2'-hydoroxyaniline (12)

A mixed solution comprising 12.00 g of o-aminophenol (10), 14.06 g of 2-chlorobenzaldehyde (11) and 100 ml of ethanol was allowed to react at 75° C. for a period of 5 hr. After the completion of the reaction, the ethanol was distilled away. After purifying the residue by column chromatography, 22.19 g of yellow crystal of N-(2-chlorobenzylidene)-2'-hydroxyaniline (12) was obtained on recrystallization by hexane-chloroform (yield 95.8%).

Analytical Data m.p.=94.0(° C.)

$^1$H-NMR (ppm, ref.-TMS, CDCl$_3$) 9.14(s,1 H), 8.20(dd, 1 H, J=7.2, 2.1 Hz), 7.44-7.32(m, 4 H), 7.23(dd, 1 H, J=7.0, 1.4 Hz) 7.19(d, 1 H, J=1.2 Hz), 7.02(d, 1 H, J=7.8 Hz), 6.92(t, 1 H, J=7.5 Hz) $^{13}$C-NMR (ppm, ref.-TMS, CDCl$_3$) 153.4, 152.6, 136.2, 135.4, 132.9, 132.3, 130.1, 129.5, 128.3, 127.1, 120.2, 116.2, 115.2

IR (cm$^{-1}$, KBr) 3420, 1616, 1597, 1582, 1561, 1484, 1438, 1372, 1271, 1250, 1233, 1211, 1174, 1147, 1050, 1027, 964, 934, 879, 855, 795, 759, 739, 699, 572, 517, 499, 472, 454

MS (FAB, NBA)

m/z=232 (M$^+$+1)

Figure 2:
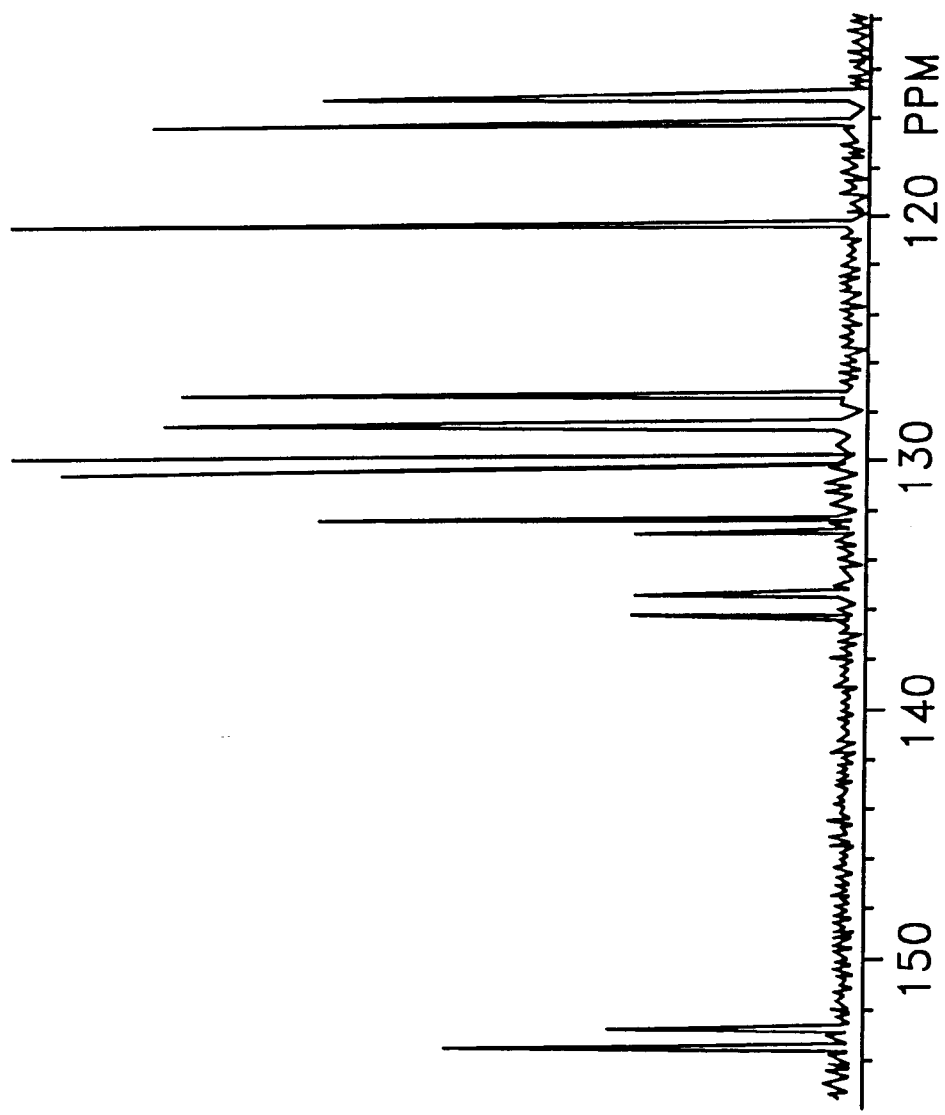
FIG. 2 is a spectral chart of $^{13}$C-NMR for N-(2-chlorobenzylidene)-2'-hydroxyaniline (12) obtained in Prepared Example 1-1-1.

FIGS. 1 and 2 show spectral charts of $^1$H-NMR and $^{13}$C-NMR.

[1-1-2] Synthesis of 4-hydroxyphenanthridine (13)

After putting 4.3 g of metal potassium and 1 mg of iron nitrate enneahydrate into 150 ml of liquid ammonium, reaction was allowed to proceed at −35° C. for a period of one hour with 3.85 g of N-(2-chlorobenzylidene)-2'-hydroxyaniline (12) added. After the completion of the reaction, ammonium was removed. After purifying the residue by column chromatography, 1.02 g of pale yellow crystal of 4-hydroxyphenanthridine (13) was obtained on recrystallization by ethyl acetate (yield 31.5%).

Analytical Data m.p.=191.0(° C.)

$^1$H-NMR (ppm, ref.-TMS, CDCl$_3$) 9.84(br, 1 H), 9.32(s,1 H), 8.75(d, 1 H, J=8.3 Hz), 8.24(d, 1 H, J=8.0 Hz), 8.18(d, 1 H, J=8.0 Hz), 7.93(t, 1 H, J=7.7 Hz), 7.79(t, 1 H, J=7.6 Hz) 7.56(t, 1 H, J=8.0 Hz), 7.16(d, 1 H, J=8.0 Hz) $^{13}$C-NMR (ppm, ref.-TMS, CDCl$_3$) 154.0, 150.9, 133.5, 131.9, 131.4, 128.9, 128.1, 127.8, 126.2, 124.5, 122.6, 112.7, 112.3

IR (cm$^{-1}$, KBr) 3313, 1615, 1581, 1526, 1492, 1470, 1442, 1410, 1349, 1318, 1295, 1260, 1213, 1170, 1061, 893, 770, 752, 730, 658, 553

MS (FAB, NBA)

m/z=196 (M$^+$+1)

Figure 3:
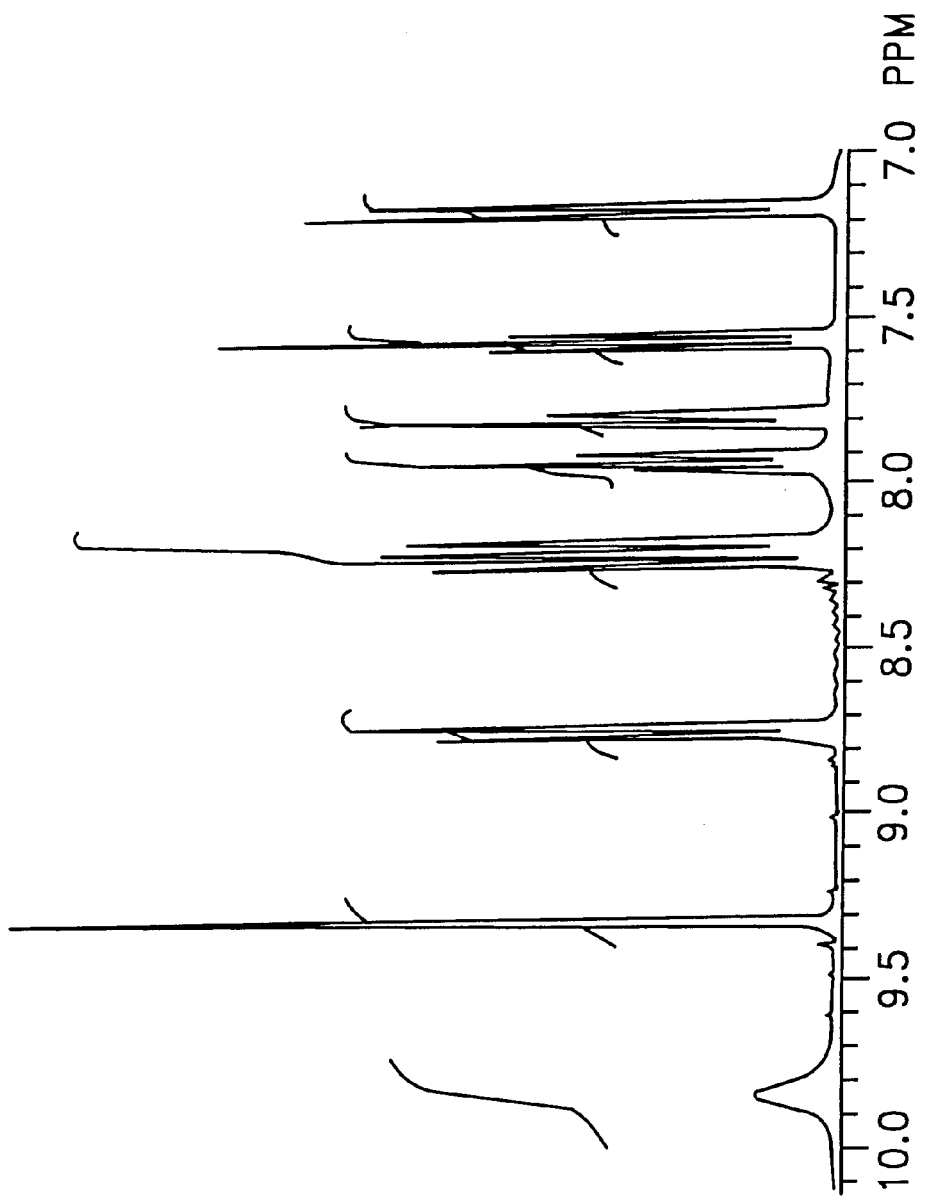
FIG. 3 is a spectral chart of $^1$H-NMR for 4-hyroxyphenanthridine (13) obtained in Prepared Example 1-1-2.
Figure 4:
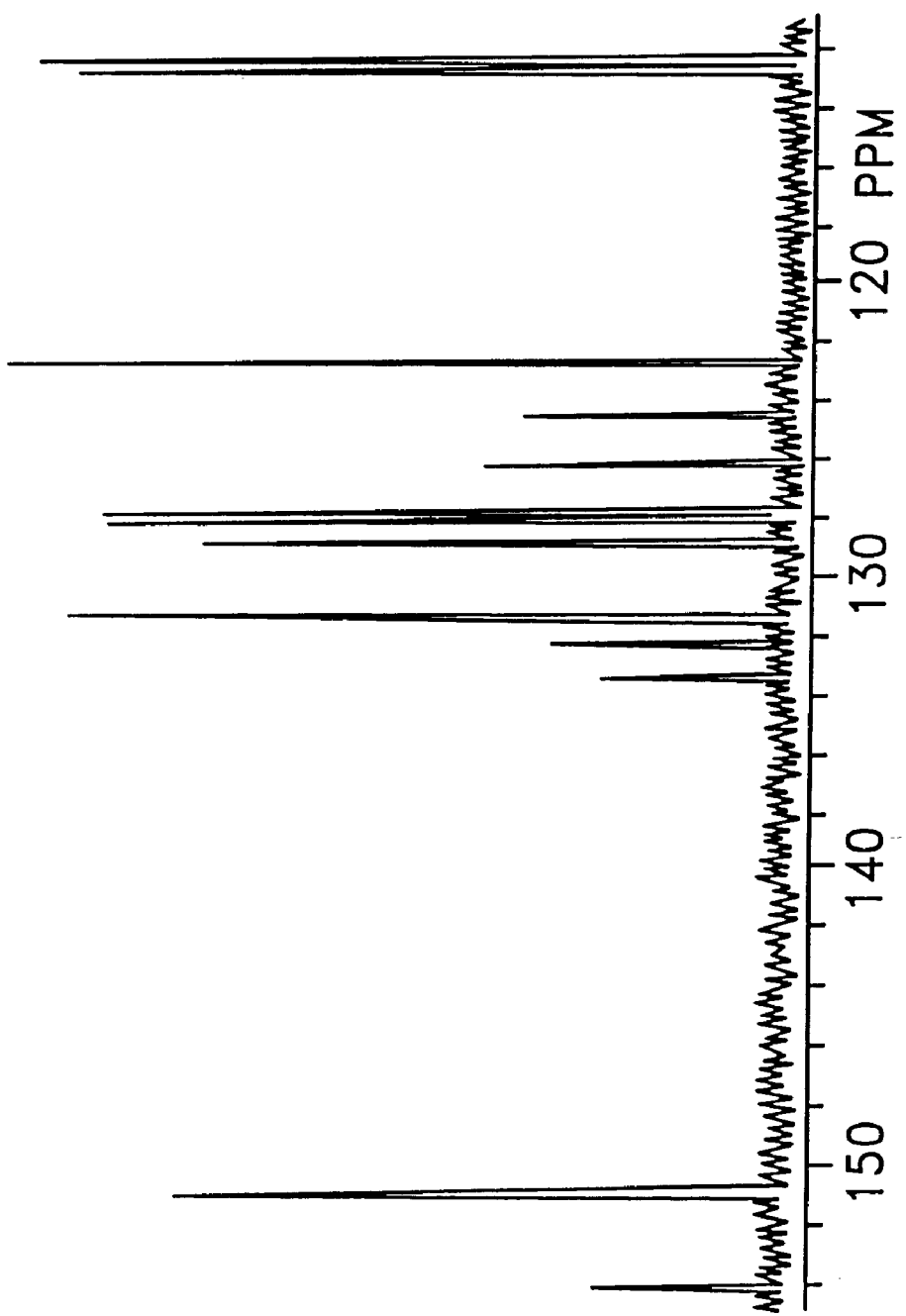
FIG. 4 is a spectral chart of $^{13}$C-NMR for 4-hyroxyphenanthridine (13) obtained in Prepared Example 1-1-2.

FIGS. 3 and 4 show spectral charts of $^1$H-NMR and $^{13}$C-NMR, respectively.

[1-1-3] Synthesis of the Indoaniline (22) Described in the Exemplified Compound 3-1

A mixture comprising 390 mg of 4-hydroxyphenanthridine (13), 430 mg of 2-amino-5-diethylaminotoluene hydrochloride (21) and 15 ml of ethanol was stirred at 20° C. and a solution comprising 1.02 g of silver nitrate dissolved in 4.5 ml of water was added thereto drop-by-drop. Then, 1.7 ml of 25% ammonia solution was added and the reaction was allowed to proceed at 20° C. for a period of 24 hr. After the completion of the reaction, the reacted solution was introduced into water. After extraction by ethyl acetate, the extract was concentrated. After purification by column chromatography, 259 mg of deep blue crystal of indoaniline (22) was obtained on recrystallization by hexane-ethyl acetate (yield 35.1%).

Analytical Data m.p.=182.5(° C.)

$^1$H-NMR (ppm, ref.-TMS, CDCl$_3$) 10.07(d, 1 H, J=8.7 Hz), 9.43(s,1 H), 8.06(d, 1 H, J=6.1 Hz), 7.86(t, 1 H, J=7.8 Hz), 7.75(t, 1 H, J=7.2 Hz), 7.55(d, 1 H, J=10.2 Hz) 6.83(d, 1 H, J=10.4 Hz), 6.74(br, 1 H) 6.69(d, 1 H, J=8.6 Hz) 6.59(br, 1 H), 3.44(quartet, 4 H, J=7.0 Hz), 2.48(s, 3 H), 1.24(t, 6 H, J=7.0 Hz)

IR (cm$^{-1}$, KBr) 3423, 2964, 2923, 1654, 1597, 1525, 1500, 1458, 1394, 1372, 1353, 1297, 1263, 1237, 1198, 1159, 1146, 1111, 1086, 1030, 997, 922, 841, 812, 753, 669, 617

MS (FAB, NBA)

m/z=370 (M$^+$+1)

Figure 5:
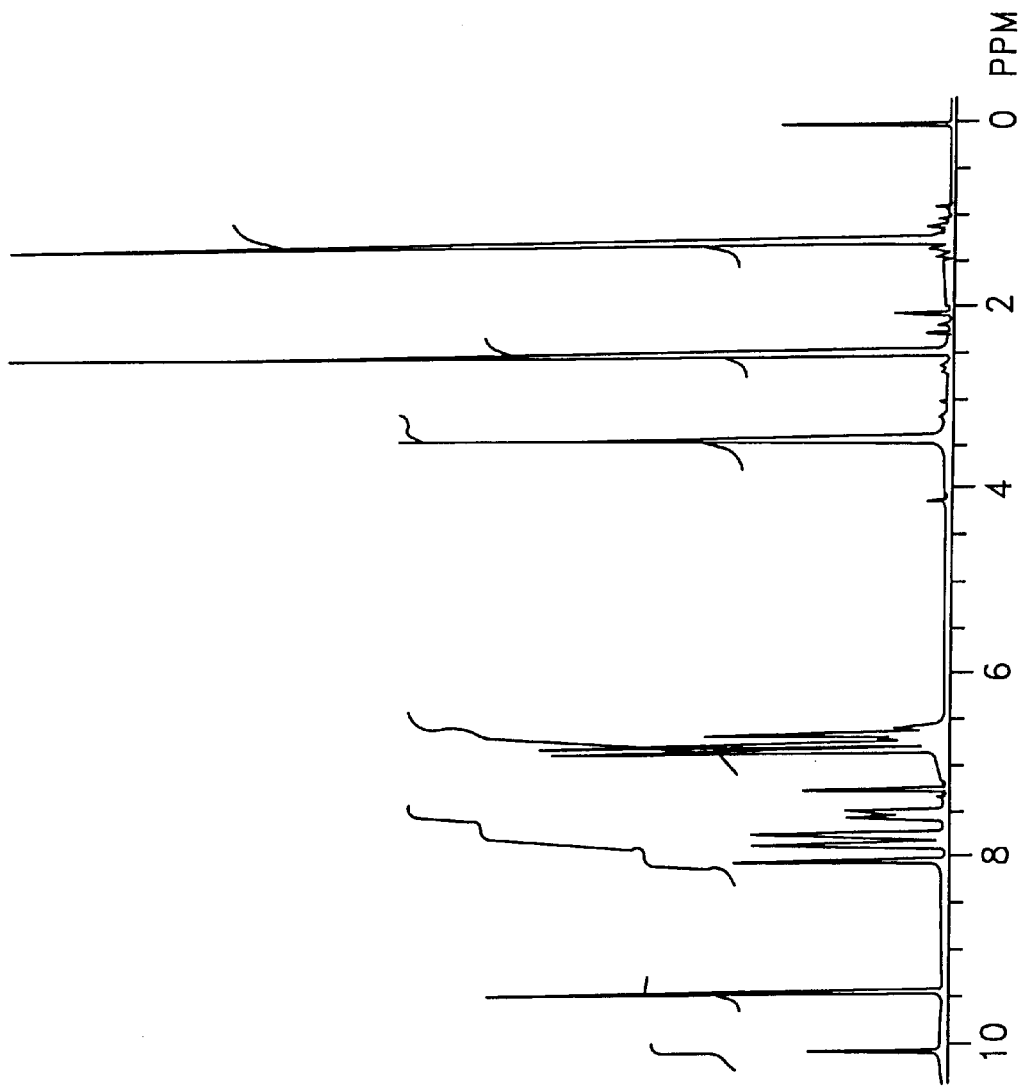
FIG. 5 is a spectral chart of $^1$H-NMR for indoaniline (22) obtained in Prepared Example 1-1-3.

FIG. 5 shows a spectral chart of $^1$H-NMR. The visible to near-infrared absorption spectrum (ethanol solution) had a maximum wavelength of absorption of 664 nm (molar extinction coefficient=22,000).

[1-1-4] Synthesis of the Indoaniline Metal Complex (24) Described in the Exemplified Compound 1-1

With 5 ml of aqueous solution containing 210 mg of copper perchlorate hexahydrate (23) added to 10 ml of ethanol solution containing 100.6 mg of indoaniline (22), reaction were allowed to proceed at 20° C. for a period of 2 hr. After the completion of the reaction, the precipitated crystals were taken out by filtration and washed with a small amount of water and ethanol, followed by 4-hr reduced-pressure drying to obtain 136.4 mg of black crystal of indoaniline metal complexe (24) (yield 100%).

Analytical Data m.p.=300(° C.) or higher.

IR (cm$^{-1}$, KBr) 3425, 1621, 1588, 1572, 1519, 1483, 1449, 1440, 1408, 1382, 1327, 1279, 1242, 1193, 1172, 1146, 1089, 1011, 989, 922, 874, 849, 829, 805, 758, 739, 674, 645, 612, 507, 455

Figure 6:
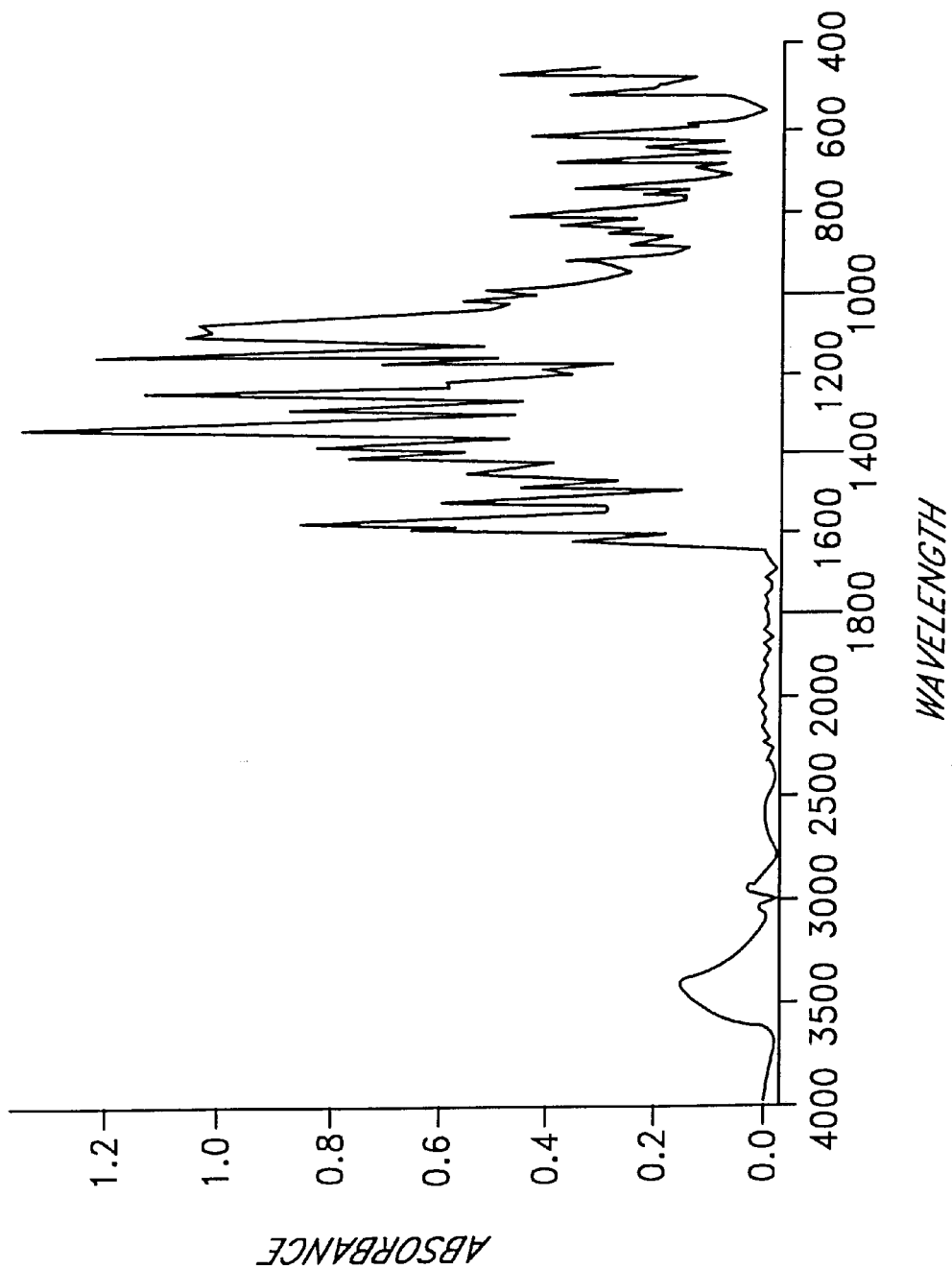
FIG. 6 is a chart of IR spectrum for the indoaniline metal complex (24) obtained in Prepared Example 1-1-4.
Figure 7:
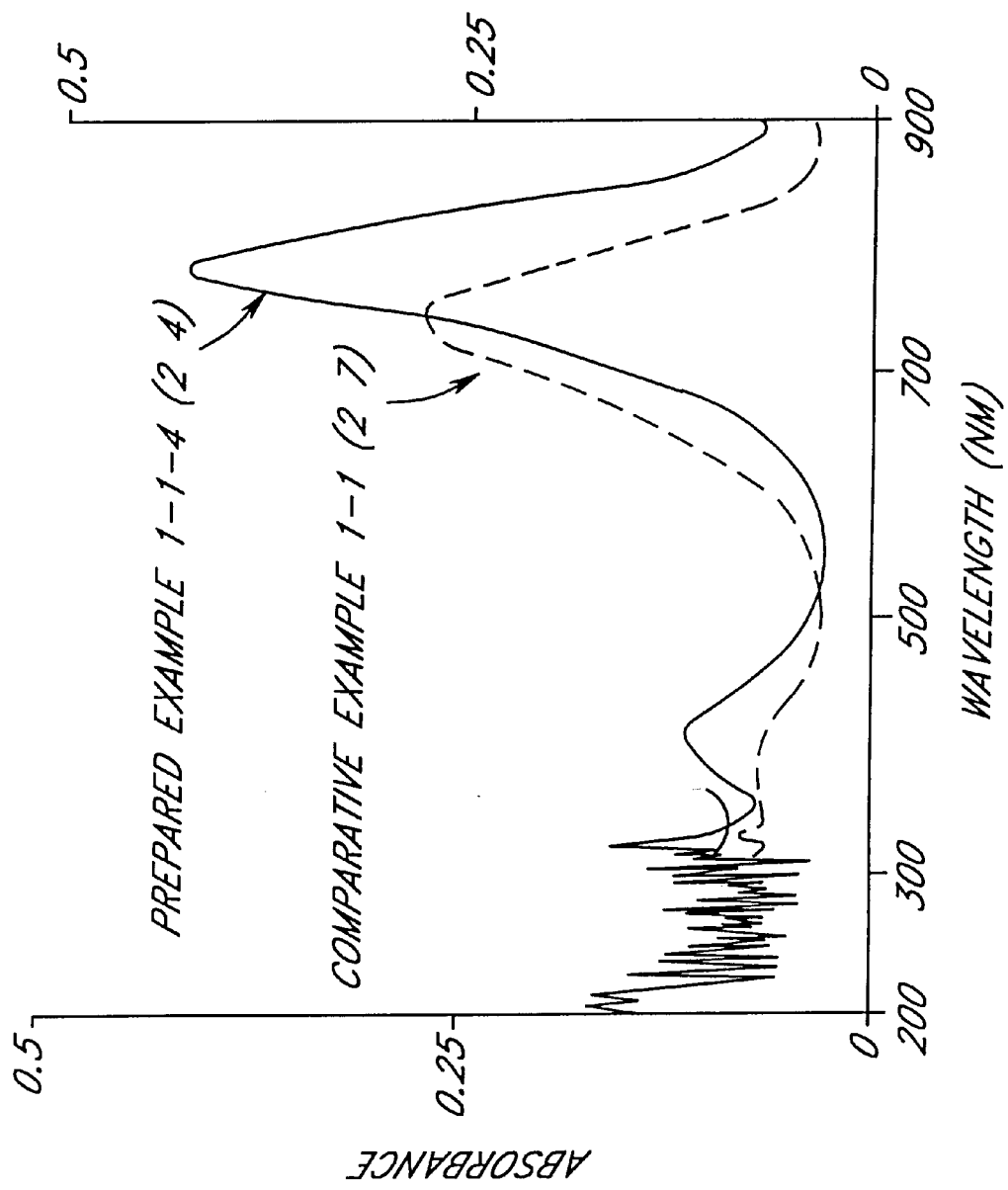
FIG. 7 is a chart of visible to near-infrared absorption spectrum for the indoaniline metal complex (24) obtained in Prepared Example 1-1-4 and the indoaniline metal complex (27) obtained in Comparative Example 1-1, where the ordinate represents an absorbance and the abscissa represents a wavelength (nm).

FIG. 6 shows a spectral chart of IR. The visible to near-infrared absorption spectrum (acetone solution) had a maximum wavelength of absorption 795 nm (molar extinction coefficient=163,000).

Prepared Example 1-2: Preparation of the Indoaniline Metal Complex Described in the Exemplified Compound 1-2

[1-2-1] Synthesis of the Indoaniline Described in the Exemplified Compound 3-2

While stirring a mixture comprising 207 mg of 4-hydroxyphenanthridine (13), 237 mg of N,N-diethyl-p-phenylenediamine and 6.8 ml of ethanol at 20° C., a solution comprising 170 mg of silver nitrate dissolved in 0.75 ml of water was added thereto drop-by-drop. Next, with 0.85 ml of 25% ammonia solution added to the mixture, reaction was allowed to proceed at 20° C. for a period of 1.5 hr. Furthermore, a solution comprising 340 mg of silver nitrate dissolved in 1.5 ml of water was added thereto drop-by-drop and the mixed solution was allowed to react at 20° C. for a period of 3 hr. After the completion of the reaction, the reacted solution was introduced into water. After extraction by chloroform, the extract was concentrated. After purification by silica gel column chromatography, 129 mg of indoaniline described in the exemplified compound 3-2 was obtained (yield 36.2%).

Analytical Data m.p.=176.7–178.2(° C.)

$^1$H-NMR (ppm, ref.-TMS, CDCl$_3$) 9.98(d, 1 H, J=8.6 Hz), 9.43(s, 1 H), 8.06(d, 1 H, J=8.0 Hz), 7.87(ddd, 1 H, J=8.6, 7.9, 1.2 Hz), 7.76(dd, 1 H, J=8.0, 7.9 Hz), 7.59(d, 1 H, J=10.2 Hz) 7.10(d, 2 H, J=8.8 Hz), 6.84(d, 1 H, J=10.2 Hz) 6.82(d, 2 H, J=8.8 Hz), 3.46(quartet, 2 H, J=6.9 Hz), 1.26(t, 3 H, J=6.9 Hz) $^{13}$C-NMR (ppm, ref.-TMS, CDCl$_3$) 184.9, 155.4, 142.7, 133.0, 132.4, 131.4, 130.7, 129.5, 129.1, 128.5, 127.6, 126.7, 125.3, 123.0, 119.4, 112.0, 45.1, 12.6

IR (cm$^{-1}$, KBr) 2967, 1651, 1590, 1508, 1397, 1349, 1299, 1269, 1087, 997, 851, 818, 795, 760

MS (FAB, NBA)

m/z=356 (M$^+$+1)

The visible to near-infrared absorption spectrum (acetone solution) has a maximum wavelength of absorption 615.4 nm (molar extinction coefficient=16,500).

[1-2-2] Preparation of the Indoaniline Metal Complex Described in the Exemplified Compound 1-2

With 1.87 ml of aqueous solution containing 93.4 mg of copper perchlorate hexahydrate (23) added to 3 ml of ethanol solution containing 35.5 mg of indoaniline described in the exemplified compound 3-2, reaction was allowed to proceed at 20° C. for a period of 5 hr. After the completion of the reaction, the precipitated crystals were taken out by filtration and washed with a small amount of water and ethanol, followed by 4-hr reduced-pressure drying to obtain 44.0 mg of deep green crystal of indoaniline metal complexe described in the exemplified compounds 1-2 (yield 90.3%).

Analytical Data m.p.=300(° C.) or higher

IR (cm$^{-1}$, KBr) 1573, 1425, 1382, 1330, 1277, 1245, 1136, 1072, 1014, 823, 738, 618

The visible to near-infrared absorption spectrum (acetone solution) has a maximum wavelength of absorption 791 nm (molar extinction coefficient=98,700).

Prepared Example 1-3: Preparation of the Indoaniline Metal Complex Described in the Exemplified Compound 1-7

[1-3-1] Synthesis of the Indoaniline Described in the Exemplified Compound 3-7

While stirring a mixture comprising 228 mg of 4-hydroxyphenanthridine (13), 224 mg of N,N-di-sec-butyl-p-phenylenediamine and 7.5 ml of ethanol at 20° C., a solution comprising 187 mg of silver nitrate dissolved in 0.82 ml of water was added thereto drop-by-drop. Next, with 0.94 ml of 25% ammonia solution added to the mixture, reaction was allowed to proceed at 20° C. for a period of 2 hr. Furthermore, a solution comprising 375.5 mg of silver nitrate dissolved in 1.65 ml of water was added thereto drop-by-drop and reaction was allowed to proceed at 20° C. for a period of 12 hr. After the completion of the reaction, the reacted solution was introduced into water. After extraction by chloroform, the extract was concentrated. On purification by silica gel column chromatography, 133 mg of indoaniline described in the exemplified compound 3-7 was obtained (yield 34.1%).

Analytical Data m.p.=86.8–87.5(° C.)

$^1$H-NMR (ppm, ref.-TMS, CDCl$_3$) 9.96(d, 1 H, J=8.7 Hz), 9.44(s, 1 H), 8.07(d, 1 H, J=9.4 Hz), 7.87(ddd, 1 H, J=8.7, 6.7, 1.0 Hz), 7.76(dd, 1 H, J=9.4, 6.7 Hz), 7.58(d, 1 H, J=10.4 Hz), 7.02(d, 2 H, J=8.6 Hz), 6.83(d, 1 H, J=10.4 Hz) 6.72(d, 2 H, J=8.6 Hz), 3.56-3.44(m,1 H), 1.70-1.29(m, 2H) 1.25(d, 3 H, J=6.3 Hz), 1.00(t, 3 H, J=7.4 Hz) $^{13}$C-NMR (ppm, ref.-TMS, CDCl$_3$) 184.8, 155.5, 154.8, 147.3, 142.6, 139.8, 132.9, 132.5, 131.3, 130.7, 130.4, 129.5, 129.1, 128.5, 126.7, 125.0, 113.5, 50.3, 29.6, 20.2, 10.4

IR (cm$^{-1}$, KBr) 3368, 2979, 1637, 1605, 1590, 1477, 1422, 1339, 1269, 1163, 1139, 1090, 996, 833, 814, 756

MS (FAB, NBA)

m/z=356 (M$^+$+1)

The visible to near-infrared absorption spectrum (acetone solution) had a maximum wavelength of absorption 599 nm (molar extinction coefficient=11,220).

[1-3-2] Preparation of the Indoaniline Metal Complex Described in the Exemplified Compound 1-7

With 1.87 ml of aqueous solution containing 78.4 mg of copper perchlorate hexahydrate (23) added to 3 ml of ethanol solution containing 30.0 mg of indoaniline described in the exemplified compound 3-7, reaction was allowed to proceed at 20° C. for a period of 2 hr. After the completion of the reaction, the precipitated crystals were as taken out by filtration and washed with a small amount of water and ethanol, followed by 4-hr reduced-pressure drying to obtain 12.6 mg of black crystal of the indoaniline metal complex described in the exemplified compound 1-7 (yield 30.7%).

Analytical Data m.p.=300(° C.) or higher

IR (cm$^{-1}$, KBr) 3228, 3069, 1589, 1573, 1515, 1449, 1384, 1330, 1227, 1246, 1169, 1139, 1104, 1016, 823, 740, 670, 618, 513, 456

The visible to near-infrared absorption spectrum (acetone solution) had a maximum wavelength of absorption 774 nm (molar extinction coefficient=104,000).

Prepared Example 1-4: Preparation of the Indoaniline Metal Complex Described in the Exemplified Compound 1-10

[1-4-1] Synthesis of N-acetyl-N',N'-di(2-ethylhexyl)-p-phenylenediamine

A mixed solution comprising 1.00 g of p-aminoacetanilide, 16.72 g of 2-ethylhexylbromide, 4.59 g of sodium carbonate and 20 ml of methylcellosolve is allowed to react at 113° C. for a period of 24 hr. After the completion of the reaction, the reacted solution was introduced into water and the product was extracted by ethyl acetate. After ethyl acetate was distilled away, the residue was purified by silica gel column chromatography, 1.17 g of oil of N-acetyl-N',N'-di(2-ethylhexyl)-p-phenylenediamine was obtained (yield 48.9%).

Analytical Data $^1$H-NMR (ppm, ref.-TMS, CDCl$_3$) 7.25(d, 2 H, J=8.8 Hz), 7.07(s, 1 H), 6.60(d,2 H, J=9.0 Hz), 3.21-3.12(m, 4 H), 2.12(s, 3H), 1.76(br, 1 H), 1.40-1.20(m, 16 H), 0.88(t, 6 H, J=6.4 Hz), 0.86(t, 6 H, J=7.2 Hz) $^{13}$C-NMR (ppm, ref.-TMS, CDCl$_3$) 168.1, 145.9, 126.1, 122.2, 113.1, 56.6, 36.7, 30.7, 28.7, 24.2, 23.9, 23.2, 14.1, 10.7

IR (cm$^{-1}$, KBr) 3289, 2959, 2928, 2858, 1657, 1601, 1538, 1516, 1461, 1417, 1369, 1322, 1269, 1227, 1186, 813, 516

MS (FAB, NBA)

m/z=375 (M$^+$+1)

[1-4-2] Preparation of N,N-di(2-ethylhexyl)-p-phenylenediamine

A mixed solution comprising 8 ml of 30% sodium hydroxide solution, 1.012 g of N-acetyl-N',N'-di(2-ethylhexyl)-p-phenylenediamine and 10 ml of ethanol was allowed to react at 75° C. for a period of 5 hr. After the completion of the reaction, the reacted solution was introduced into water and the product was extracted by ethyl acetate. After ethyl acetate was distilled away, the residue was purified by silica gel column chromatography to obtain 501 mg of oil of N,N-di(2-ethylhexyl)-p-phenylenediamine (yield 53.4%).

Analytical Data $^1$H-NMR (ppm, ref.-TMS, CDCl$_3$) 6.62(s, 4 H), 3.55(br, 4 H), 1,63(br, 2 H) 1.45–1.20(m, 16 H), 0.88(t, 6 H, J=6.4 Hz), 0.84(t, 6 H, J=7.4 Hz) $^{13}$C-NMR (ppm, ref.-TMS, CDCl$_3$) 143.2, 137.0, 116.9, 116.7, 57.8, 36.9, 30.8, 28.8, 24.0, 23.2, 14.1, 10.7

IR (cm$^{-1}$, KBr) 3446, 3355, 2958, 2928, 2871, 2858, 1681, 1599, 1557, 1513, 1459, 1376, 1363, 1310, 1268, 1227, 1179, 1155, 1114, 1041, 938, 818, 766, 727, 667, 512

MS (FAB, NBA)

m/z=333 (M$^+$+1)

[1-4-3] Synthesis of the Indoaniline Described in the Exemplified Compound 3-10

While stirring a mixture comprising 267 mg of 4-hydroxyphenanthridine (13), 430 mg of N,N-di(2-ethylhexyl)-p-phenylenediamine and 8 ml of ethanol at 20° C., a solution comprising 219 mg of silver nitrate dissolved in 0.9 ml of water was added thereto drop-by-drop. 30 min later, 1.1 ml of 25% ammonia solution was added to the mixture, further a solution comprising 438 mg of silver nitrate dissolved in 1.7 ml of water was added thereto drop-by-drop and reaction was allowed to proceed at 20° C. for a period of 1.5 hr. After the completion of the reaction, the reacted solution was introduced into water. After extraction by chloroform, the extract was concentrated. On purification by silica gel column chromatography, 141 mg of indoaniline described in the exemplified compound 3-10 was obtained (yield 20.8%).

Analytical Data m.p.=87.6–88.0(° C.)

$^1$H-NMR (ppm, ref.-TMS, CDCl$_3$) 10.02(dd, 1 H, J=8.8, 1.0 Hz), 9.41(d, 1 H, J=0.6 Hz), 8.05(dd, 1 H, J=8.0, 0.9 Hz), 7.86(ddd, 1 H, J=8.8, 7.2, 1.6 Hz), 7.75(ddd, 1 H, J=8.0, 7.2, 1.0 Hz), 7.65(d, 1 H, J=10.3 Hz), 7.10(d, 2 H, J=9.0 Hz), 6.85(d, 1 H, J=10.3 Hz), 6.78(d, 2 H, J=9.0 Hz), 3.36-3.29 (m,4 H), 1.88-1.83(m, 2 H) 1.45-1.23(m, 16 H), 0.98-0.90 (m, 12 H) $^{13}$C-NMR (ppm, ref.-TMS, CDCl$_3$) 185.0, 155.2, 153.8, 148.1, 142.6, 138.3, 133.0, 132.3, 131.5, 130.3, 129.6, 129.0, 128.4, 126.7, 125.5, 112.8, 56.5, 37.1, 30.7, 28.7, 24.0, 23.2, 14.1, 10.7

IR (cm$^{-1}$, KBr) 2957, 2926, 2870, 1643, 1590, 1507, 1364, 1295, 1232, 1180, 1139, 1084, 815

MS (FAB, NBA)

m/z=525 (M$^+$+1)

The visible to near-infrared absorption spectrum (acetone solution) had a maximum wavelength of absorption 622.6 nm (molar extinction coefficient=16,760).

[1-4-4] Preparation of the Indoaniline Metal Complex Described in the Exemplified Compound 1-10

With 1.9 ml of aqueous solution containing 89.1 mg of copper perchlorate hexahydrate (23) added to 4.3 ml of ethanol solution containing 50.0 mg of indoaniline described in the exemplified compound 3-10, reaction was allowed to proceed at 20° C. for a period of 6 hr. After the completion of the reaction, the precipitated crystals were taken out by filtration and washed with a small amount of water and ethanol, followed by 4-hr reduced-pressure drying to obtain 57.0 mg of green crystal of the indoaniline metal complex described in the exemplified compound 1-15 (yield 91.2%).

Analytical Data m.p.=300(° C.) or higher

IR (cm$^{-1}$, KBr) 2956, 2927, 1575, 1392, 1350, 1134, 1095, 1016, 826, 736, 622

The visible to near-infrared absorption spectrum (acetone solution) had a maximum wavelength of absorption 809.4 nm (molar extinction coefficient=151,500).

Prepared Examples 1-5: Preparation of the Indoaniline Metal Complex Described in the Exemplified Compound 1-11

[1-5-1] Synthesis of N-acetyl-N',N'-dihexadecyl-p-phenylenediamine

A mixed solution comprising 1.00 g of p-aminoacetanilide, 20.34 g of hexadecylbromide, 3.53 g of sodium carbonate and 20 ml of methylcellosolve is allowed to react at 113° C. for a period of 9 hr. After the completion of the reaction, the reacted solution was introduced into water and the product was extracted by ethyl acetate. After ethyl acetate was distilled away, the residue was purified by silica gel column chromatography, 3.95 g of N-acetyl-N',N'-dihexadecyl-p-phenylenediamine crystal was obtained on recrystallization by dichloromethane (yield 99.0%).

Analytical Data m.p=56.3–57.3(° C.).

$^1$H-NMR (ppm, ref.-TMS, CDCl$_3$) 7.25(d, 2 H, J=8.7 Hz), 7.05(s, 1 H), 6.57(d, 2 H, J=8.9 Hz), 3.21(t, 4 H, J=7.6 Hz), 2.12(s, 3 H) 1.54(br, 4 H) 1.26(br, 52 H), 0.88(t, 6 H, J=6.6 Hz) $^{13}$C-NMR. (ppm, ref.-TMS, CDCl$_3$) 168.1, 145.7, 126.1, 122.6, 112.0, 51.3, 31.9, 29.7, 29.4, 27.2, 24.2, 22.7, 14.1

IR (cm$^{-1}$, KBr) 3278, 2920, 2851, 1654, 1555, 1541, 1514, 1468, 1363, 1318

MS (FAB, NBA)

m/z=599 (M$^+$+1)

[1-5-2] Synthesis of N,N-dihexadecyl-p-phenylenediamine

A mixed solution comprising 5 ml of 30% sodium hydroxide solution, 3.257 g of N-acetyl-N',N'-dihexadecyl-p-phenylenediamine and 10 ml of ethanol was allowed to react at 75° C. for a period of 9 hr. After the completion of the reaction, the reacted solution was introduced into water and the product was extracted by ethyl acetate. After ethyl acetate was distilled away, the residue was purified by silica gel column chromatography and 2.138 g of N,N-dihexyadecyl-p-phenylenediamine crystal was obtained on recrystallization by dichloromethane (yield 70.6%).

Analytical Data m.p=43.0–44.0(° C.)

$^1$H-NMR (ppm, ref.-TMS, CDCl$_3$) 6.64(d, 2 H, J=8.9 Hz), 6.58(d, 2 H, J=9.0 H), 3.11(t, 4 H, J=7.5 H), 1.49(br, 4 H), 1.26(br, 52 H) 0.88(t, 6 H, J=6.7 Hz) $^{13}$C-NMR (ppm, ref.-TMS, CDCl$_3$) 142.5, 136.8, 116.9, 115.5, 52.3, 32.0, 29.7, 29.4, 27.3, 22.7, 14.1

IR (cm$^{-1}$, KBr) 3433, 3207, 2919, 2851, 1637, 1612, 1512, 1467, 1363, 1275, 1089, 830, 722

MS (FAB, NBA)

m/z=557 (M$^+$+1)

[1-5-3] Synthesis of the Indoaniline Described in the Exemplified Compound 3-11

While stirring a mixture comprising 207 mg of 4-hydroxyphenanthridine (13), 557 mg of N,N-dihexadecyl-p-phenylenediamine and 6.8 ml of ethanol at 20° C., a solution comprising 170 mg of silver nitrate dissolved in 0.8 ml of water was added thereto drop-by-drop. 45 min later, 0.9 ml of 25% ammonia solution was added to the mixture, further a solution comprising 340 mg of silver nitrate dissolved in 1.5 ml of water was added thereto drop-by-drop and reaction was allowed to proceed at 20° C. for a period of 8 hr. After the completion of the reaction, the reacted solution was introduced into water. After extraction by chloroform, the extract was concentrated. On purification by silica gel column chromatography, 99.3 mg of indoaniline described in the exemplified compound 3-11 was obtained (yield 13.3%).

Analytical Data m.p.=66.3(° C.)

$^1$H-NMR (ppm, ref.-TMS, CDCl$_3$) 10.02(d, 1 H, J=8.7 Hz), 9.43(s, 1 H), 8.07(d, 1 H, J=8.0 Hz), 7.87(dd, 1 H, J=7.3, 7.3 Hz), 7.76(dd, 1 H, J=7.7, 7.0 Hz), 7.63(d, 1 H, J=10.4 Hz), 7.10(d, 2 H, J=8.9 Hz), 6.84(d, 1 H, J=10.4 Hz), 6.74(d, 2 H, J=8.9 Hz), 3.35(t, 4 H, J=7.3 Hz), 1.65(m, 4 H), 1.36-1.26(m, 52 H), 0.88(t, 6 H, J=6.2 Hz) $^{13}$C-NMR (ppm, ref.-TMS, CDCl$_3$) 185.0, 155.3, 153.9, 148.0, 142.6, 138.3, 134.2, 133.0, 132.4, 131.5, 130.4, 129.6, 129.0, 128.5, 126.8, 125.7, 118.9, 51.3, 32.0, 29.73, 29.71, 29.66, 29.57, 29.50, 29.46, 29.39, 27.43, 27.2, 22.7, 14.1

IR (cm$^{-1}$, KBr) 2919, 2850, 1650, 1591, 1508, 1465, 1398, 1372, 1305, 1093, 819

MS (FAB, NBA)

m/z=749 (M$^+$+1)

The visible to near-infrared absorption spectrum (acetone solution) had a maximum wavelength of absorption 623.4 nm (molar extinction coefficient=17,200).

[1-5-4] Preparation of the Indoaniline Metal Complex Described in the Exemplified Compound 1-11

With 1.5 ml of aqueous solution containing 80.6 mg of copper perchlorate hexahydrate (23) added to 7 ml of ethanol solution containing 65.1 mg of indoaniline described in the exemplified compound 3-11, reaction was allowed to proceed at 20° C. for a period of 12 hr. After the completion of the reaction, the precipitated crystals were taken out by filtration and washed with a small amount of water and ethanol, followed by 4-hr reduced-pressure drying to obtain 57.5 mg of green crystal of indoaniline metal complexe described in the exemplified compound 1-11 (yield 37.6%).

Analytical Data m.p.=213–215(° C.)

IR (cm$^{-1}$, KBr) 2920, 2850, 1574, 1383, 1338, 1134, 1104, 1016, 825, 741, 617

The visible to near-infrared absorption spectrum (acetone solution) had a maximum wavelength of absorption 789.8 nm (molar extinction coefficient=87,940).

Prepared Example 1-6: Preparation of the Indoaniline Metal Complex Described in the Exemplified Compound 1-15

[1-6-1] Synthesis of N-acetyl-N',N'-di(2-(2-methoxy)ethoxy)ethyl-p-phenylenediamine A mixed solution comprising 1.00 g of P-aminoacetanilide, 10.00 g of 2-chloro-2-methoxydiethyl ether, and 5.00 g of sodium carbonate is allowed to react at 150° C. for a period of 12 hr. After the completion of the reaction, the reacted solution was washed by water and purified by column chromatography, so that 1.90 g of oil of N-acetyl-N',N'-di(2-(2-methoxy)ethoxy)-ethyl-p-phenylenediamine (yield 80.3%).

Analytical Data $^1$H-NMR (ppm, ref.-TMS, CDCl$_3$) 7.44(s, 1 H), 7.27(d, 2 H, J=9.0 Hz), 6.64(d, 2 H, J=8.9 H), 3.65-3.50(m, 16 H), 2.11(s, 3 H) $^{13}$C-NMR (ppm, ref.-TMS, CDCl$_3$) 168.3, 145.0, 127.1, 122.4, 111.9, 71.9, 70.5, 68.4, 59.0, 51.0, 24.1

IR (cm$^{-1}$, KBr) 3479, 3301, 3182, 3114, 3064, 2878, 1655, 1600, 1519, 1455, 1418, 1369, 1324, 1268, 1228, 1195, 1112, 1023, 928, 846, 817, 666, 603, 522

MS (FAB, NBA)
m/z=355 (M$^+$+1)

[1-6-2] Preparation of N,N-di(2-(2-methoxy)ethoxy)ethyl-p-phenylenediamine

A mixed solution comprising 25 ml of 30% sodium hydroxide solution, 1.795 g of N-acetyl-N',N'-di(2-(2-methoxy)ethoxy)ethyl-p-phenylenediamine and 20 ml of ethanol was allowed to react at 75° C. for a period of 10 hr. After the completion of the reaction, the reacted solution was introduced into water and the product was extracted by ethyl acetate. After ethyl acetate was distilled away, the residue was purified by silica gel column chromatography to obtain 1.281 g of oil of N,N-di(2-(2-methoxy)ethoxy)ethyl-p-phenylenediamine (yield 81.0%).

Analytical Data
$^1$H-NMR (ppm, ref.-TMS, CDCl$_3$) 6.62(s, 4 H), 3.67-3.28 (m, 24 H) $^{13}$C-NMR (ppm, ref.-TMS, CDCl$_3$) 141.1, 137.2, 116.6, 114.5, 71.7, 70.2, 68.5, 58.8, 51.6
IR (cm$^{-1}$, KBr) 3427, 3350, 2876, 1650, 1635, 1558, 1517, 1472, 1456, 1360, 1274, 1197, 1108, 1027, 976, 814, 667, 517
MS (FAB, NBA)
m/z=313 (M$^+$+1)

[1-6-3] Synthesis of the Indoaniline Described in the Exemplified Compound 3-15

While stirring a mixture comprising 145 mg of 4-hydroxyphenanthridine (13), 219 mg of N,N-di(2-(2-methoxy)ethoxy)ethyl-p-phenylenediamine and 4.3 ml of ethanol at 20° C., a solution comprising 119 mg of silver nitrate dissolved in 0.5 ml of water was added thereto drop-by-drop. 30 min later, 0.6 ml of 25% ammonia solution was added to the mixture, further a solution comprising 238 mg of silver nitrate dissolved in 1.0 ml of water was added thereto drop-by-drop and reaction was allowed to proceed at 20° C. for a period of 1.5 hr. After the completion of the reaction, the reacted solution was introduced into water. After extraction by chloroform, the extract was concentrated. On purification by silica gel column chromatography, 194 mg of indoaniline described in the exemplified compound 3-15 was obtained (yield 54.9%).

Analytical Data
$^1$H-NMR (ppm, ref.-TMS, CDCl$_3$) 9.98(d, 1 H, J=8.7 Hz), 9.43(s, 1 H), 8.07(d, 1 H, J=8.0 Hz), 7.88(dd, 1 H, J=8.7, 7.6 Hz), 7.78(dd, 1 H, J=7.6, 7.0 Hz), 7.59(d, 1 H, J=10.3 Hz), 7.06(d, 2 H, J=8.7 Hz), 6.84(d, 2 H, J=8.7 Hz), 6.835(d, 1 H, J=8.7 Hz), 3.70(m, 8 H), 3.65(m, 4 H), 3.56(m, 4 H), 3.40(s, 6 H) $^{13}$C-NMR (ppm, ref.-TMS, CDCl$_3$) 185.0, 155.4, 154.7, 147.5, 142.6, 139.0, 132.9, 132.5, 131.4, 130.7, 130.3, 129.4, 129.1, 128.5, 126.7, 125.0, 112.1, 72.0, 70.7, 68.5, 59.1, 51.2
IR (cm$^{-1}$, KBr) 2878, 1651, 1591, 1508, 1393, 1353, 1240, 1138, 997, 817
MS (FAB, NBA)
m/z=504 (M$^+$+1)

The visible to near-infrared absorption spectrum (acetone solution) had a maximum wavelength of absorption 605.6 nm (molar extinction coefficient=11,700).

[1-6-4] Preparation of the Indoaniline Metal Complex Described in the Exemplified Compound 1-15

With 2 ml of aqueous solution containing 147.0 mg of copper perchlorate hexahydrate (23) added to 6 ml of ethanol solution containing 79.3 mg of indoaniline described in the exemplified compound 3-15, reaction was allowed to proceed at 20° C. for a period of 12 hr. After the completion of the reaction, the deposited crystals were taken out by filtration and washed with a small amount of water and ethanol, followed by 4-hr reduced-pressure drying to obtain 39.8 mg of brown crystals of the indoaniline metal complex described in the exemplified compound 1-15 (yield 20.0%).

Analytical Data
m.p.=300(° C.) or higher
IR (cm$^{-1}$, KBr) 1574, 1537, 1377, 1332, 1122, 1096, 1013, 824, 736, 622

The visible to near-infrared absorption spectrum (acetone solution) had a maximum wavelength of absorption 798.2 nm (molar extinction coefficient=110,200).

Prepared Examples 1-7:Preparation of the Indoaniline Metal Complex Described in the Exemplified Compound 1-25

[1-7-1] Synthesis of the Indoaniline Described in the Exemplified Compound 3-25

While stirring a mixture comprising 207 mg of 4-hydroxyphenanthridine (13), 221 mg of p-aminodiphenylamine hydrochloride and 6.8 ml of ethanol at 20° C., a solution comprising 170 mg of silver nitrate dissolved in 0.8 ml of water was added thereto drop-by-drop. 30 min later, with 0.9 ml of 25% ammonia solution having being added and moreover a solution comprising 340 mg of silver nitrate dissolved in 1.5 ml of water being dropwise added to the mixed solution, reaction was allowed to proceed at 20° C. for a period of 6 hr. After the completion of the reaction, the reacted solution was introduced into water. After extraction by chloroform, the extract was concentrated. On purification by silica gel column chromatography, 129 mg of indoaniline described in the exemplified compound 3-25 was obtained (yield 34.4%).

Analytical Data
m.p.=198.2–199.7(° C.)
$^1$H-NMR (ppm, ref.-TMS, CDCl$_3$) 9.92(d, 1 H, J=8.6 Hz), 9.46(s, 1 H), 8.08(d, 1 H, J=7.7 Hz), 7.91(dd, 1 H, J=8.6, 7.0 Hz), 7.79(dd, 1 H, J=7.7, 7.0 Hz), 7.54(d, 1 H, J=10.3 Hz), 7.35-7.30(m, 2 H), 7.27(s, 1 H), 7.21-7.04(m, 4 H), 7.09-6.95(m, 3 H), 6.85(d, 1 H, J=10.3 Hz) $^{13}$C-NMR (ppm, ref.-TMS, CDCl$_3$) 184.9, 156.6, 155.9, 142.7, 142.4, 142.4, 142.1, 132.8, 132.8, 131.6, 131.3, 130.4, 129.5, 129.3, 129.2, 128.6, 126.4, 123.4, 121.9, 118.6, 117.5
IR (cm$^{-1}$, KBr) 3281, 1642, 1578, 1510, 1492, 1458, 1412, 1309, 1234, 1162, 1137, 1091, 995, 841, 818, 805, 747, 693
MS (FAB, NBA)
m/z=376 (M$^+$+1)

The visible to near-infrared absorption spectrum (acetone solution) had a maximum wavelength of absorption 576 nm (molar extinction coefficient=10,160).

[1-7-2] Preparation of the Indoaniline Metal Complex Described in the Exemplified Compound 1-25

With 2 ml of aqueous solution containing 93.4 mg of copper perchloride hexahydrate (23) added to 3 ml of ethanol solution containing 37.5 mg of indoaniline described in the exemplified compound 3-25, reaction was allowed to proceed at 20° C. for a period of 12 hr. After the completion of the reaction, the precipitated crystals were taken out by filtration and washed with a small amount of water and ethanol, followed by 4-hr reduced-pressure drying to obtain 45.3 mg of black crystal of the indoaniline metal complex described in the exemplified compound 1-25 (yield 89.3%).

Analytical Data
m.p.=300(° C.) or higher
IR (cm$^{-1}$, KBr) 1574, 1389, 1319, 1124, 1099, 1014, 824, 740

The visible to near-infrared absorption spectrum (acetone solution) had a maximum wavelength of absorption 784 nm (molar extinction coefficient=62,700).

Prepared Example 1-8: Preparation of the Indoaniline Metal Complex Described in the Exemplified Compound 1-53

[1-8-1] Synthesis of laur-5-chloro-2-nitroanilide

After, while cooled with ice, 20 ml of benzene solution containing 7.65 g of n-lauroyl chloride was dropwise added to a mixed solution comprising 3.45 g of 5-chloro-2-nitroaniline, 1.29 g of N,N-dimethylaminopyridine, 1.58 g of pyridine and 20 ml of benzene, reaction was allowed to proceed at room temperatures for a period of 8.5 hr. After the completion of the reaction, the reacted solution is washed with 0.1 N hydrochloric acid and the solution was distilled away. On recrystallization of the precipitated crystals from hexane-ethyl acetate, 4.75 g of laur-5-chloro-2-nitroanilide crystal was obtained (yield 67.0%).

Analytic Data m.p.=66.2(° C.)

$^1$H-NMR (ppm, ref-TMS, CDCl$_3$) 10.46(s, 1 H), 8.94(d, 1 H, J=2.5 Hz), 8.17(d, 1 H, J=9.4 Hz), 7.13(dd, 1 H, J=9.4, 2.5 Hz), 2.50(t, 2 H, J=7.5 Hz), 1.75(m, 2 Hz), 1.43-1.26(m, 16 H), 0.88(t, 3 H, J=6.3 Hz) $^{13}$C-NMR (ppm, ref.-TMS, CDCl$_3$) 172.4, 142.8, 136.0, 134.2, 126.9, 123.3, 121.7, 38.7, 31.9, 29.6, 29.4, 29.32, 29.30, 29.1, 25.2, 22.7, 14.1

IR (cm$^{-1}$, KBr) 3332, 2917, 2850, 1683, 1609, 1578, 1502, 1330, 1258, 1170, 919, 848

MS (FAB, NBA)

m/z=355 (M$^+$+1)

[1-8-2] Synthesis of laur-5-dibutylamino-2-nitroanilide

A mixed solution of 2.13 g of laur-5-chloro-2-nitroanilide, 1.29 g of dibutylamine, 0.33 g of potassium carbonate, 0.24 g of copper powder and 3.6 mg of iodine was allowed to react at a reaction temperature of 155° C. for a period of 6 hr. After filtering the inorganic compounds out from the reacted solution, the filtered solution was purified by silica gel chromathography to obtain 1.47 g of yellow crystal of laur-5-dibutylamino-2-nitroanilide (yield 54.5%).

Analytical Data m.p.=90.3(° C.)

$^1$H-NMR (ppm, ref.-TMS, CDCl$_3$) 11.18(s, 1H), 8.19(d, 1 H, J=2.7 Hz), 8.12(d, 1 H, J=9.7 Hz), 6.31(dd, 1 H, J=9.7, 2.7 Hz), 3.39(t, 4 H, J=7.7 Hz), 2.47(t, 2 H, J=7.5 Hz), 1.78-1.71(m, 2 H), 1.68-1.58(m, 4 H), 1.46-1.26(m, 20 H), 0.98(t, 6 H, J=7.3 Hz), 0.88(t, 3 H, J=6.0 Hz) $^{13}$C-NMR (ppm, ref.-TMS, CDCl$_3$) 172.9, 153.9, 138.3, 128.8, 124.5, 106.2, 100.6, 51.2, 39.2, 31.9, 29.6, 29.44, 29.36, 29.31, 29.1, 25.5, 22.7, 20.2, 14.1, 13.9

IR (cm$^{-1}$, KBr) 2918, 2850, 1610, 1569, 1275, 1219, 1178, 1091, 850, 741

MS (FAB, NBA)

m/z=448 (M$^+$+1)

[1-8-3] Synthesis of laur-5-dibutylamino-2-aminoanilide 30 mg of 5% palladium carbon was added to 100 ml of ethanol solution containing 330 mg of laur-5-dibutylamino-2-nitroanilide and the hydrogenation reaction was allowed to proceed at 40° C. for a period of 7 hr. After the completion of the reaction, 5% palladium carbon is filtered and ethanol was distilled away. On recrystallization of the precipitated crystals by hexane-ethyl acetate, 215 mg of laur-5-dibutylamino-2-aminoanilide (yield 69.8%).

Analytical Data m.p.=69.9–71.6(° C.)

$^1$H-NMR (ppm, ref-TMS, CDCl$_3$) 7.57(br, 1 H), 6.94(br, 1 H), 6.71(br, 1 H), 6.41(br, 1 H), 3.15(br, 4 H), 2.35(t, 2 H, J=7.4 Hz), 1.72(m, 2 H), 1.50(m, 4 H), 1.48-1.26(m, 20 H), 0.95-0.86(m, 9 H) $^{13}$C-NMR (ppm, ref.-TMS, CDCl$_3$) 171.6, 143.9, 128.2, 127.8, 121.1, 111.3, 108.6, 51.6, 37.5, 31.9, 29.7, 29.6, 29.5, 29.4, 29.3, 25.9, 22.7, 20.4, 14.1, 14.0

IR (cm$^{-1}$, KBr) 3288, 2915, 2850, 1650, 1516, 1468, 1424, 1370, 798, 718

MS (FAB, NBA)

m/z=417 (M$^+$+1)

[1-8-4] Synthesis of the Indoaniline Described in The Exemplified Compound 3-53

While stirring a mixed solution comprising 310.7 mg of 4-hydroxyphenanthridine (13), 626.5 mg of laur-5-dibutylamino-2-aminoanilide and 10 ml of ethanol at 20° C., a solution comprising 255.0 mg of silver nitrate dissolved in 1.0 ml of water was added thereto drop-by-drop. 30 min later, 1.28 ml of 25% ammonia solution was added, further a solution comprising 510.0 mg of silver nitrate dissolved in 2.0 ml of water was added thereto drop-by-drop and reaction was allowed to proceed at 20° C. for a period of 1.5 hr. After the completion of the reaction, the reacted solution was introduced into water. After extraction by chloroform, the extract was concentrated. On purification by silica gel column chromatography, 55.2 mg of indoaniline described in the exemplified compound 3-53 was obtained (yield 6.04%).

Analytical Data m.p.=67.7–69.8(° C.)

$^1$H-NMR (ppm, ref.-TMS, CDCl$_3$) 9.66(d, 1 H, J=8.3 Hz), 9.37(s, 1 H), 8.72(s, 1 H), 8.19(d, 1 H, J=2.0 Hz), 8.07(d, 1 H, J=7.9 Hz), 7.81-7.76(m, 2 H), 7.72(d, 1 H, J=10.3 Hz), 7.00(d, 1 H, J=9.0 Hz), 6.86(dd, 1 H, J=10.3, 0.8 Hz), 6.46(dd, 1 H, J=9.0, 2.0 Hz), 3.43(t, 4 H, J=7.3 Hz), 2.35(t, 2 H, J=7.5 Hz), 1.71-1.64(m, 6 H) 1.47-1.40(m, 4 H), 1.28-1.19(m, 16 H), 1.01(t, 6 H, J=7.2 Hz), 0.87(t, 3 H, J=5.8 Hz) $^{13}$C-NMR (ppm, ref.-TMS, CDCl$_3$) 183.9, 171.6, 154.7, 150.7, 150.5, 142.3, 138.0, 133.0, 131.9, 131.3, 130.3, 130.1, 128.8, 127.4, 126.3, 123.5, 107.1, 102.3, 51.2, 38.5, 31.8, 29.7, 29.5, 29.4, 29.30, 29.25, 29.20, 29.19, 25.6, 22.6, 20.3, 14.1, 13.9

IR (cm$^{-1}$, KBr) 3356, 2922, 2852, 1608, 1588, 1462, 1361, 1227, 1089, 1000, 803, 747

MS (FAB, NBA)

m/z=610 (M$^+$+1)

The visible to near-infrared absorption spectrum (acetone solution) had a maximum wavelength of absorption 659.2 nm (molar extinction coefficient=26,700).

[1-8-5] Preparation of the Indoaniline Metal Complex Described in the Exemplified Compound 1-53

With 1 ml of aqueous solution containing 49.4 mg of copper perchlorate hexahydrate (23) added to 4 ml of ethanol solution containing 32.2 mg of indoaniline described in the exemplified compound 3-53, reaction was allowed to proceed at 20° C. for a period of 15 hr. After the completion of the reaction, the precipitated crystals were taken out by filtration and washed with a small amount of water and ethanol, followed by 4-hr reduced-pressure drying to obtain 34.9 mg of deep green crystals of the indoaniline metal complex described in the exemplified compound 1-53 (yield 89.3%).

Analytical Data m.p.=300(° C.) or higher

IR (cm$^{-1}$, KBr) 2923, 2852, 1575, 1503, 1451, 1332, 1143, 1086, 814, 617

The visible to near-infrared absorption spectrum (acetone solution) had a maximum wavelength of absorption 779 nm (molar extinction coefficient=78,600).

Prepared Example 1-9: Preparation of the Indoaniline Metal Complex Described in the Exemplified Compound 1-57

With 5 ml of aqueous solution containing 52.4 mg of nickel perchlorate hexahydrate added to 5 ml of ethanol solution containing 30.0 mg of indoaniline described in the exemplified compound 3-10, reaction was allowed to proceed at 20° C. for a period of 12 hr. After the completion of the reaction, the precipitated crystals were taken out by filtration and washed with a small amount of water and ethanol, followed by 4-hr reduced-pressure drying to obtain 19.0 mg of green crystals of the indoaniline metal complex described in the exemplified compound 1-57 (yield 50.8%).

Analytical Data m.p.=194–197(° C.)

IR (cm$^{-1}$, KBr) 3956, 2928, 2978, 1578, 1541, 1457, 1424, 1392, 1351, 1169, 1130, 1098, 1012, 825, 740, 443

The visible to near-infrared absorption spectrum (acetone solution) had a maximum wavelength of absorption 798.8 nm (molar extinction coefficient–100,800).

Prepared Example 1-10: Preparation of the Indoaniline Metal Complex Described in the Exemplified Compound 1-58

With 5 ml of aqueous solution containing 75.0 mg of iron perchlorate hydrated added to 5 ml of ethanol solution containing 30.0 mg of indoaniline described in the exemplified compound 3-10, reaction was allowed to proceed at 20° C. for a period of 12 hr. After the completion of the reaction, the precipitated crystals were taken out by filtration and washed with a small amount of water and ethanol, followed by 4-hr reduced-pressure drying to obtain 25.3 mg of deep green crystals of the indoaniline metal complex described in the exemplified compound 1-58 (yield 67.8%).

Analytical Data m.p.=300(° C.) or higher

IR (cm$^{-1}$, KBr) 2956, 2928, 2870, 1573, 1518, 1423, 1391, 1326, 1279, 1243, 1139, 1095, 1014, 821, 613, 487, 447

The visible to near-infrared absorption spectrum (acetone solution) had a maximum wavelength of absorption 811.2 nm (molar extinction coefficient=67,000).

Prepared Example 1-11: Preparation of the Indoaniline Metal Complex Described in the Exemplified Compound 1-131

[1-11-1] Synthesis of N-(2-chloro-4-fluorobenzylidene)-2'-methoxyaniline

A mixed solution comprising 627.0 mg of o-anisidine, 807.1 mg of 2-chloro-4-fluorobenzaldehyde and 50 ml of ethanol was allowed to react for a period of 24 hr at reflux temperature. After the completion of the reaction, 1.312 g of N-(2-chloro-4-fluorobenzylidene)-2'-methoxyaniline was obtained as yellow oil on removal of ethanol (yield 97.8%).

Analytical Data

IR (cm$^{-1}$, KBr) 3067, 2932, 2829, 1600, 1494, 1462, 1396, 1368, 1248, 1204, 1180, 1204, 1114, 1041, 1028, 909, 859, 821, 747, 586, 488, 426

MS (FAB, NBA)

m/z=264 (M$^+$+1)

[1-11-2] Preparation of 4-methoxy-6-fluorophenanthridine

After putting 1.05 g of metal potassium and 1 mg of iron nitrate enneahydrate into 70 ml of ammonia liquor, reaction was allowed to proceed at –60° C. for a period of one hour with 871.0 mg of N-(2-chloro-4-fluorobenzylidene)-2'-methoxyaniline added. After the completion of the reaction, ammonia was removed. After purifying the residue by column chromatography, 145.8 mg of 4-methoxy-6-fluorophenanthridine was obtained as light brown crystals on recrystallization from hexane-chloroform (yield 19.4%).

Analytical Data

Sublimated at 145° C.

$^1$H-NMR (ppm, ref.-TMS, CDCl$_3$) 9.23(s,1 H), 8.10(dd, 1 H, J=10.5, 2.2 Hz), 8.03(dd, 1 H, J=8.8, 5.8 Hz), 7.95(d, 1 H, J=8.1 Hz), 7.57(t, 1 H, J=8.1 Hz), 7.40(td, 1 H, J=8.5, 2.3 Hz), 7.15(d, 1 H, J=8.0 Hz), 4.11(s, 3 H) $^{13}$C-NMR (ppm, ref.-TMS, CDCl$_3$) 163.9(d, J=249.3 Hz), 155.9, 151.1, 135.3, 134.4(d, J=9.5 Hz), 131.3(d, 1 H, J=9.6 Hz), 127.3, 124.6(d, J=4.1 Hz), 123.4, 116.9(d, J=24.2 Hz), 114.0, 108.7, 107.4(d, J=22.3 Hz), 56.0

IR (cm$^{-1}$, KBr) 3425, 2934, 1623, 1504, 1469, 1254, 1156, 1118, 1028, 840, 751

MS (FAB, NBA)

m/z=228 (M$^+$+1)

[1-11-3] Preparation of 4-hydroxy-6-fluorophenanthridine

A mixed solution comprising 115 mg of 4-methoxy-6-fluorophenanthridine and 5 ml of 48% hydrobromic acid was allowed to react at 116° C. for a period of 14 hr. After the completion of the reaction, the reacted solution was introduced into an aqueous solution of sodium carbonate and the product was extracted by ethyl acetate. After ethyl acetate was distilled away, the residue was purified by column chromatography to obtain 104.5 mg of 4-hydroxy-6-fluorophenanthridine on recrystallization from hexane (yield 96.9%).

Analytical Data

Sublimated at 180° C.

$^1$H-NMR (ppm, ref.-TMS, d$_6$-DMSO) 9.89(s, 1 H), 9.30 (s, 1 H), 8.57(dd, 1 H, J=10.4, 0.9 Hz), 8.34(dd, 1 H, J=8.6, 6.1 Hz), 8.16(d, 1 H, J=8.2 Hz), 7.67(td, 1 H, J=8.6, 1.5 Hz), 7.55(t, 1 H, J=8.0 Hz), 7.18(d, 1 H, J=7.6 Hz) $^{13}$C-NMR (ppm, ref.-TMS, d$_6$-DMSO) 163.6(d, J=246.8 Hz), 154.0, 150.2, 134.3(d, J=9.5 Hz), 133.6, 132.2(d, J=9.9 Hz), 128.1, 124.1(d, J=3.8 Hz), 123.4, 117.0(d, J=24.2 Hz), 113.2, 112.9, 107.9(d, J=22.6 Hz)

IR (cm$^{-1}$, KBr) 3328, 1622, 1584, 1526, 1473, 1422, 1411, 1315, 1288, 1251, 1213, 1165, 1129, 1060, 895, 872, 833, 755, 705, 633, 547

MS (FAB, NBA)

m/z=214 (M$^+$+1)

[1-11-4] Preparation of the Indoaniline Described in the Exemplified Compound 3-131

While stirring a mixture comprising 59 mg of 4-hydroxy-6-fluorophenanthridine, 85 mg of 2-amino-5-diethylaminotoluene hydrochroride (21) and 4 ml of ethanol at 20° C., a solution comprising 258 mg of silver nitrate dissolved in 0.8 ml of water was added thereto drop-by-drop. Next, with 0.84 ml of 25% ammonia solution added, reaction was allowed to proceed at 20° C. for a period of 24 hr. After the completion of the reaction, the reacted solution was introduced into water. After extraction by chloroform, the extract was concentrated. After purification by column chromatography, 29 mg of indoaniline described in the exemplified compound 3-131 was obtained as deep blue crystal on recrystallization from hexane-ethyl acetate solvent (yield 27.1%).

Analytical Data m.p.=177.8–179.9(° C.)

$^1$H-NMR (ppm, ref.-TMS, CDCl$_3$) 9.96(dd, 1 H, J=13.0, 2.4 Hz), 9.40(s,1 H), 8.09(dd, 1 H, J=8.9, 6.0 Hz), 7.59(d, 1 H, J=10.4 Hz), 7.53(ddd, 1 H, J=9.3, 8.9, 2.4 Hz), 6.85(d, 1 H, J=10.4 Hz), 6.71(d, 1 H, J=2.5 Hz), 6.69(d, 1 H, J=8.8 Hz) 6.56(dd, 1 H, J=8.8, 2.5 Hz), 3.45(quartet, 4 H, J=7.1 Hz), 2.52(s, 3 H), 1.25(t, 6 H, J=7.1 Hz) $^{13}$C-NMR (ppm, ref-TMS, d$_6$-DMSO) 184.9, 164.9(d, J=242.0 Hz), 154.5, 153.1, 148.1, 143.0, 137.9, 136.6, 134.8, 131.9, 131.2, 131.1, 130.2, 127.5, 123.5, 119.2(d, J=25.8 Hz), 114.3(d, J=26.4 Hz), 113.8, 109.0, 44.7, 20.0, 12.8

IR (cm$^{-1}$, KBr) 3435, 2966, 2925, 1640, 1592, 1501, 1475, 1393, 1353, 1262, 1232, 1196, 1147, 1113, 1079, 998, 997, 845, 799

MS (FAB, NBA)

m/z=388 (M$^+$+1)

The visible to near-infrared absorption spectrum (acetone solution) had a maximum wavelength of absorption 647 nm (molar extinction coefficient=15,000).

[1-11-5] Preparation of the Indoaniline Metal Complex Described in the Exemplified Compound 1-131

With 1.3 ml of aqueous solution containing 60.2 mg of copper perchlorate hexahydrate (23) added to 2.5 ml of ethanol solution containing 25.0 mg of the indoaniline described in the exemplified compound 3-131, reaction was allowed to proceed at 20° C. for a period of 20 hr. After the completion of the reaction, the precipitated crystals were taken out by filtration and washed with a small amount of water and ethanol, followed by 4-hr reduced-pressure drying to obtain 30.0 mg of indoaniline metal complex described in the exemplified compound 1-131 as green crystals (yield 89.6%).

Analytical Data m.p.=300(° C.) or higher.

IR (cm$^{-1}$, KBr) 1622, 1590, 1576, 1533, 1449, 1417, 1381, 1327, 1276, 1246, 1147, 1120, 1071, 1014, 985, 856, 822, 801, 739, 669, 630, 508, 466

The visible to near-infrared absorption spectrum (acetone solution) had a maximum wavelength of absorption 790 nm (molar extinction coefficient=129,000).

Example 2: Preparation of Indoaniline Metal Complexes with the Acridine Skeleton Prepared Example 2-1: Preparation of the Indoaniline Metal Complex Described in the Exemplified Compound 2-1

Synthesis was carried out in accordance with the following reaction scheme.

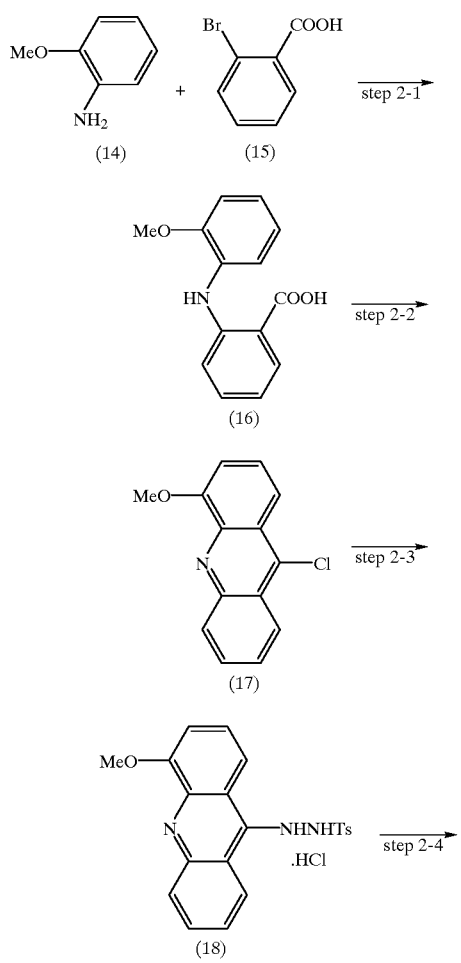

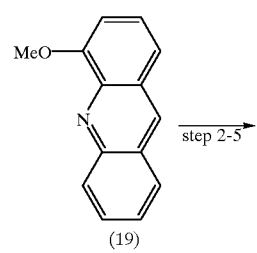

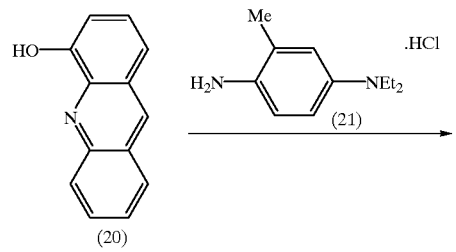

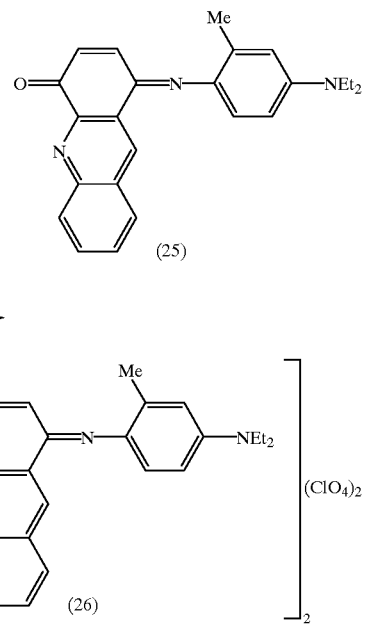

[2-1-1] Synthesis of 2-methoxydiphenylamine-2'-carboxylic Acid (16)

A mixed solution comprising 7.84 g of o-anisidine (14), 4.99 g of o-chlorobenzoic acid (15) and 500 mg of Copper (II) oxide was allowed to react at 140° C. for a period of 3 hr. After the completion of the reaction, inorganic substances were removed from the reacted solution. After purifying the residue by column chromatography, 6.30 g of 2-methoxydiphenylamine-2'-carboxylic acid (16) was obtained as crystals on recrystallization (yield 81.2%).

Analytical Data m.p.=174.0–175.0(° C.)

$^1$H-NMR (ppm, ref.-TMS, d$_6$-DMSO) 8.28(s, 1 H), 6.58 (dd, 1 H, J=8.0, 1.3 Hz), 6.06(d, 1 H, J=7.6 Hz), 6.04(td, 1 H, J=7.7, 1.6 Hz) 5.87(d, 1 H, J=8.2 Hz), 5.76-5.68(m, 2 H), 5.60(td, 1 H, J=7.2, 2.0 Hz), 5.43(t, 1 H, J=7.3 Hz), 3.38(s, 3 H) $^{13}$C-NMR (ppm, ref.-TMS, d$_6$-DMSO) 169.8, 150.9, 146.7, 134.0, 131.8, 129.3, 123.4, 120.5, 120.2, 117.1, 113.6, 112.8, 111.8, 55.6

IR (cm$^{-1}$, KBr) 3374, 2946, 1667, 1593, 1573, 1519, 1491, 1469, 1450, 1432, 1404, 1331, 1257, 1212, 1161, 1117, 1026, 909, 743, 671, 647, 569, 486

MS (FAB, NBA)
m/z=242 (M$^+$+1)

[2-1-2] Synthesis of 9-chloro-4-methoxyacridine (17)

A mixed solution comprising 3.06 g of 2-methoxydiphenylamine-2'-carboxylic acid (16) and 15 g of phosphoryl chloride was allowed to react at 100° C. for a period of 2 hr. After the completion of the reaction, the reacted solution was introduced into a mixed solution comprising 10 ml of 25% ammonia solution, 25 g of ice and 10 ml of chloroform. The reaction product was extracted by chloroform. After distilling chloroform away, the residue was purified by column chromatography and 2.58 g of 9-chloro-4-methoxyacridine (17) was obtained as crystals on recrystallization by hexane-chloroform (yield 84.1%).

Analytical Data m.p.=125.0–125.5(° C.)

$^1$H-NMR (ppm, ref.-TMS, d$_6$-DMSO) 8.37(d,1 H, J=8.6 H), 7.90(d, 1 H, J=8.8 Hz), 7.86(d,1 H, J=8.7 Hz), 7.65(br, 2 H), 7.61(t, 1 H, J=7.8 Hz), 7.30(t, 1 H, J=7.4 Hz), 7.19(t, 1 H, J=8.1 Hz), 6.99(d, 1 H, J=7.4 Hz), 3.92(s, 3 H) $^{13}$C-NMR (ppm, ref.-TMS, d$_6$-DMSO) 154.9, 149.6, 147.6, 141.6, 129.5, 129.2, 123.1, 121.9, 121.3, 114.6, 113.6, 113.2, 107.1, 55.3

IR (cm$^{-1}$, KBr) 3436, 1624, 1611, 1521, 1465, 1397, 1347, 1322, 1276, 1263, 1225, 1157, 1095, 1077, 990, 872, 804, 794, 755, 733, 597

MS (FAB, NBA)
m/z=225 (M$^+$+1)

[2-1-3] Synthesis of N$_1$-9-(4-methoxy)acridinyl-N$_2$-p-toluenesulfonylhydrazine hydrochloride (18)

A mixed solution comprising 817 mg of 9-chloro-4-methoxyacridine (17), 749 mg of p-toluenesulfonylhydrazide and 20 ml of n-amyl alcohol was allowed to react at 70° C. for a period of one hour. After the completion of the reaction, the reacted solution was cooled to room temperatures. Then, the precipitated crystals were collected by filtering and washed with ethyl acetate. Thereafter, 1.33 g of N$_1$-9-acridinyl-N$_2$-p-toluenesulfonylhydrazine hydrochloride (18) was obtained as crystals on drying (yield 92.4%). Without purification at this stage, the operation proceeded to the next reaction as it was.

[2-1-4] Synthesis of 4-methoxyacridine (19)

A mixed solution comprising 124 mg of N$_1$-9-(4-methoxy)acridinyl-N$_2$-p-toluenesulfonylhydrazine hydrochloride (18), 40 mg of sodium hydroxide, and 5 ml of ethylene glycol was allowed to react at 100° C. for a period of one hour. After the completion of the reaction, the reacted solution was introduced into water and the product was extracted by ethyl acetate. After ethyl acetate was distilled away, the residue was purified by column chromatography and 57.6 mg of 4-methoxyacridine (19) was obtained as crystals on recrystallization by hexane-ethyl acetate (yield 95.2%).

Analytical Data m.p=127.0–128.3(° C.)

$^1$H-NMR (ppm, ref.-TMS, CDCl$_3$) 8.70(s, 1 H), 8.40(d, 1 H, J=8.9 Hz), 7.95(d, 1 H, J=8.4 Hz), 7.75(t, 1 H, J=7.7 Hz), 7.55(d, 1 H, J=8.4 Hz), 7.52(t, 1 H, J=7.5 Hz), 7.42(t, 1 H, J=8.0 Hz), 7.02(d, 1 H, J=7.4 Hz), 4.15(s, 3 H) $^{13}$C-NMR (ppm, ref.-TMS, CDCl$_3$) 155.1, 148.1, 142.0, 135.8, 130.2, 129.9, 127.8, 127.5, 126.8 126.0, 125.6, 120.0, 106.5, 56.1

IR (cm$^{-1}$, KBr) 3444, 3003, 2953, 2827, 1624, 1560, 1530, 1465, 1402, 1366, 1320, 1268, 1224, 1178, 1143, 1126, 1095, 964, 937, 854, 770, 737, 718, 612, 572

MS (FAB, NBA)
m/z=210 (M$^+$+1)

[2-1-5] Preparation of 4-hydroxyacridine (20)

A mixed solution comprising 510 mg of 4-methoxyacridine (19) and 10 ml of 48% hydrobromic acid was allowed to react at 110° C. for a period of 14 hr. After the completion of the reaction, the reacted solution was introduced into an aqueous sodium carbonate solution water and the product was extracted by ethyl acetate. After ethyl acetate was distilled away, the residue was purified by column chromatography and 420 mg of 4-hydroxyacridine (20) was obtained as crystals on recrystallization by hexane-ethyl acetate (yield 88.3%).

Analytical Data m.p=115.0–115.5(° C.)

$^1$H-NMR (ppm, ref.-TMS, CDCl$_3$) 8.59(s, 1 H), 8.08(d, 1 H, J=8.8 Hz), 7.87(d, 1 H, J=8.6 Hz), 7.65(t, 1 H, J=7.7 Hz), 7.42(t, 1 H, J=7.5 Hz), 7.37-7.30(m, 2 H), 7.09(d, 1 H, J=7.7 Hz) $^{13}$C-NMR (ppm, ref.-TMS, CDCl$_3$) 151.7, 146.9, 140.2, 135.9, 130.2, 129.0, 128.2, 127.2, 126.8 126.6, 125.9, 118.1, 108.4

IR (cm$^{-1}$, KBr) 3357, 3054, 2925, 2854, 1636, 1562, 1521, 1467, 1440, 1399, 1369, 1321, 1228, 1212, 1129, 1070, 1035, 956, 919, 855, 771, 763, 733, 722, 647, 612, 592, 560, 535, 474

MS (FAB, NBA)
m/z=196 (M$^+$+1)

[2-1-6] Synthesis of the Indoaniline (25) Described in the Exemplified Compound 4-1

While stirring a mixture comprising 195 mg of 4-hydroxyacridine (20), 214 mg of 2-amino-5-diethylaminotoluene hydrochloride (21) and 6.8 ml of ethanol at 20° C., a solution comprising 0.17 mg of silver nitrate dissolved in 0.75 ml of water was added thereto drop-by-drop. Next, with 0.85 ml of 25% ammonia solution added to the mixture, reaction was allowed to proceed at 20° C. for a period of 24 hr. After the completion of the reaction, the reacted solution was introduced into water. After extraction by ethyl acetate, the extract was concentrated. After purification by column chromatography, 72.5 mg of indoaniline derivative (25) described in the exemplified compound 4-1 was obtained as deep blue crystals on recrystallization by hexane-ethyl acetate (yield 19.6%).

Analytical Data m.p.=148.7(° C.)

$^1$H-NMR (ppm, ref.-TMS, CDCl$_3$) 9.40(s, 1 H), 8.45(d, 1 H, J=8.7 Hz), 8.05(d, 1 H, J=8.2 Hz), 7.84(ddd, 1 H, J=8.4, 7.5, 1.1 Hz), 7.68(t, 1 H, J=7.2 Hz), 7.66(d, 1 H, J=10.3 Hz), 6.96(d, 1 H, J=10.3 Hz), 6.73-6.68(m, 2 H), 6.55(dd, 1 H, J=8.8, 2.7 Hz), 3.43(q, 4 H, J=7.1 Hz), 2.43(s, 3 H), 1.23(t, 6 H, J=7.1 Hz) $^{13}$C-NMR (ppm, ref.-TMS, CDCl$_3$) 184.7, 149.2, 148.8, 147.6, 146.2, 137.3, 135.9, 134.2, 133.0, 131.8, 131.3, 131.2, 129.5, 129.1, 128.8, 128.7, 122.8, 113.8, 109.1, 44.6, 19.2, 12.8

IR (cm$^{-1}$, KBr) 2967, 1666, 1587, 1498, 1394, 1373, 1262, 1080

MS (FAB, NBA)
m/z=370 (M$^+$+1)

Figure 8:
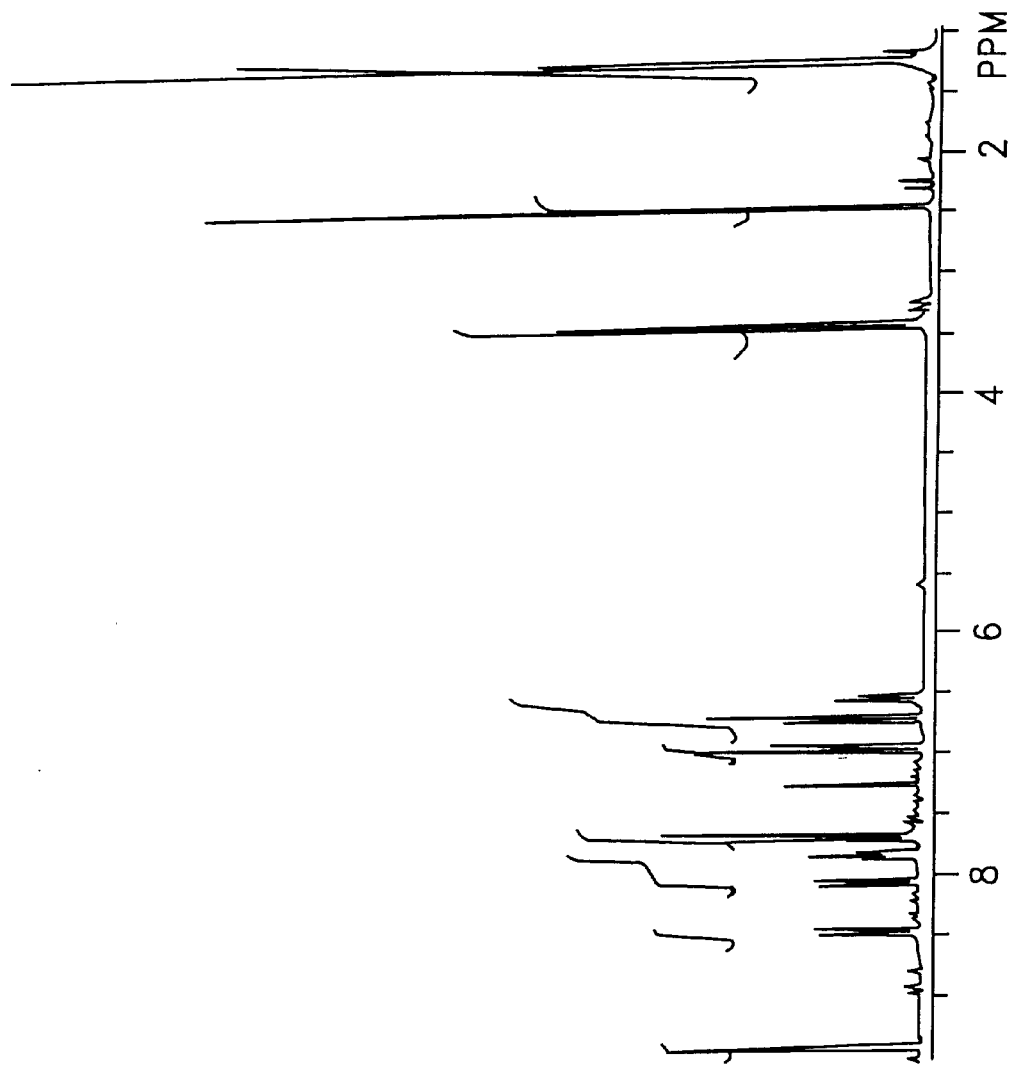
FIG. 8 is a spectral chart of $^1$H-NMR for the indoaniline metal complex (25) obtained in Preparing Example 2-1-6.
Figure 9:
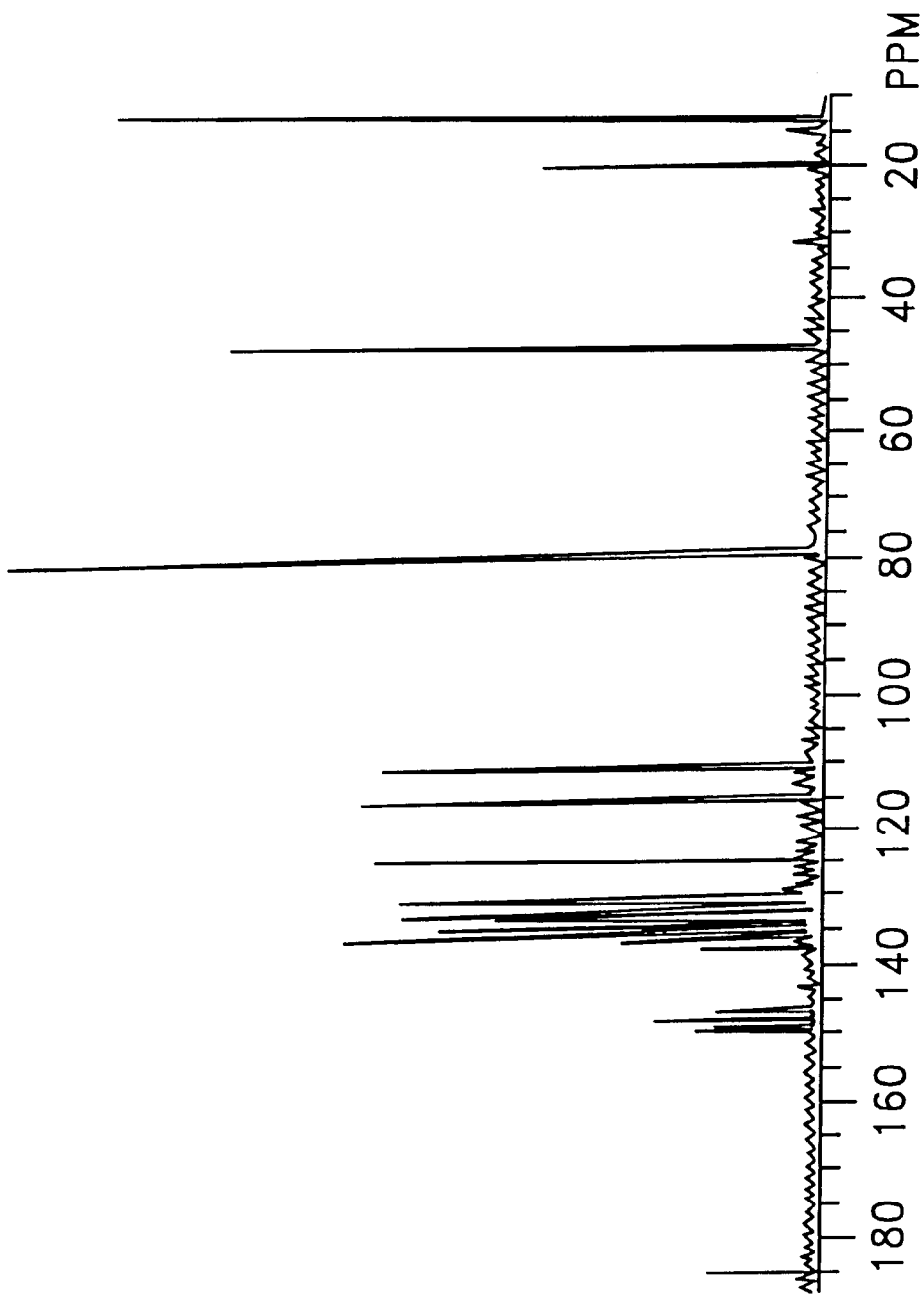
FIG. 9 is a spectral chart of $^{13}$C-NMR for the indoaniline metal complex (25) obtained in Preparing Example 2-1-6.
Figure 10:
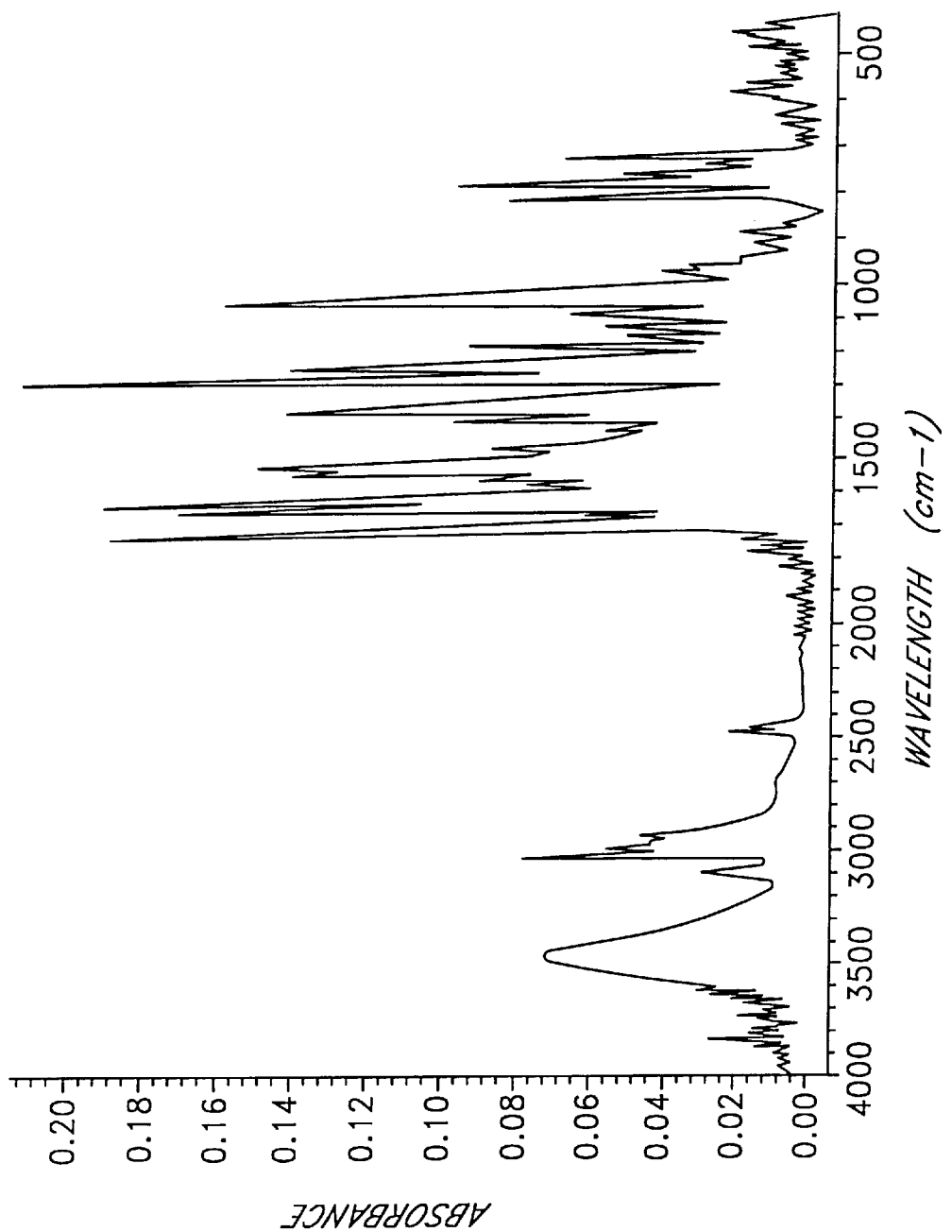
FIG. 10 is a chart of IR spectrum for the indoaniline metal complex (25) obtained in Preparing Example 2-1-6.
Figure 11:
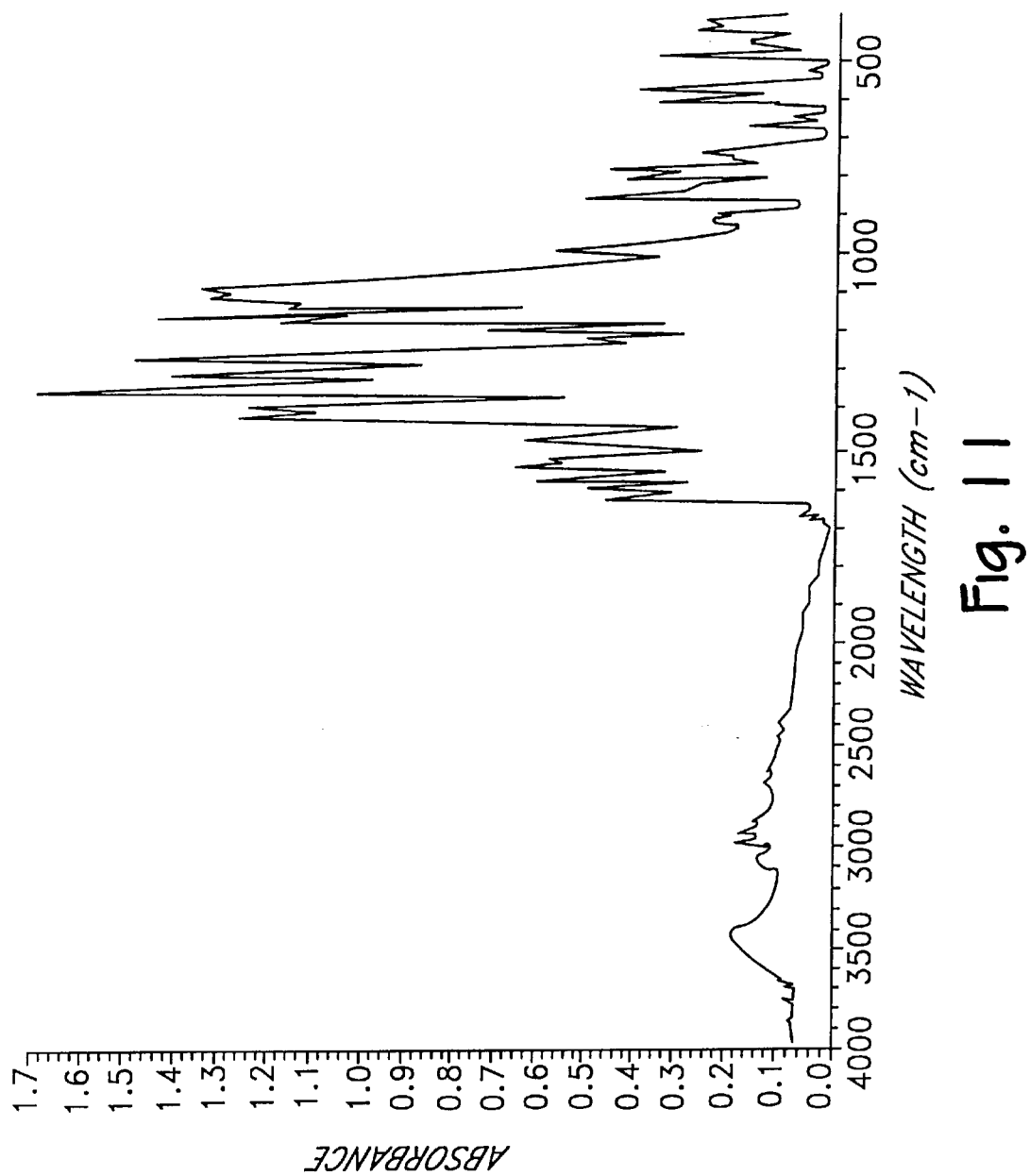
FIG. 11 is a chart of IR spectrum for the indoaniline metal complex (26) obtained in Preparing Example 2-1-7.
Figure 12:
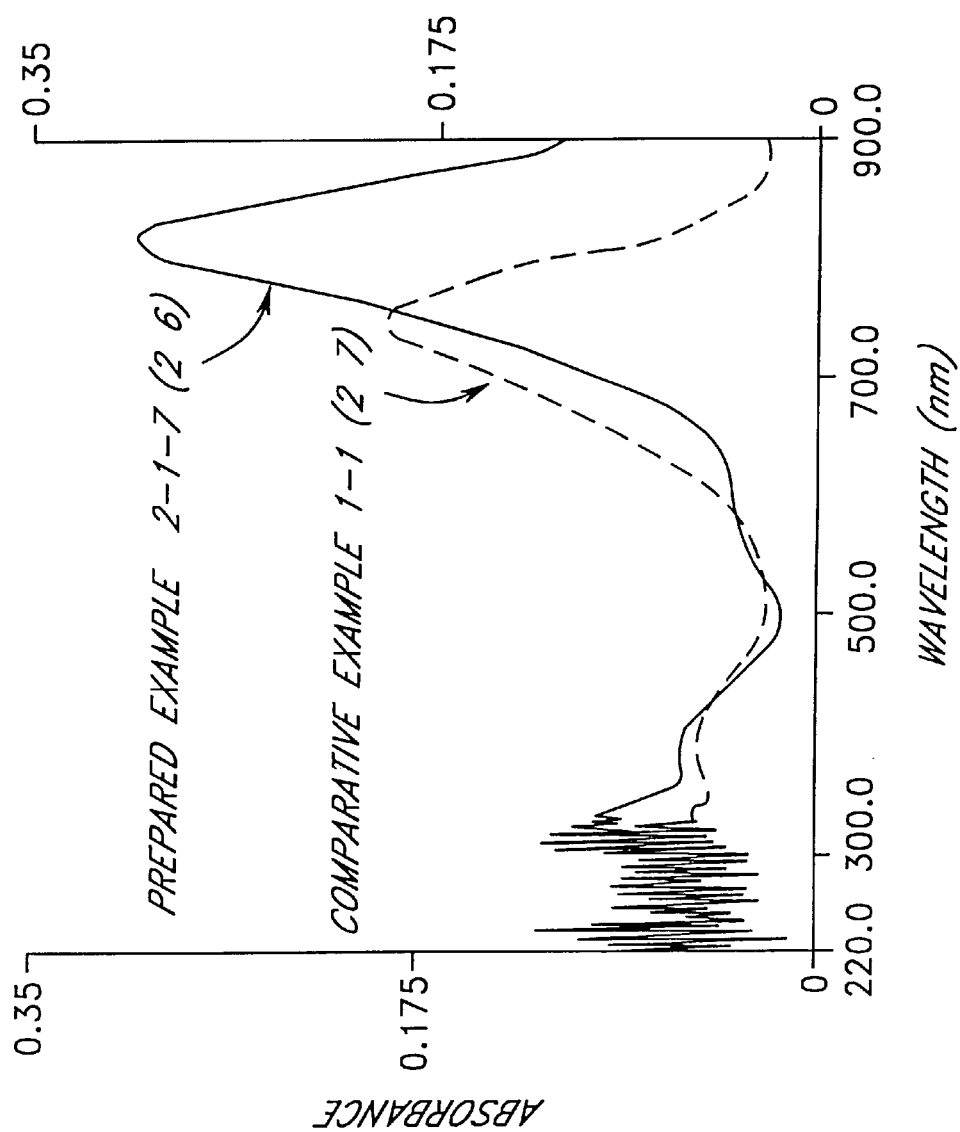
FIG. 12 is a chart of visible to near-infrared absorption spectrum for the indoaniline metal complex (26) obtained in Preparing Example 2-1-7 and the indoaniline metal complex (27) obtained in Comparative Example 1-1, where the ordinate represents an absorbance and the abscissa represents a wavelength (nm).

FIGS. 8, 9 and 10 show the spectral charts of $^1$H-NMR, $^{13}$C-NMR and IR, respectively. The visible to near-infrared absorption spectrum (acetone solution) had a maximum wavelength of absorption 606 nm (molar extinction coefficient=10,500).

[2-1-7] Preparation of the Indoaniline Metal Complex (26) Described in the Exemplified Compound 2-1

With 1.5 ml of aqueous solution containing 75.6 mg of copper perchlorate hexahydrate (23) added to 3 ml of ethanol solution containing 30.0 mg of indoaniline (25) described in the exemplified compound 4-1, reaction was allowed to proceed at 20° C. for a period of 2 hr. After the completion of the reaction, the precipitated crystals were filtered off and washed with a small amount of water and ethanol, followed by 4-hr reduced-pressure drying to obtain 31.5 mg of indoaniline metal complexes (26) described in the exemplified compounds 2-1 as black crystals (yield 77.4%).

Analytical Data m.p.=300(° C.) or higher

IR (cm$^{-1}$, KBr) 1569, 1530, 1462, 1393, 1376, 1325, 1286, 1247, 1143, 1115, 1091, 1072, 1033, 990, 859

The visible to near-infrared absorption spectrum (acetone solution) had a maximum wavelength of absorption 822 nm (molar extinction coefficient=97,000).

Prepared Example 2-2: Preparation of the Indoaniline Metal Complex Described in the Exemplified Compound 2-10

[2-2-1] Synthesis of the Indoaniline Derivative Described in the Exemplified Compound 4-10

While stirring a mixture comprising 2.87 g of 4-hydroxyacridine (20), 4.89 g of N,N-di(2-ethylhexyl)-p-phenylenediamine and 100 ml of ethanol at 20° C., a solution comprising 7.48 g of silver nitrate dissolved in 33.1 ml of water was added thereto drop-by-drop. Next, with 12.5 ml of 25% ammonia solution added to the mixture, reaction was allowed to proceed at 20° C. for a period of 24 hr. After the completion of the reaction, the reacted solution was introduced into water. After extraction by ethyl acetate, the extract was concentrated. After purification by column chromatography, 0.99 g of indoaniline described in the exemplified compound 4-10 was obtained as deep blue crystals on recrystallization by hexane-ethyl acetate (yield 12.9%).

Analytical Data m.p.=108.1–108.9(° C.)

$^1$H-NMR (ppm, ref.-TMS, CDCl$_3$) 9.370(s, 1 H), 8.44(d, 1 H, J=8.6 Hz), 8.03(d, 1 H, J=8.2 Hz), 7.83(t, 1 H, J=8.2 Hz), 7.74(d, 1 H, J=10.6 Hz), 7.66(t, 1 H, J=7.6 Hz), 7.08(d, 2 H, J=8.6 Hz), 6.97(d, 1 H, J=10.6 Hz), 6.76(d, 2 H, J=8.6 Hz), 3.44-3.23(m, 4 H), 1.95-1.80(m, 2 H), 1.54-1.18(m, 16 H), 1.06-0.77(m, 12 H) $^{13}$C-NMR (ppm, ref.-TMS, CDCl$_3$) 184.5, 149.7, 148.8, 147.9, 146.2, 138.0, 134.2, 133.0, 131.8, 131.2, 129.4, 129.0, 128.8, 128.7, 125.3, 112.8, 56.5, 37.0, 30.6, 28.7, 24.0, 23.9, 23.2, 14.1, 10.7

IR (cm$^{-1}$, KBr) 2980, 2926, 2858, 1663, 1607, 1582, 1508, 1461, 1364, 1335, 1284, 1227, 1178, 1156, 1141, 1081, 826, 804

MS (FAB, NBA)

m/z=524 (M$^+$+1)

The visible to near-infrared absorption spectrum (acetone solution) had a maximum wavelength of absorption 599 nm (molar extinction coefficient=21,000).

[2-2-2] Preparation of the Indoaniline Metal Complex Described in the Exemplified Compound 2-10

With 1.1 ml of aqueous solution containing 53.0 mg of copper perchlorate hexahydrate (23) added to 3 ml of ethanol solution containing 30.0 mg of indoaniline described in the exemplified compound 4-10, reaction was allowed to proceed at 20° C. for a period of 20 hr. After the completion of the reaction, the precipitated crystals were filtered off and washed with a small amount of water and ethanol, followed by 4-hr reduced-pressure drying to obtain 33.8 mg of indoaniline metal complexes described in the exemplified compounds 2-10 as black crystals (yield 90.1%).

Analytical Data m.p.=147.5–150.4(° C.)

IR (cm$^{-1}$, KBr) 2971, 2927, 2859, 1602, 1572, 1512, 1468, 1395, 1380, 1362, 1329, 1291, 1180, 1136, 1095, 1028, 831, 741

The visible to near-infrared absorption spectrum (acetone solution) had a maximum wavelength of absorption 840 nm (molar extinction coefficient=71,800).

Prepared Example 2-3: Preparation of the Indoaniline Metal Complex Described in the Exemplified Compound 2-57

With 1.1 ml of aqueous solution containing 52.4 mg of nickel perchlorate hexahydrate (23) added to 3 ml of ethanol solution containing 30.0 mg of indoaniline described in the exemplified compound 4-10, reaction was allowed to proceed at 20° C. for a period of 20 hr. After the completion of the reaction, the deposited crystals were filtersed off and washed with a small amount of water and ethanol, followed by 4-hr reduced-pressure drying to obtain 20.7 mg of indoaniline metal complexes described in the exemplified compounds 2-57 as black crystals (yield 55.3%).

Analytical Data m.p.=147.0–149.6(° C.)

IR (cm$^{-1}$, KBr) 2971, 2928, 2870, 1605, 1516, 1460, 1378, 1361, 1331, 1289, 1178, 1140, 1121, 1108, 827, 749, 628

The visible to near-infrared absorption spectrum (acetone solution) had a maximum wavelength of absorption 818 nm (molar extinction coefficient=29,500).

Prepared Example 2-4: Preparation of the Indoaniline Metal Complex Described in the Exemplified Compound 2-58

With 1.1 ml of aqueous solution containing 75.0 mg of iron perchlorate hydrate added to 3 ml of ethanol solution containing 30.0 mg of indoaniline described in the exemplified compound 4-10, reaction was allowed to proceed at 20° C. for a period of 20 hr. After the completion of the reaction, the precipitated crystals were filtered off and washed with a small amount of water and ethanol, followed by 4-hr reduced-pressure drying to obtain 17.5 mg of indoaniline metal complexes described in the exemplified compounds 2-58 as black crystals (yield 43.6%).

Analytical Data m.p.=300(° C.) or higher

IR (cm$^{-1}$, KBr) 2971, 2927, 2859, 1605, 1516, 1460, 1378, 1361, 1330, 1289, 1235, 1137, 1121, 1102, 823, 759, 622

The visible to near-infrared absorption spectrum (acetone solution) had a maximum wavelength of absorption 764 nm (molar extinction coefficient=16,600).

Example 3: Manufacturing Method of Transparent Recording Medium

Example 3-1

The following mixture was dissolved in an organic solvent (methyl ethyl ketone) to a solid content of 20%.

| | |
|---|---|
| Developer: n-propyl gallate tri-N-phenylcarbamate | 20 parts |
| Organic acid metal salt: iron o-benzoylbenzoate | 20 parts |
| Binder: polyvinyl butyral | 20 parts |
| Near-infrared absorbing material: indoaniline metal complex described in the exemplified compound 1-1 | 1 part |

The resultant coating liquid for recording was applied to a transparent polyester film by using a Mayer bar in an amount of 5 g/m$^2$, and dried in air at room temperature to obtain a transparent recording medium. When this transparent recording medium was scanned at 40 mm/sec using a semiconductor laser beam with a 30 mW output, black recorded images of a 50 μm line width were obtained. On projecting this transparent recording medium mounted on a slide, the black images could be magnified clearly with high resolution. Also, on projecting this transparent recording medium over an OHP, the black images could be magnified clearly with high resolution. A heat resistance test at 60° C.

revealed absolutely no color change. Even if exposed to sunlight for a week, the transparent recording medium exhibited no change in color.

Example 3-2

The following mixture was dissolved in an organic solvent (methyl ethyl ketone) to a solid content of 20%.

| Developer: n-propyl gallate tri-N-phenylcarbamate | 20 parts |
|---|---|
| Organic acid metal salt: iron o-benzoylbenzoate | 20 parts |
| Binder: polyvinyl butyral | 20 parts |
| Near-infrared absorbing material: indoaniline metal complex described in the exemplified compound 2-1 | 1 part |

The resultant coating liquid for recording was applied to a transparent polyester film by using a Mayer bar in an amount of 5 g/m$^2$, and dried in air at room temperature to obtain a transparent recording medium. When this transparent recording medium was scanned at 40 mm/sec by using a semiconductor laser beam with a 30 mW output, black recorded images of a 55 μm line width were obtained. On projecting this transparent recording medium mounted on a slide, the black images could be magnified clearly with high resolution. Also, on projecting this transparent recording medium over an OHP, the black images could be magnified clearly with high resolution. A heat resistance test at 60° C. revealed absolutely no color change. Even if exposed to sunlight for a week, the transparent recording medium exhibited no change in color.

Example 3-3

Except for substitution of 20 parts of an UV-curable resin GRANDIC UV5020 (available from Dainippon Ink & Chemicals Inc.) for the binder in the coating liquid for recording of Example 3-1, a coating liquid for recording was obtained in exactly the same manner as with Example 3-1. After applying the resultant recording coating liquid in an amount of 5 g/m$^2$ to a transparent polyester film by using a Mayer bar, a transparent recording medium was obtained, with the film moved at a speed of 5 m/min, by using the UV-curable resin with ultraviolet ray irradiated from a UV emitter (one lamp, output 3 kW, available from the Eyegraphic Co.) at a distance of 12 cm from the surface of the coated layer. When this transparent recording medium was scanned at 40 mm/sec by using a semiconductor laser beam with a 30 mW output, black recorded images of a 50 μm line width were obtained.

Example 3-4

Except for substitution of 20 parts of an UV-curable resin GRANDIC UV5020 (available from Dainippon Ink & Chemicals Inc.) for the binder in the coating liquid for recording of Example 3-2, a coating liquid for recording was obtained in exactly the same manner as with Example 3-2. After applying the resultant recording coating liquid in an amount of 5 g/m$^2$ to a transparent polyester film by using a Mayer bar, a transparent recording medium was obtained, with the film moved at a speed of 5 m/min, by using the UV-curable resin with ultraviolet ray irradiated from a UV emitter (one lamp, output 3 kW, available from the Eyegraphic Co.) at a distance of 12 cm from the surface of the coated layer. When this transparent recording medium was scanned at 40 mm/sec by using a semiconductor laser beam with a 30 mW output, black recorded images of a 55 μm line width were obtained.

Example 3-5

The following mixture was dissolved in an organic solvent (toluene) to a solid content of 20%.

| Developer: n-propyl gallate tri-N-phenylcarbamate | 5 parts |
|---|---|
| Organic acid metal salt: iron o-benzoylbenzoate | 20 parts |
| Binder: polyvinyl butyral | 20 parts |
| Near-infrared absorbing material: indoaniline metal complex described in the exemplified compound 1-2 | 1 part |

The resultant coating liquid for recording was applied to a transparent polyester film by using a Mayer bar in an amount of 5 g/m$^2$, and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-6

The following mixture was dissolved in an organic solvent (toluene) to a solid content of 20%.

| Developer: n-propyl gallate tri-N-phenylcarbamate | 5 parts |
|---|---|
| Organic acid metal salt: iron o-benzoylbenzoate | 20 parts |
| Binder: polyvinyl butyral | 20 parts |
| Near-infrared absorbing material: indoaniline metal complex described in the exemplified compound 1-7 | 1 part |

The resultant coating liquid for recording was applied to a transparent polyester film by using a Mayer bar in an amount of 5 g/m$^2$, and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-7

The following mixture was dissolved in an organic solvent (methyl isobutyl ketone) to a solid content of 25%.

| Developer: n-propyl gallate tri-N-phenylcarbamate | 5 parts |
|---|---|
| Organic acid metal salt: iron o-benzoylbenzoate | 20 parts |
| Binder: polyvinyl butyral | 20 parts |
| Near-infrared absorbing material [A]: indoaniline metal complex described in the exemplified compound 1-10 | 1 part |
| Near-infrared absorbing material [B]: NK-2014 Nippon Kankoh-Shikiso Kenkyusho Co., Ltd.) | 0.1 part |

The resultant coating liquid for recording was applied to a transparent polyester film by using a Mayer bar in an amount of 5 g/m$^2$, and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-8

The following mixture was dissolved in an organic solvent (methyl isobutyl ketone) to a solid content of 25%.

| Developer: n-propyl gallate tri-N-phenylcarbamate | 5 parts |
|---|---|
| Organic acid metal salt: iron o-benzoylbenzoate | 20 parts |
| Binder: polyvinyl butyral | 20 parts |
| Near-infrared absorbing material [A]: indoaniline metal complex described in the exemplified compound 1-11 | 1 part |
| Near-infrared absorbing material [B]: NK-1144 (Nippon Kankoh-Shikiso Kenkyusho Co., Ltd.) | 0.1 part |

The resultant coating liquid for recording was applied to a transparent polyester film by using a Mayor bar in an amount of 5 g/m$^2$, and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-9

The following mixture was dissolved in an organic solvent (chloroform) to a solid content of 10%.

| | |
|---|---|
| Developer: n-propyl gallate tri-N-cyclohexylcarbamate | 8 parts |
| Organic acid metal salt: iron o-benzoylbenzoate | 12 parts |
| Binder: polyvinyl butyral | 20 parts |
| Near infrared absorbing material [A]: indoaniline metal complex described in the exemplified compound 1-15 | 1 part |
| Near-infrared absorbing material [B]: NIR-14 (Yamamoto Chemical Ind.) | 0.1 part |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec by using a semiconductor laser beam with a 30 mW output, black recorded images of a 50 μm line width were obtained.

Example 3-10

The following mixture was dissolved in an organic solvent (chloroform) to a solid content of 10%.

| | |
|---|---|
| Developer: n-propyl gallate tri-N-cyclohexylcarbamate | 8 parts |
| Organic acid metal salt: iron o-benzoylbenzoate | 12 parts |
| Binder: polyvinyl butyral | 20 parts |
| Near-infrared absorbing material [A]: indoaniline metal complex described in the exemplified compound 1-25 | 1 part |
| Near-infrared absorbing material [B]: PA-1006 (Mitsui ToAtsu Chemicals K.K.) | 0.1 part |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec by using a semiconductor laser beam with a 30 mW output, black recorded images of a 55 μm line width were obtained.

Example 3-11

The following mixture was dissolved in an organic solvent (chloroform/acetone) to a solid content of 20%.

| | |
|---|---|
| Developer: n-propyl gallate trimethylcarbonate | 20 parts |
| Leuco dye: crystal violet lactone | 20 parts |
| Binder: polystyrene | 20 parts |
| Near-infrared absorbing material: indoaniline metal complex described in the exemplified compound 1-53 | 3 parts |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec using a semiconductor laser beam with a 30 mW output, blue recorded images of a 40 μm line width were obtained. On projecting this transparent recording medium mounted on a slide, the blue images could be magnified clearly with high resolution. A heat resistance test at 60° C. revealed absolutely no color change.

Example 3-12

The following mixture was dissolved in an organic solvent (chloroform acetone) to a solid content of 20%.

| | |
|---|---|
| Developer: n-propyl gallate trimethylcarbonate | 20 parts |
| Leuco dye: crystal violet lactone | 20 parts |
| Binder: polystyrene | 20 parts |
| Near-infrared absorbing material: indoaniline metal complex described in the exemplified compound 1-57 | 3 parts |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec by using a semiconductor laser beam with a 30 mW output, blue recorded images of a 35 μm line width were obtained. On projecting this transparent recording medium mounted on a slide, the black images could be magnified clearly with high resolution. A heat resistance test at 60° C. revealed absolutely no color change.

Example 3-13

The following mixture was dissolved in an organic solvent (toluene) to a solid content of 20%.

| | |
|---|---|
| Developer: n-propyl gallate tri-N-phenylcarbamate | 5 parts |
| Organic acid metallic salt: iron o-benzoylbenzoate | 20 parts |
| Binder: polystyrene | 20 parts |
| Near-infrared absorbing material: indoaniline metal complex described in the exemplified compound 1-58 | 1 part |
| Singlet oxygen quencher: salicylaldoxime | 0.1 part |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-14

The following mixture was dissolved in an organic solvent (toluene) to a solid content of 20%.

| | |
|---|---|
| Developer: n-propyl gallate tri-N-phenylcarbamate | 5 parts |
| Organic acid metal salt: iron o-benzoylbenzoate | 20 parts |
| Binder: polystyrene | 20 parts |
| Near-infrared absorbing material: indoaniline metal complex described in the exemplified compound 1-131 | 1 part |
| Singlet oxygen quencher: salicylaldoxime | 0.1 part |

The resultant coating liquid for recording was applied to a transparent polyester film by using a Mayer bar in an amount of 5 g/m², and dried in air at room temperature to obtain a transparent recording medium. When this transparent recording medium was scanned at 40 mm/sec by using a semiconductor laser beam with a 30 mW output, black recorded images of a 45 μm line width were obtained.

Example 3-15

The following mixture was dissolved in an organic solvent (toluene/methyl ethyl ketone) to a solid content of 20%.

| | |
|---|---|
| Developer: n-propyl gallate tri-N-phenylcarbamate | 5 parts |
| Organic acid metal salt: iron o-benzoylbenzoate | 20 parts |
| Binder: polystyrene | 20 parts |
| Near-infrared absobing material: indoaniline metal complex described in the exemplifled compound 2-10 | 1 part |

The resultant coating liquid for recording was applied to a transparent polyester film using a Mayer bar in an amount of 5 g/m², and dried in air at room temperature to obtain a transparent recording medium. When this transparent recording medium was scanned at 40 mm/sec using a semiconductor laser beam with a 30 mW output, black recorded lines of a 55 μm line width were obtained.

Example 4: Example of Printing by Use of a Masking Material According to the Present Invention Example 4-1

On the transparent recording medium obtained in Example 3-1, black images and characters were recorded using near-infrared semiconductor laser rays with an output power 30 mW. With the transparent recording medium on which images and characters were recorded and a PS-plate made by Fuji Photo Film Co., Ltd. (VPS (positive)) mutually overlapped, rays of a metal halide lamp (wavelength: 417 nm) were irradiated to them from the side of the transparent recording medium and images were exposed. The printing plate for offset print obtained in this manner, was loaded on a printer (Hamada 611XL) for offset plate and printed onto fine-quality paper (woodfree paper) and coated paper. Images and characters of a printed substance had exactly the same image quality as with those recorded on the transparent recording medium and neither background stain in the non-image portion nor deteriorated images in the image portion thereof were observed at all even for more than 5000 printed sheets.

Example 4-2

On the transparent recording medium obtained in Example 3-2, black images and characters were recorded using near-infrared semiconductor laser rays with an output power 30 mW. With the transparent recording medium on which images and characters were recorded and a PS-plate made by Fuji Photo Film Co., Ltd. (VPS (positive)) mutually overlapped, rays of a metal halide lamp (wavelength: 417 nm) were irradiated to them from the side of the transparent recording medium and images were exposed. The printing plate for offset print obtained in this manner, was loaded on a printer (Hamada 611XL) for offset plate and printed onto fine-quality paper (woodfree paper) and coated paper. Images and characters of a printed substance had exactly the same image quality as with those recorded on the transparent recording medium and neither background stain in the non-image portion nor deteriorated images in the image portion thereof were observed at all even for more than 5000 printed sheets.

Example 4-3

On the transparent recording medium obtained in Example 3-15, black images and characters were recorded using near-infrared semiconductor laser rays with an output power 30 mW. With the transparent recording medium on which images and characters were recorded and a PS-plate made by Fuji Photo Film Co., Ltd. (VPS (positive)) mutually overlapped, rays of a metal halide lamp (wavelength: 417 nm) were irradiated to them from the side of the transparent recording medium and images were exposed. The printing plate for offset print obtained in this manner, was loaded on a printer (Hamada 611XL) for offset plate and printed onto fine-quality paper (woodfree paper) and coated paper. Images and characters of a printed substance had exactly the same image quality as with those recorded on the transparent recording medium and neither background stain in the non-image portion nor deteriorated images in the image portion thereof were observed at all even for more than 5000 printed sheets.

Example 5: Manufacturing Method of an Optical Recording Medium

Example 5-1

A homogeneous coating liquid composed of the following constituents was added thereto drop-by-drop onto a transparent polyester film, coated over the whole film at a rotation rate of 500 rpm by the spinner method and dried at 40° C. for a period of 20 min.

| Near-infrared absorbing material: indoaniline metal complex described in the exemplified compound 1-1 | 1 part |
| --- | --- |
| Organic solvent: acetone | 50 part |

When this optical recording medium was irradiated with a near-infrared semiconductor laser beam with a 5 mW output, a spot of 4.1 μm diameter was obtained.

Example 5-2

A homogeneous coating liquid composed of the following constituents was added thereto drop-by-drop onto a transparent polyester film, coated over the whole film at a rotation rate of 500 rpm by the spinner method and dried at 40° C. for a period of 20 min.

| Near-infrared absorbing material: indoaniline metal complex described in the exemplified compound 3-1 | 1 part |
| --- | --- |
| Organic solvent: acetone | 50 part |

When this optical recording medium was irradiated with a near-infrared semiconductor laser beam with a 5 mW output, a spot of 4.3 μm diameter was obtained.

Example 5-3

| Near-infrared absorbing material: indoaniline metal complex described in the exemplified compound 2-10 | 1 part |
| --- | --- |
| Organic solvent: acetone | 50 parts |

A homogeneous coating liquid composed of the following constituents was added thereto drop-by-drop onto a transparent polyester film, coated over the whole film at a rotation rate of 500 rpm by the spinner method and dried at 40° C. for a period of 20 min. When this optical recording medium was irradiated with a near-infrared semiconductor laser beam with a 5 mW output power, a spot of 4.5 μm diameter was obtained.

COMPARATIVE EXAMPLES

Comparative Example 1-1

Except that one part of indoaniline metal complex represented by the following structural formula (27) was employed in place of the near-infrared absorbing material of Example 3-1, a transparent recording medium was manufactured in exactly the same manner as with Example 3-1.

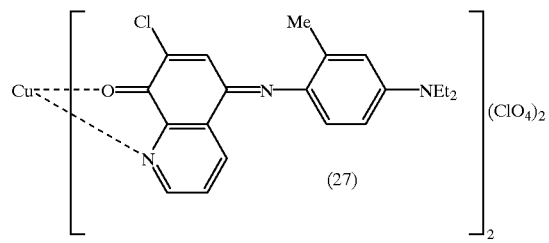

When this transparent recording medium was scanned at 40 mm/sec using a semiconductor laser beam with a 30 mW output, black recorded images of a 40 μm line width were obtained.

However, the coloration of the obtained transparent recording medium was so deep that images lacking in contrast were obtained.

Comparative Example 1-2

Except that one part of NK-2014 (Nippon Kankoh-Shikiso Kenkyusho Co., Ltd.) was employed in place of the near-infrared absorbing material of Example 3-1, a transparent recording medium was manufactured in exactly the same manner as with Example 3-1.

When this transparent recording medium was scanned at 40 mm/sec by using a semiconductor laser beam with a 30 mW output, black recorded images of a 40 $\mu$m line width were obtained. However, when exposed to sunlight for three days, the transparent recording medium changed color from light yellow green to brown.

Comparative Example 1-3

Except that one part of benzoin nickel complex was employed in place of the near-infrared absorbing material of Example 3-1, a transparent recording medium was manufactured in exactly the same manner as with Example 3-1. However, a transparent recording medium having an uneven coated surface and lacking in transparency was obtained.

Comparative Example 2-1

Except that the transparent recording medium of Comparative Example 1-1 was employed in place of the transparent recording medium of Example 3-1, a plate for offset print was obtained. Images and characters in a print substance obtained by printing with this plate were unclear.

Comparative Example 3-1

Except that one part of indoaniline metal complex represented by the above structural formula (27) was employed in place of the near-infrared absorbing material of Example 5-1, an optical recording medium was manufactured in exactly the same manner as with Example 5-1. When this optical recording medium was irradiated with a near-infrared semiconductor laser beam with a 5 mW output, however, only a spot of 2.1 $\mu$m diameter was obtained.

A new indoaniline metal complex according to the present invention has a large absorption in the near-infrared range, exhibiting a high molar extinction coefficient and a greatly improved efficiency of converting near-infrared laser rays into heat as compared with a conventional indoaniline metal complex. Because of decreasing in visible absorption and exhibiting a high recording density in record by near-infrared laser rays, a transparent recording medium, made up using this new indoaniline metal complex as a near-infrared absorbing material, is quite excellent in the contrast of images. In addition, because of exhibiting no change whatever in color, molar extinction coefficient and the efficiency of converting near-infrared laser rays into heat, a new indoaniline metal complex according to the present invention is a coloring substance quite excellent in light resistance and consequently a transparent recording medium made up using this metal complex is also excellent in light resistance. Furthermore, according to the present invention, new indoaniline metal complexes and new indoaniline derivatives according to the present invention are applicable to green-type coloring substances, heat-sensitive coloring substances, ink jet printer coloring substances, optical disks, heat-ray intercepting agents, safe light filters for photosensitive materials, cut filters of semiconductor elements, color filters, liquid crystals, anti-halation materials for photosensitive materials, optical cards, photopolymerization initiators, physiologically active matters, medicaments and the like.

We claim:

1. A phenanthridine derivative formula 3:

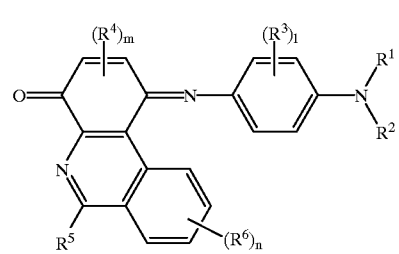

wherein $R^1$ and $R^2$ each independently are a hydrogen atom, alkyl group, or aryl group, or jointly form a five- or six-member nitrogen heterocycle or a polycyclic ring containing said five- or six-member nitrogen heterocycle; $R^3$ is a hydrogen atom or electron donating groups; and $R^4$, $R^5$, and $R^6$ each independently are a hydrogen atom or electron withdrawing groups; whereas l and n are each independently an integer of 1–4, and m is an integer of 1 or 2.

2. A phenanthridine derivative according to claim 1, wherein said phenanthridine derivative is in the form of a metal complex of formula 1:

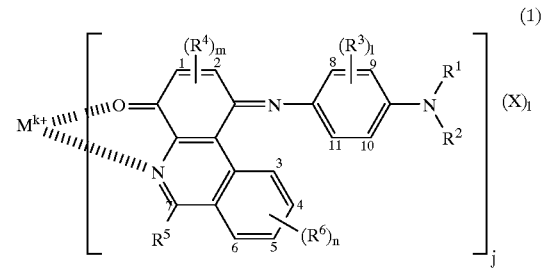

wherein M is a metal atom; $R^1$, $R^2$, $R^3$, $R^4$, $R^7$, $R^8$, l, m, and o are as defined in formula 3, i, j and k are each an integer of 1–3, and X is a negative ion.

3. A phenanthridine derivative according to claim 2, wherein said phenanthridine derivative metal complex is obtained by chelating a phenanthridine derivative of formula 3 with an inorganic metal salt of formula 9:

$$M^{r+}(X)_s \cdot t(H_2O) \tag{9}$$

wherein M is as defined in formula 3, r and s are each independently an integer of 1–3, and t is an integer of 0–20.

4. A phenanthridine derivative according to claim 1, wherein $R^1$ and $R^2$ are each selected from the group consisting of a hydrogen atom, alkyl group, and aryl group, or $R^1$ and $R^2$ jointly form a five- or six-member nitrogen heterocycle; $R^3$ is selected from the group consisting of a hydrogen atom, alkyl group, aralkyl group, alkoxy group, aryloxy group, alkylthio group, arylthio group, and alkyl-substituted amino group; $R^4$, $R^7$, and $R^8$ are each selected from the group consisting of a hydrogen atom, halogen atom, trifluoromethyl, cyano, aryl group, carbonyl, hydroxycarbonyl, alkoxycarbonyl, aryloxycarbonyl, aminothiocarbonyl, carbamoyl, sulfonyl and sulfamoyl; l and o are each 1, 2, or 3; and m is 1.

5. A phenanthridine derivative according to claim 4, wherein $R^1$ and $R^2$ are each selected from the group consisting of a hydrogen atom, methyl, ethyl, propyl, butyl, pentyl, hexyl, 2-ethylhexyl, cetyl, 2-ethoxyethyl, methoxyethoxyl, benzyl, 2-carboxyethyl, 2-cyanoethyl, 2-chloroethyl, 2-benzyloxyethyl, methylcarbonyloxyethyl, 2-phenoxyethyl, 2-acetoxyethyl, ethoxycarbonylmethyl, 3-mesylpropyl, 2-propenyl, 2-oxolanylmethyl, propenyl, p-tolyl, p-chlorophenyl, p-methoxyphenyl, p-n-butoxyphenyl, 2-methyl-2-propenyl, 2-chloro-2-propenyl, and cyclohexyl; or $R^1$ and $R^2$ jointly form a piperidinyl or morpholinyl.

6. A phenanthridine derivative according to claim 4, wherein $R^3$ is selected from the group consisting of a hydrogen atom, methyl, ethyl, cyclohexyl, 2-methoxyethyl, 2-allyloxyethyl, benzyl, methoxy, ethoxy, phenoxy, diethylamino, diisopropylamino, tosylamino, mesylamino, lauloylamino, palmitoylamino, stearoylamino, 1-naphthoylamino, methylthio, n-butylthio, phenylthio, p-chlorophenylthio, benzylthio, N-n-propylureido, N,N-diethylureido, thioureido, and N-acetyl-N-phenylthioreido.

7. A phenanthridine derivative according to claim 4, wherein $R^4$ is selected from the group consisting of a hydrogen atom, acetyl, isovaleryl, stearoyl, benzoyl, 1-naphthoyl, carboxy, phenylcarbamoyl, methylcarbamoyl, ethoxymethylcarbamoyl, 2-oxolanylmethylcarbamouyl, allylcarbamoyl, 3-(2-methoxycarbonyl)thienylcarbamoyl, 2-thiazolylcarbamoyl, 2-benzoimidazolylcarbamoyl, 2-benzoxazolylcarbamolyl, 2-benzothioazolylcarbamoyl, 2-pyridylcarbamoyl, 4-pyrimidylcarbamoyl, 2-qunolylcarbamoyl, 3H-indo-2-lylcarbamoyl, sulfo, phenylsufamoyl, methylsulfamoyl, ethoxymethylsufamoyl, 2-oxolanylmethylsulfamoyl, allylsufamoyl, 2-thienylsufamoyl, 2-thiazolylsulfamoyl, 2-benzoimidazolylsufamoyl, 2-benzoxazolylsulfamoyl, 2-benzothiazolylsulfamoyl, 2-pyridylsulfamoyl, 4-pyrimidylsulfamoyl, 2-quinolysulfamoyl, 3H-indo-2-lylsulfamoyl, methoxycarbonyl, ethylcarboxyl, n-butoxycarbonyl, lauryloxycarbaonyl, stearyloxycarbonyl, phenoxycarbonyl, p-tolyloxycarbonyl, p-chlorophenoxycarbonyl, p-methoxyphenocarbonyl, nitro, cyano, chloro, bromo, and fluoro.

8. A phenanthridine derivative according to claim 4, wherein $R^7$ is selected from the group consisting of a hydrogen atom, phenyl, fluoro, chloro, bromo, iodo, trifluoromethyl, cyano, o-tolyl, o-hydroxyphenyl, chlorophenyl, bromophenyl, iodophenyl, 3-pyridinyl, benzensulfonyl, p-tolenesulfonyl, formyl, acetyl, hydroxyiminomethylcarbonyl, bromoacetyl, hydroxycarbonyl, methoxycarbonyl, n-hexylcarbonyl, aminothiocarbonyl, and hydroxycarbonylmethyl.

9. A phenanthridine derivative according to claim 4, wherein $R^8$ is selected from the group consisting of a hydrogen atom, fluoro, chloro, phenyl, tolyl, chlorophenyl, methoxyphenyl, butoxyphenyl, methoxycarbonyl, ethoxycarbonyl, cyano, trifluoromethyl, nitro, carboxyl, phenoxycarbonyl, tolyloxycarbonyl, bromophenoxycarbonyl, acetyl, propionyl, isovaleryl, stearoyl, benzoyl, phenylcarbamoyl, methylcarbamoyl, allylcarbamoyl, thienylcarbamoyl, benzothiazolylcarbamoyl, 2-pyridylcarbamoyl, 3H-indo-2-lylcarbamoyl, phenysulfamoyl, methylsulfamoyl, 2-oxolanylmethylsulfamoyl, 2-thiazolylsulfamoyl, benzoimidazolylsufamoyl, and pyrimidylsulfamoyl.

10. A phenanthridine derivative according to claim 4, wherein $R^1$ and $R^2$ are each ethyl or 2-ethylhexyl; $R^3$ is a hydrogen atom, methyl or methoxy; $R^4$, $R^7$, and $R^8$ are each a hydrogen atom or halogen atom; l, m, and o are each 1.

11. A phenanthridine derivative according to claim 2 wherein M is selected from the group consisting of Fe, Co, Ni, Cu, Zn, Pd, and Pt; X is selected from the group consisting of $F^-$, $Cl^-$, $Br^-$, $I^-$, $ClO_4^-$, $SCN^-$, $BF_4^-$, $PF_6^-$, $SbF_6^-$, $TiF_6^{2-}$, $ZrF_6^{2-}$, $SiF_6^{2-}$, $OH^-$, $TsO^-$, $HCOO^-$, $CH_3COO^-$, $NO_3^-$, $H_2PO_4^-$, $Ph_4B^-$ and $CN^-$; and i, j, and k are each 2 or 3.

12. A phenanthridine derivative according to claim 11, wherein M is selected from the group consisting of Fe, Co, Ni, and Cu; X is selected from the group consisting of $Cl^-$, $Br^-$, $I^-$, $ClO_4^-$, $BF_4^-$, $PF_6^-$, and $SbF_6^-$.

13. A phenanthridine derivative according to claim 12, wherein M is Cu; X is $Cl^-$ or $PF_6^-$; and i, j, and k are each 2.

14. A phenanthridine derivative according to claim 5, wherein $R^1$ and $R^2$ are each ethyl or 2-ethylhexyl.

15. A phenanthridine derivative according to claim 6, wherein $R^3$ is a hydrogen atom, methyl, or methoxy; $R^4$, $R^7$, and $R^8$ are each a hydrogen atom or halogen atom.

16. A phenanthridine derivative according to claim 4, wherein l, m and o are each 1.

17. A method for preparing a phenanthridine derivative set forth in to claim 1, comprising the steps of: reacting a 4-hydroxyphenanthridine of formula 6,

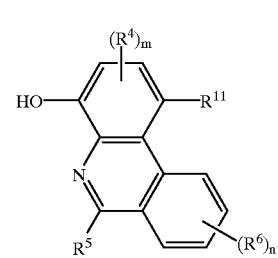

(6)

where $R^4$, $R^5$, and $R^6$ each independently are a hydrogen atom or electron withdrawing group, $R^{10}$ is a hydrogen atom or a halogen atom, n is an integer of 1–4, and m is an integer of 1 or 2, with a p-N, N-substituted aminoaniline compound of formula 8,

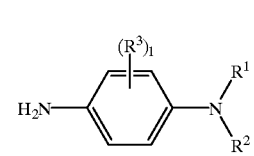

(8)

where $R^1$ and $R^2$ each independently are a hydrogen atom, alkyl group, or aryl group, or jointly form a five- or six-member nitrogen heterocycle or a polycyclic ring containing said five- or six-member nitrogen heterocycle; $R^8$ is a hydrogen atom or electron donating group; and l is an integer of 1–4, to form the phenanthridine derivative of formula 3; and recovering said phenanthridine derivative.

18. A method for preparing a phenanthridine derivative metal complex set forth in to claim 2, comprising the steps of: chelating a phenanthridine derivative of formula 3:

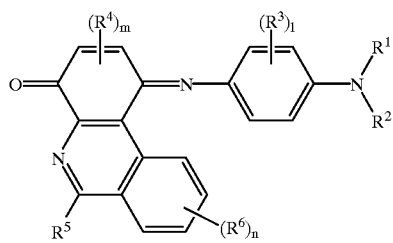
(3)

wherein $R^1$ and $R^2$ each independently are a hydrogen atom, alkyl group, or aryl group, or jointly form a five- or six-member nitrogen heterocycle or a polycyclic ring containing said five- or six-member nitrogen cycle; $R^3$ is a hydrogen atom or electron donating groups; and $R^4$, $R^5$, and $R^6$ each independently are a hydrogen atom or electron withdrawing groups; whereas l and n are each independently an integer of 1–4, and m is an integer of 1 or 2, with an inorganic metal salt of formula 9, $$M^{r+}(X)_s \cdot t(H_2O) \quad (9)$$

where M is a metal atom, r and s each independently an integer of 1–3, and t is an integer of 0–20, to form the phenanthridine derivative metal complex of formula 1; and recovering said phenanthridine derivative metal complex.

* * * * *